US007888326B2

(12) United States Patent
Greene et al.

(10) Patent No.: US 7,888,326 B2
(45) Date of Patent: Feb. 15, 2011

(54) METHODS FOR PROMOTING APOPTOSIS AND TREATING TUMOR CELLS INHIBITING THE EXPRESSION OR FUNCTION OF THE TRANSCRIPTION FACTOR ATF5

(75) Inventors: Lloyd A Greene, Larchmont, NY (US); James M Angelastro, Davis, CA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 337 days.

(21) Appl. No.: 12/062,178

(22) Filed: Apr. 3, 2008

(65) Prior Publication Data
US 2009/0018096 A1    Jan. 15, 2009

Related U.S. Application Data

(60) Division of application No. 10/971,483, filed on Oct. 22, 2004, which is a continuation-in-part of application No. 10/809,312, filed on Mar. 24, 2004, now abandoned.

(60) Provisional application No. 60/460,242, filed on Apr. 4, 2003.

(51) Int. Cl.
A61K 48/00 (2006.01)
A61K 39/395 (2006.01)
A01N 63/00 (2006.01)
A01N 65/00 (2009.01)

(52) U.S. Cl. .................. 514/44 R; 424/93.1; 424/130.1

(58) Field of Classification Search ........................ None
See application file for complete search history.

(56) References Cited

U.S. PATENT DOCUMENTS

| 6,278,039 | B1 | 8/2001 | Johnson et al. |
| 7,390,659 | B2 | 6/2008 | Jessell et al. |
| 7,510,706 | B2 | 3/2009 | Yonemitsu et al. |
| 2002/0006664 | A1 | 1/2002 | Sabatini |
| 2002/0052308 | A1 | 5/2002 | Rosen et al. |
| 2003/0203489 | A1 | 10/2003 | Yonemitsu et al. |
| 2004/0014210 | A1 | 1/2004 | Jessell et al. |
| 2005/0164384 | A1 | 7/2005 | Greene et al. |
| 2007/0092495 | A1 | 4/2007 | Greene et al. |
| 2009/0018096 | A1 | 1/2009 | Greene et al. |

FOREIGN PATENT DOCUMENTS

| WO | WO 99/32619 A1 | 7/1999 |
| WO | WO 01/29058 A1 | 4/2001 |
| WO | WO 01/68836 A2 | 9/2001 |
| WO | WO 01/96584 A2 | 12/2001 |

OTHER PUBLICATIONS

Wei, et al. (2006) Biochemical and Biophysical Research Communications, 339(2): 591-96.*
Advisory Action mailed on Apr. 8, 2009 for U.S. Appl. No. 10/809,312, Greene et al.
Ahmed et al., BDNF enhances the differentiation but not the survival of CNC stem cell-derived neuronal precursors. J. Neurosci., 15:5765-78, 1995.
Aiello, et al. Adenovirus 5 DNA sequences present and RNA sequences transcribed in transformed human embryo kidney cells (HEK-Ad-5 or 293). Virology, 94: 460-469, 1979.
Angelastro et al., Downregulation of activating transcription factor 5 is required for differentiation of neural progenitor cells into astrocytes, J. Neurosci. Apr. 13, 2005;25(15): 3889-99.
Angelastro et al., Characterization of a novel isoform of caspase-9 that inhibits apoptosis. J. Biol. Chem., 276:12190-200, 2001.
Angelastro et al., Identification of diverse nerve growth factor-regulated genes by serial analysis of gene expression (SAGE) profiling. Proc. Natl. Acad. Sci. USA, 97:10424-29, 2000.
Angelastro et al., Regulated expression of ATF5 is required for the progression of neural progenitor cells to neurons, J. Neurosci., 23:4590-4600, 2003.
Angelastro, J.M. et al. 2002. GenBank Accession No. AY123225, *Rattus norvegicus* strain NEDH activating transcription factor 5 (Atf5) mRNA, complete cds, 1034 bp mRNA.
Asai et al., Negative effects of wild-type p53 and s-Myc on cellular growth and tumorigenicity of glioma cells. Implication of the tumor suppressor genes for gene therapy. J. Neurooncol., 19:259-268, 1994.
Ashrafi et al., Genome-wide RNAi analysis of *Caenorhabditis elegans* fat regulatory genes, Nature, 421:268-72, 2003.
Badie et al., Combined radiation and p53 gene therapy of malignant glioma cells, Cancer Gene Ther., 6:155-162, 1999.

(Continued)

*Primary Examiner*—Robert M Kelly
(74) *Attorney, Agent, or Firm*—Baker Botts L.L.P.

(57) ABSTRACT

The present invention provides methods for regulating the growth and/or survival of tumor cells and stem cells by modulating the expression or function of ATF5. The present invention also provides methods for promoting or suppressing differentiation of stem/progenitor cells, for producing differentiated cells and for isolating/purifying differentiated cells, including neural cells. Also provided are differentiated cells, cell populations and transgenic animals comprising same and uses of same. The present invention further provides methods for treating nervous tissue degeneration and for identifying an agent for use in treating nervous tissue degeneration. Methods for promoting apoptosis in neoplastic cells and for treating or preventing tumors, and identifying agents for use in treating or preventing tumors are also provided by the present invention. The present invention further provides methods for identifying agents that inhibit ATF5, agents identified by these methods. Also provided are methods for diagnosing tumors, for assessing the efficacy of therapy to treat tumors and for assessing the prognosis of a subject who has a neural tumor. Finally, the present invention provides a kits for use in detecting and treating tumors.

15 Claims, 16 Drawing Sheets

OTHER PUBLICATIONS

Barco et al., Expression of constitutively active CREB protein facilitates the late phase of long-term potentiation by enhancing synaptic capture. Cell, 108:689-03, 2002.

Bartley et al., Stem cell therapy for cerebral palsy, Expert Opin. Biol Ther. (2003);3(4):541-49.

Beers and Berkow, eds., The Merck Manual of Diagnosis and Therapy, 17th ed. (Whitehouse Station, NJ: Merck Research Laboratories, 1999) chap. 183.

Bhatia, AC133 expression in human stem cells, Leukemia, 15:1685-88, 2001.

Bieri et al., Abnormal nerve conduction studies in mice expression a mutant form of the POU transcription factor, SCIP. J. Neurosci. Res., 50:821-28, 1997.

Billy et al., Specific interference with gene expression induced by long, double-straned RNA in mouse embryonal teratocarcinoma cell lines. Proc. Natl. Acad. Sci. USA, 98:14428-33, 2001.

Björklund et al., Towards a neuroprotective gene therapy for Parkinson's disease: use of adenovirus, AAV and lentivirus vectors for gene transfer of GDNF to the nigrostriatal system in the rat Parkinson model, Brain Res. (2000);886:82-98.

Bodansky, Principles of peptide synthesis, New York: Springer-Verlag New York, Inc. (1984) (Table of Contents only).

Bonaldo, M.F. et al. 1996. GenBank Accession No. AI576016, UI-R-G0-ur-g-10-0-UI.s2 UI-R-Go *Rattus norvegicus* cDNA clone UI-R-G0-ur-g-10-0-UI 3', mRNA sequence, 504 bp mRNA.

Burstein and Greene, Evidence for RNA synthesis-dependent and independent pathways in stimulation of neurite outgrowth by nerve growth factor. Proc. Natl. Acad. Sci. USA 75:6059-63, 1978.

Canman, C.E. Replication checkpoint: preventing mitotic catastrophe. Curr. Biol. 11:R121-124, 2001.

Carroll, et al., The role of natural killer cells in adenovirus-mediated p53 gene therapy, 1 Cancer Ther. (2001);1(1):49-60.

Cassiman, et al., Human and rat hepatic stellate cells express neurotrophins and neurotrophin receptors, Hepatology, 33(1): 148-58, 2001.

Castedo, et al., Cell death by mitotic catastophe: a molecular definition, Oncogene, 23:2825-2837, 2004.

Collins, V. P. Brain tumours: classification and genes, J. Neurol. Neurosurg. Pyschiatry, 75 Suppl 2: ii2-11, 2004.

Cottrell et al., Silence of the strands: RNA interference in eukaryotic pathogens, Trends Microbiol. 11(1):37-43, 2003.

Cottrell et al., Silence of the strands: RNA interference in eukaryotic pathogens. Trends Microbiol., 11:37-43, 2003.

Dai, C. et al. Glioma models. Biochem. Biophys. Acta., 1551: M19-27, 2001.

Dawson and Ginty, CRED family transcription factors inhibit neuronal suicide, Nat. Med., 8:450-51, 2002.

Defer et al., Long-term outcome of unilaterally transplanted parkinsonian patients I. Clinical approach, Brain, 119(Pt 1) 41-50, 1996.

Deshmukh, et al. Genetic and metabolic status of NGF-deprived sympathetic neurons saved by an inhibitor of ICE family proteases. J. Cell Biol. 135: 1341-1354, 1996.

Dicicco-Bloom et al. The PACAP ligand/receptor system regulates cerebral cortical neurogenesis. Ann. N.Y. Acad. Sci., 865:274-89, 1998.

Escobar et al., RNAi-mediated oncogene silencing confers resistance to crown gall tumorigenesis. Proc. Natl. Acad. Sci. USA, 98: 13437-42, 2001.

Final Rejection mailed on Nov. 19, 2008 for U.S. Appl. No. 10/809,312, Greene, et al.

Finkbeiner et al., CREB: a major mediator of neuronal neurotrophin responses, Neuron, 19:1031-47, 1997.

Fukumitsu et al., Simultaneous expression of brain-derived neurotrophic factor and neurotophin-3 in Cajal-Retzius, subplate and ventricular progenitor cells during early development stages of the rat cerebral cortex. Neuroscience. 84;115-27, 1998.

Gage, F.H., Mamalian neural stem cells. Science, 287:1433-38, 2000.

Gerlach M, Braak H, Hartmann A, Jost WH, Odin P, Priller J.Schwarz J. Current state of stem cell research for the treatment of Parkinson's disease J. Neurol., 249 Suppl 3:111/33-5, Oct. 2002.

Ghosh and Greenberg, Distinct roles for bFGF and NT-3 in the regulation of cortical neurogenesis. Neuron. 15:89-03, 1995.

Gratch, et al., Noggin and Chordin have distinct activities in promoting lineage commitment of mouse embryonic stem (es) cells, Developmental Biology, 83-94, 2002.

Greene et al., Culture and experimental use of the PC12 rat pheochromocytoma cell line, Culturing nerve cells, 2nd ed., Goslin, G.K., ed., Cambridge, MA, The MIT Press, pp. 161-188, 1998.

Greene et al., Establishment of a noradrenergic clonal line of rat adrenal pheochromocytoma cells which respond to nerve growth factor, Proc. Natl. Acad. Sci. USA, 73:2424-28, 1976.

Gross and Meienhofer, eds., Peptides: Analysis, Synthesis, Biology: Modern techniques of peptide and amino acid analysis, New York: John Wiley and Sons. (1981)(Table of Contents only).

Gunning et al., Differential and synergistic actions of nerve growth factor and cyclic AMP in PC12 cells. J. Cell Biol., 89:240-45, 1981.

Hansen et al., Mouse Atf5: molecular cloning of two novel mRNAs, genomic organization, and odorant sensory neuron localization. Genomics, 80:344-50, 2002.

Hirose et al., Abrogation of the Chk1-mediated G(2) checkpoint pathway protentiates temozolomide-induced toxicity in a p53-independent manner in human gliobastoma cells, Cancer Res., 61:5843-5849, 2001.

Julius et al., Q vectors, bicistronic retroviral vectors for gene transfer. Biotechniques, 28:702-08, 2000.

Kalcheim, et al., Developmental Biology, 116(2): 451-66, 1986. (Abstract Only Proved).

Kintner, C., Neurogenesis in embryos and in adult neural stem cells. J. Neurosci., 22:639-43, 2002.

Kleihues, et al., Histology Typing of Tumours of the Central Nervous System, Berlin: Springer-Verlag., 1993.

Krylov et al., Extending dimerization interfaces: the bZIP basic region can form a coiled coil. EMBO J., 14:5329-37, 1995.

Kukekov et al., A nestin-negative precursor cell from the adult mouse brain gives rise to neurons and glia. Glia, 21:399-07, 1997.

Kukekov et al., Multipotent stem/progenitor cells with similar properties arise from two neurogenic regions of adult human brain. Exp. Neurol., 156:333-44, 1999.

Laywell et al., Identification of a multipotent astrocytic stem cell in the immature and adult mouse brain. Proc. Natl. Acad. Sci. USA, 97:13883-888, 2000.

Laywell et al., Multipotent neurospheres can be derived from forebrain subependymal zone and spinal cord of adult mice after protracted postmortem intervals. Exp. Neurol. 156:430-33, 1999.

Le Belle and Svendsen, "Stem cells for: neurodegenerative disorders: where can we go from here?" BioDrugs, 16:389-401, 2002. (Abstract only).

Lee et al, Posttranslational modification of class III beta-tubulin, Proc. Natl. Acad. Sci. USA, 87:7195-99, 1990.

Lee, N. H. et al. GenBank Accession No. AW917099, EST348403 Rat gene index, normalized rat, norvegicus, Bento Soares Rattus norvegicus cDNA clone RGIDZ26 5' end, mRNA sequence, 607 by mRNA, 1998.

Lendahl et al., CNA stem cells express a new class of intermediate filament protein. Cell, 60:585-95, 1990.

Li et al., Neuronal differentiation of precursors in the neocortical ventricular zone is triggered by BMP, J. Neurosci., 18:8853-62, 1998.

Lonze et al., Apoptosis, axonal growth defects, and degeneration of peripheral neurons in mice lacking CREB. Neuron, 34:371-85, 2002.

Lu et al., The herpesvirus transactivator VP16 mimics a human basis domain leucine zipper protein, luman, in its interaction with HCF, J. Virol., 72:6291-97, 1998.

Maher et al., Malignant glioma: genetics and biology of a grave matter. Genes Dev., 15:1311-1333, 2001.

Mason et al., ATF5 regulates the proliferation and differentiation of oligodendrocytes, Mol. Cell. Neurosci, 29(3):372-80, 2005.

McLendon et al., Tumors of central neuroepithelial origin, Bigner D et al., eds. Russell and Rubinstein's Pathology of Tumors of the Nervous System, chapter 9, 307-571 Oxford University Press, New York, 1998.

Mendelsohn et al., Stromal cells mediate retinoid-dependent functions essential for renal development. Development, 126:1139-48, 1999.

Moitra et al., Life without white fat: a transgenic mouse. Genes Dev., 12:3168-81, 1998.

Moll et al., Attractive interhelical electrostatic interactions in the proline- and acidic-rich region (PAR) leucine zipper subfamily preclude heterodimerization with other basic leucine zipper subfamilies. J. Biol. Chem., 275:34826-832, 2000.

Nikkah et al., Intranigral fetal dopamine grafts induce behavioral compensation in the rat Parkinson model, J Neurosci. Jun;14(6):3449-61, 1994.

Nikolaev et al., Parc. A. Cytoplasmic Anchor for p53. Cell, 112:29-40, 2003.

Nishizawa and Nagata, cDNA clones encoding leucine-zipper proteins which interact with G-CSF gene promoter element 1-binding protein. FEBS Lett., 299:36-38, 1992.

Non-Final Rejection mailed on Apr. 12, 2006 for U.S. Appl. No. 10/809,312, Greene, et al.

Non-Final Rejection mailed on Aug. 9, 2007 for U.S. Appl. No. 10/809,312, Greene, et al.

Non-Final Rejection mailed on Jul. 9, 2009 for U.S. Appl. No. 10/809,312, Greene, et al.

Non-Final Rejection mailed on May 5, 2008 for U.S. Appl. No. 10/809,312, Greene, et al.

Non-Final Rejection mailed on Sep. 4, 2009 for U.S. Appl. No. 11/524,162, Nitz, et al.

Pati et al., Human Cdc34 and Rad6B ubiquitin-conjugating enzymes target repressors of cyclic AMP-induced transcription for proteolysis. Mol. Cell Biol., 19:5001-13, 1999.

Persengiev et al., Inhibition of apoptosis by ATFx: a noval role for a member of the ATF/CREB family of mamalian bZIP transcription factors. Genes Dev., 16: 18-6-14, 2002.

Peters et al. (ATF-7, a novel bZIP protein, interacts with the PRL-1 protein-tyrosine phosphatase. J. Biol. Chem., 276:13718-26, 2001.

Placzek et al., Patterning cascades in the neural tube, Neural development Curr. Biol., 6:526-29, 1996.

Pluchino et al., Neural stem cells and their use as therapeutic tool in neurological disorders. Brain Res Brain Res Rev. 2005 Apr;48(2):211-9. Epub 2005.

Qi, et al., Characterization of a CNS cell line, CAD, in which morphological differentiation is initiated by a serum deprivation. J. Neurosci., 17:1217-1225, 1997.

Rasheed, et al., Molecular pathogenesis of malignant gliomas. Curr Opin Oncol., 11:162-167, 1999.

Request for Continued Examination (RCE) and Amendments filed on Apr. 20, 2009 for U.S. Appl. No. 10/809,312, Greene, et al.

Response to the Final Rejection mailed on Nov. 19, 2008 filed on Mar. 17, 2009 for U.S. Appl. No. 10/809,312, Greene et al.

Response to the non-Final Rejection mailed on Apr. 12, 2006 filed on Aug. 18, 2006 for U.S. Appl. No. 10/809,312, Greene, et al.

Response to the non-Final Rejection mailed on Aug. 9, 2007 filed on Jan. 9, 2008 for U.S. Appl. No. 10/809,312, Greene, et al.

Response to the non-Final Rejection mailed on May 5, 2008 filed on Aug. 5, 2008 for U.S. Appl. No. 10/809,312, Greene, et al.

Response to the non-Final Rejection mailed on Sep. 4, 2009 filed on Feb. 4, 2010 for U.S. Appl. No. 11/524,162, Nitz, et al.

Sambrook et al., Molecular Cloning. In: A Laboratory Manual, 2nd ed. (Cold Spring Harbor. NY: Cold Spring Harbor Laboratory Press) pp. 16-66, 1989.

Savitz et al., Cell transplants offer promise for stroke recovery, Journal of Cardiovascular Nursing, 18(1): 57-61, 2003.

Schuurmans and Guillemot, Molecular mechanisms underlying cell fate specification in the developing telencephalon, Curr. Opin. Neurobiol., 12:26-34, 2002.

Sonoda et al., Formation of intracranial tumors by genetically modified human astrocytes defines four pathways critical in the development of human anaplastic astrocytoma. Cancer Res., 61:4956-4960, 2001.

Stanworth et al., Stem Cells: Progress in research and edging towards the clinical setting. Clin Med. Sep-Oct; 1(5):378-82, 2001.

Takemura et al., In situ localization of tau mRNA in developing rat brain. Neuroscience, 44:393-07, 1991.

Thomas et al., Progress and problems with the use of viral vectors for gene therapy. Nat Rev Genet. 4(5):346-58, 2003.

Torchillin, Drug targeting, European Journal of Pharmacological Science, 11 Suppl 2: S81-91, 2000.

Towbin et al., Electrophoretic transfer of proteins from polyacrylamide gets to nitrocellulose sheets: procedure and some applications. Proc. Natl. Acad. Sci. USA 76:4350-54, 1979.

Trim et al., Hepatic stellate cells express the low affinity nerve growth factor receptor p75 and undergo apoptosis in response to nerve growth factor stimulation, American Journal of Pathology, 156(4): 1235-43, 2000.

Uchida et al., Direct isolation of human central nervous system stem cell. Proc. Natls. Acad. Sci. USA, 97:14720-25, 2000.

Vinson et al., Dimerization specificity of the leucine zipper-containing bZIP motif on DNA binding: prediction and rational design. Genes Dev., 7:1047-58, 1993.

Vogelbaum et al., Overexpression of bax in human glioma cell lines. J. Neurosurg., 91:483-489, 1999.

Waxman and Bennett, Relative conduction velocities of small myelinated and nonmyelinated fibres in the central nervous system. Nature New Biol., 238:217, 1972.

Wilda et al., Killing of leukemic cells with a BCR/ABL fusion gene RNA interference (RNAi). Oncogene, 21:5716-24, 2002.

Yamagishi, et al., Modification of the radiosensitivity of human cells to which simian virus 40 T-antigen was transfected. J Radiat. Res. (Tokyo), 36:239-247, 1995.

Yin et al., AC133, a novel marker for human hematopoietic stem and progenitor cells. Blood, 90:5002-12, 1997.

Yu et al., AC133-2, a novel isoform of human AC133 stem cell antigen J. Biol. Chem., 277:20711-716, 2002.

Zecca et al., Anti-CD20 monoclonal antibody for the treatment of severe, immune-mediated, pure red cell aplasia and hemolytic anemia, Blood, 97(12):3995-7, 2001.

* cited by examiner

```
   1 gcacctgtgc ctcagccatg tcactcctgg cgaccctggg actggagctg gacagggccc
  61 tgctcccagc tagcgggctg ggctggctcg tagactatgg gaaactcccc ctggcccctg
 121 cccccctggg ccctatgag gtccttgggg gtgccctgga gggcgggctt ccagggggg
 181 gagagcccct ggcaggtgac ggcttctctg attggatgac cgagcgggtg gacttcacag
 241 ccctccttcc tctggaggcc cctctgcccc caggcactct cccccacccc tccctgccc
 301 cccctgacct ggaagccatg gcatccctac tcaagaagga gctagaacag atggaagact
 361 tcttccttga tgccccactc cttccaccgc cctccccacc tccaccccca ccccagcac
 421 cctctctgcc cctgcccctta cccttgccca cctttgatct cccgcagcct cctaccctgg
 481 ataccctgga ctgctagct gttactgcc gcagtgaggc tgggccaggg gattcaggct
 541 tgacaaccct gcctgtcccc cagcagcctc ctcctctggc ccctctgcct tcaccctccc
 601 gaccagcccc ctatcctagt cctgccagca cccgagggga ccgcaagcaa aagaagagag
 661 accagaataa gtcagctgct ctcaggtacc gccagaggaa gcgggcagag ggcgaggccc
 721 tggagggcga gtgccaaggg ctagaggcgc ggaatcggga gctgagggag agggcagagt
 781 cagtggaacg ggagatccag tatgtgaagg atctgctaat tgaggtgtat aaggcacgaa
 841 gccagaggac ccgcagtgcc tagggtacag gaggaggcag ttctggtgta cctgtgcctc
 901 cagcttcacc ctgtccctcc atttcacttc cctgtgcatc cgtgtctagg tctcccctct
 961 gcctatcccc attatgggtt atttggcata gtcagtttct gtaccccttc agtgcaactg
1021 agaaccaagc tcga        SEQ ID NO:1
```

Fig. 8

MSLLATLGLELDRALLPASGLGWLVDYGKLPLAPAPLGPYEVLGGALEGGLP
GGGEPLAGDGFSDWMTERVDFTALLPLEAPLPPGTLPPPSPAPPDLEAMAS
LLKKELEQMEDFFLDAPLLPPPSPPPPPPPAPSLPLPLPLPTFDLPQPPTLDTL
DLLAVYCRSEAGPGDSGLTTLPVPQQPPPLAPLPSPSRPAPYPSPASTRGDR
KQKKRDQNKSAALRYRQRKRAEGEALEGECQGLEARNRELRERAESVEREI
QYVKDLLIEVYKARSQRTRSA    SEQ ID NO:2

Fig. 9

METHODS FOR PROMOTING APOPTOSIS AND TREATING TUMOR CELLS INHIBITING THE EXPRESSION OR FUNCTION OF THE TRANSCRIPTION FACTOR ATF5

CROSS REFERENCE TO RELATED APPLICATIONS

The present application is a divisional of U.S. Nonprovisional application Ser. No. 10/971,483, filed Oct. 22, 2004, presently pending, which is a continuation-in-part of U.S. Nonprovisional application Ser. No. 10/809,312, filed Mar. 24, 2004, now abandoned; which claims benefit of U.S. Provisional Application Ser. No. 60/460,242 filed Apr. 4, 2003; each of which are incorporated by reference in their entireties herein.

STATEMENT OF GOVERNMENT INTEREST

This invention was made with government support under Grant No. NS-16036 awarded by NIH/NINCDS. The government has certain rights in the invention.

SEQUENCE LISTING

The specification further incorporates by reference the Sequence Listing submitted herewith via EFS on Apr. 3, 2008. Pursuant to 37 C.F.R. §1.52(e)(5), the Sequence Listing text file, identified as "SEQLIST_ATF5.TXT," is 8,430 bytes and was created on Apr. 3, 2008. The Sequence Listing, electronically filed herewith, does not extend beyond the scope of the specification and thus does not contain new matter.

BACKGROUND OF THE INVENTION

A key step in the formation of the nervous system is the determination of proliferating neural progenitor cells to undergo differentiation into neurons and glia. Despite major advances in identification and characterization of neural progenitor cells (Placzek and Furley, Patterning cascades in the neural tube. Neural development. Curr. Biol., 6:526-29, 1996; Gage, F. H., Mammalian neural stem cells. Science, 287:1433-38, 2000; Kintner, C., Neurogenesis in embryos and in adult neural stem cells. J. Neurosci., 22:639-43, 2002; Schuurmans and Guillemot, Molecular mechanisms underlying cell fate specification in the developing telencephalon. Curr. Opin. Neurobiol., 12:26-34, 2002), the mechanisms that govern this determination are only partially understood.

The selective degeneration of specific types or classes of neurons of the central nervous system (CNS) underlies many neurological disorders. This realization has generated interest in defining populations of progenitor cells that, through manipulation of the differentiation process, may serve as replenishable sources of neurons and glia, and, therefore, may present an option for treating neurodegenerative and demyelinating disorders. Additionally, it is well recognized that neural tumors and other cancers develop when cells divide and grow uncontrollably. Thus, a means of manipulating the proliferation, differentiation and/or survival of tumor cells may provide a therapy for the treatment of cancers.

Neural degeneration may result from neurodegenerative diseases, CNS traumas, stroke, and the acquired secondary effects of non-neural dysfunction. Alzheimer's disease is a neurodegenerative disease characterized by a progressive, inexorable loss of cognitive function. The pathogenesis of Alzheimer's disease is associated with an excessive number of neuritic, or senile, plaques (composed of neurites, astrocytes, and glial cells around an amyloid core) in the cerebral cortex, and neurofibrillary tangles (composed of paired helical filaments). Approximately 4 million Americans suffer from Alzheimer's disease, at an annual cost of about $90 billion. The disease is about twice as common in women as in men, and accounts for more than 65% of the dementias in the elderly. While senile plaques and neurofibrillary tangles occur with normal aging, they are much more prevalent in persons with Alzheimer's disease. To date, a cure for Alzheimer's disease is not available, and cognitive decline is inevitable.

Demyelination is also a feature of many neurologic disorders. Demyelinating conditions are manifested in loss of myelin—the multiple dense layers of lipids and protein which cover many nerve fibers. Multiple sclerosis (MS) is the most prevalent demyelinating condition. In Europe and North America, an average of 40-100 people out of every 100,000 have MS. The disease affects approximately 250,000 people in the United States alone. Histopathologically, MS is characterized by inflammation, plaques of demyelination infiltrating cells in the CNS tissue, loss of oligodendroglia, and focal axonal injury. Typically, the symptoms of MS include lack of co-ordination, paresthesias, speech and visual disturbances, and weakness. Current treatments for the various demyelinating conditions are often expensive, symptomatic, and only partially effective, and may cause undesirable secondary effects. Corticosteroids represent the main form of therapy for MS. While these may shorten the symptomatic period during attacks, they may not affect eventual long-term disability. Long-term corticosteroid treatment is rarely justified, and can cause numerous medical complications, including osteoporosis, ulcers, and diabetes.

Approximately one million people are diagnosed with cancer each year, and many millions of Americans of all ages are currently living with some form of cancer. At some time during the course of their lifetime, one out of every two American men and one out of every three American women will be diagnosed with some form of cancer. Of the one million Americans diagnosed with cancer annually, 17,000 are diagnosed with brain tumors. Brain tumors invade and destroy normal tissue, producing such effects as impaired sensorimotor and cognitive function, increased intracranial pressure, cerebral edema, and compression of brain tissue, cranial nerves, and cerebral vessels. Drowsiness, lethargy, obtuseness, personality changes, disordered conduct, and impaired mental faculties are the initial symptoms in 25% of patients with malignant brain tumors. Treatment of brain tumors is often multimodal, and depends on pathology and location of the tumors. For malignant gliomas, multimodal therapy, including chemotherapy, radiation therapy, and surgery, is used to try to reduce tumor mass. Regardless of approach, however, prognosis for patients suffering from these tumors is guarded: the median term of survival after chemotherapy, radiation therapy, and surgery is only about 1 year, and only 25% of these patients survive for 2 years.

In particular, malignant astrocytic tumors occur in the human population at a frequency of 7 per 100,000 per year (Maher, et al. Malignant glioma: genetics and biology of a grave matter. Genes Dev., 15: 1311-1333, 2001; Rasheed, et al. Molecular pathogenesis of malignant gliomas. Curr Opin Oncol., 11: 162-167, 1999), making them the most common form of primary brain tumor. There is currently no effective curative therapy for patients with WHO classification Grade IV glioblastomas (also designated glioblastoma multiforme or GBM) and the average survival time from diagnosis is approximately 9-11 months (McLendon, et al. Tumors of central neuroepithelial origin, p. 307-571, 1998; Kleihues, et al. Histology Typing of Tumours of the Central Nervous System. *Berlin: Springer-Verlag.,* 1993.).

Findings that neural progenitor/stem cells may be experimentally transformed into glioblastomas has supported the possibility that such tumors may arise from self-renewing progenitors that have lost the capacity for appropriate regulation of proliferation and survival (Dai, C. et al. Glioma models. *Biochem. Biophys. Acta.,* 1551: M19-27, 2001). Indeed, GBMs are often associated with disregulation of pathways that control growth and survival including those involving p53, Rb, PTEN and growth factor receptors (reviewed by Collins (Collins, V. P. Brain tumours: classification and genes. *J. Neurol. Neurosurg. Psychiatry,* 75 Suppl 2: ii2-11, 2004). Additional novel regulatory genes may also contribute to blocking GBM cells from undergoing full differentiation and maintaining them in a state of uncontrolled growth.

In view of the foregoing, it is clear that many neural disorders are related to loss of cells, loss of myelin, or loss of cell control. An ability to regulate the differentiation of neuroprogenitor cells into various differentiated neural cells would provide supplies of neural cells that could be effective in treating such neural disorders. Additionally, the ability to regulate the growth and/or survival of tumor cells would be effective in treating an array of neoplastic disorders. However, prior to the present invention, manipulating whether or not neural progenitor cells differentiate into neurons and/or glia continue to divide and to remain as progenitor cells, as well as the general regulation of the growth and/or survival of stem cells and tumor cells has proved difficult.

SUMMARY OF THE INVENTION

The inventors disclose herein that the b-zip transcription factor, ATF5, plays a major regulatory role in the differentiation of neuroprogenitor cells into differentiated neural cells. In particular, the inventors have discovered that, in the developing brain, ATF5 expression is high within ventricular zones containing neural stem cells and neural progenitor cells, but is undetectable in post-mitotic neurons and glia. In attached clonal neurosphere cultures, ATF5 is expressed by neural stem cells and neural progenitor cells, but is undetectable in tau-positive neurons, in GFAP positive astrocytes and in the nuclei of mature oligodendroglia. In PC12 cell cultures, nerve growth factor (NGF) dramatically down-regulates endogenous ATF5 protein and transcripts, while exogenous ATF5 suppresses NGF-promoted neurite outgrowth. Such inhibition may require repression of cyclic AMP (cAMP) responsive element (CRE) DNA-binding sites and/or other ATF5 DNA-binding sites, including those not yet discovered. By contrast, loss of function conferred by dominant-negative ATF5 accelerates NGF-promoted neuritogenesis. Exogenous ATF5 suppresses neurogenesis by cultured nestin-positive telencephalic cells, while dominant-negative ATF5, and a small interfering RNA targeted to ATF5, promote this activity. These findings indicate that ATF5 blocks differentiation of neuroprogenitor cells into neurons, and must be down-regulated to permit this process to occur. Additional studies carried out in culture, and also in vivo, indicate that ATF5 blocks differentiation of proliferating neural progenitor cells and oligodendrocyte precursor cells into differentiated astroglia and oligodendroglia, and that dominant-negative ATF5 accelerates this differentiation. Thus, constitutive expression of exogenous ATF5 maintains neural progenitor cells in a proliferative state both in vitro and in vivo and represses their differentiation in the presence extracellular signals such as NGF, NT3 and CNTF that otherwise promote differentiation and down-regulation of endogenous ATF5. By contrast, loss of ATF5 function or expression achieved with a dominant negative form of ATF5 or with a small interfering RNA, respectively, accelerates the differentiation of neural progenitors into non-dividing neurons and glia (Angelastro, et al. Regulated expression of ATF5 is required for the progression of neural progenitor cells to neurons. *J. Neurosci.,* 23: 4590-4600, 2003; Angelastro et al., unpublished data).

The inventors additionally disclose herein that ATF5 is widely expressed by various tumor types. In particular, the inventors have shown that ATF5 is expressed not only in highly proliferative neural tumors, e.g., glioblastomas, but is also expressed in multiple neoplasias including, but not necessarily limited to: breast, ovary, endometrium, gastric, colon, liver, pancrease, kidney, bladder, prostate, testis, skin, esophagus, tongue, mouth, parotid, larynx, pharynx, lymph node, lung, and brain tumors. Further, the inventors have demonstrated for the first time that interfering with the function or expression of ATF5 promotes apoptosis of glioblastoma multiforme tumor cells (GBM) in vitro and in vivo. The inventors have also shown for the first time that selective interference with ATF5 function in other carcinoma types, e.g., breast tumors, also triggers cell death. Importantly, the effect of ATF5 interference is specific in that interfering with ATF5 function triggers increased cell death in neoplastic cells, but not normal cells.

Accordingly, the present invention provides a method for regulating the growth and/or survival of tumor cells and stem cells by modulating the expression or function of ATF5. The invention additionally provides methods for promoting differentiation of a neural stem cell or a neural progenitor cell into a differentiated neural cell, by inhibiting ATF5 function or expression in the cell. Also provided is a differentiated neural cell produced by this method.

The present invention also provides a method for producing differentiated neural cells by: (a) obtaining or generating a culture of neural stem cells or neural progenitor cells; (b) contacting the culture of neural stem cells or neural progenitor cells with an amount of an ATF5 inhibitor effective to produce differentiated neural cells; and (c) optionally, contacting the differentiated neural cells with at least one neurotrophic factor. Examples of methods for contacting the cells with (treating the cells with) the ATF5 inhibitor or the neurotrophic factor (in protein or nucleic acid form) include, without limitation, absorption, electroporation, immersion, injection, liposome delivery, transfection, vectors, and other protein-delivery and nucleic-acid-delivery vehicles and methods. Also provided is a population of cells, comprising the differentiated neural cells produced by this method.

The present invention further provides a method for treating nervous tissue degeneration in a subject in need of treatment by: (a) obtaining or generating a culture of neural stem cells or neural progenitor cells; (b) contacting the culture of neural stem cells or neural progenitor cells with an amount of an ATF5 inhibitor effective to produce differentiated neural cells; (c) optionally, contacting the differentiated neural cells with at least one neurotrophic factor; and (d) transplanting the differentiated neural cells into the subject in an amount effective to treat the nervous tissue degeneration.

Additionally, the present invention provides differentiated neural cells produced by: (a) obtaining or generating a culture of neural stem cells or neural progenitor cells; (b) contacting the neural stem cells or neural progenitor cells with an amount of an ATF5 inhibitor effective to produce differentiated neural cells; and (c) optionally, contacting the differentiated neural cells with at least one neurotrophic factor. Also provided is a transgenic non-human animal containing these differentiated neural cells, and uses of these differentiated neural cells in analyzing neuron development, function, and death, and in monitoring synaptic differentiation.

The present invention is also directed to a method for isolating and/or purifying a population of differentiated neural cells by: (a) obtaining or generating a culture of neural stem cells or neural progenitor cells that express enhanced green fluorescent protein (eGFP); (b) contacting the culture of neural stem cells or neural progenitor cells with an amount of an ATF5 inhibitor effective to produce differentiated neural cells that express eGFP; (c) optionally, contacting the differentiated neural cells with at least one neurotrophic factor; (d) detecting expression of eGFP in the differentiated neural cells; and (e) isolating the differentiated neural cells that express eGFP.

Furthermore, the present invention provides a method for identifying an agent for use in treating a condition associated with nervous tissue degeneration by: (a) obtaining or generating a culture of neural stem cells or neural progenitor cells; (b) contacting the neural stem cells or neural progenitor cells with an amount of an ATF5 inhibitor effective to produce neurons, wherein some or all of the neurons are degenerated; (c) contacting the degenerated neurons with a candidate agent; and (d) determining if the agent enhances regeneration or survival of some or all of the degenerated neurons.

The present invention also provides a method for suppressing differentiation of neural stem cells or neural progenitor cells into differentiated neural cells, by contacting the neural stem cells or neural progenitor cells with an amount of ATF5 effective to suppress differentiation in the neural stem cells or neural progenitor cells.

Additionally, the present invention is directed to a therapeutic composition, comprising: (a) a nucleic acid encoding an ATF5 inhibitor; (b) a vector; and (c) optionally, a pharmaceutically-acceptable carrier. Also provided is a method for treating a tumor, e.g., a neural tumor, in a subject in need of treatment, by administering the therapeutic composition to the subject.

The present invention further provides a method for identifying an agent which inhibits ATF5 by: (a) contacting a candidate agent with ATF5, in the presence of CRE; and (b) assessing the ability of the candidate agent to inhibit interaction between ATF5 and CRE. This method may further comprise the steps of: (c) contacting the candidate agent with neural stem cells or neural progenitor cells containing ATF5; and (d) determining if the agent has an effect on an ATF5-associated biological event in the cells. Also provided are agents identified by these methods, as well as methods for promoting differentiation in neural stem cells or neural progenitor cells, and for treating or preventing a neural tumor in a subject, using these agents.

The present invention additionally provides methods for promoting apoptosis in a neoplastic cell comprising contacting the neoplastic cell with an ATF5 inhibitor. The neoplastic cell can be selected from the group consisting of: breast, ovary, endometrium, gastric, colon, liver, pancrease, kidney, bladder, prostate, testis, skin, esophagus, tongue, mouth, parotid, larynx, pharynx, lymph node, lung, and brain. In one embodiment, the neoplastic cell is selected from the group consisting of glioblastoma, astrocytoma, glioma, medulloblastoma and neuroblastoma. In other embodiments, the ATF5 inhibitor is a nucleic acid, which can include, but is not limited to a dominant negative form of ATF5 (e.g. NTAzip-ATF5), or ATF5siRNA. The method of the present invention can be performed in vitro as well as in vivo in a subject.

The present invention also provides a methods for treating or preventing a tumor in a subject comprising the steps of: (a) obtaining or generating a culture of turmor cells; and (b) contacting the tumor cells with an amount of an ATF5 inhibitor effective to induce apoptosis in the tumor cells. In one embodiment, the tumor is selected from the group consisting of: breast, ovary, endometrium, gastric, colon, liver, pancrease, kidney, bladder, prostate, testis, skin, esophagus, tongue, mouth, parotid, larynx, pharynx, lymph node, lung, and brain. In another embodiment, the tumor is selected from the group consisting of glioblastoma, astrocytoma, glioma, medulloblastoma and neuroblastoma. In still another embodiment, the ATF5 inhibitor is a nucleic acid.

The invention further provides methods for producing differentiated tumor cells, comprising the steps of: (a) obtaining or generating a culture of tumor cells; (b) contacting the culture of tumor cells with an amount of an ATF5 inhibitor effective to produce differentiated neural cells; and (c) optionally, contacting the differentiated neural cells with at least one neurotrophic factor. The method can be performed in vivo or in vitro.

The invention also provides a method for determining whether a subject has a tumor, comprising assaying a diagnostic sample of the subject for ATF5, wherein detection of an ATF5 level elevated above normal is diagnostic of a tumor in the subject.

The invention further provides methods for assessing the efficacy of therapy to treat a tumor in a subject who has undergone or is undergoing treatment for a tumor, comprising assaying a diagnostic sample of the subject for ATF5, wherein a normal level of ATF5 in the diagnostic sample is indicative of successful therapy to treat the tumor, and a level of ATF5 elevated above normal in the diagnostic sample is indicative of a need to continue therapy to treat the tumor.

The invention also provides methods for assessing the prognosis of a subject who has a tumor, comprising assaying a diagnostic sample of the subject for ATF5, wherein the subject's prognosis improves with a decreased level of ATF5 in the diagnostic sample, and the subject's prognosis worsens with an increased level of ATF5 in the diagnostic sample.

A therapeutic composition for use in treating or preventing a tumor is also provided by the present invention, comprising: (a) a nucleic acid encoding an ATF5 inhibitor; (b) a vector; and (c) optionally, a pharmaceutically-acceptable carrier.

Further, the present invention provides a method for determining whether a subject has a tumor, by assaying a diagnostic sample of the subject for ATF5, wherein detection of an ATF5 level elevated above normal is diagnostic of a tumor in the subject. Also provided are methods for assessing the efficacy of therapy to treat a tumor in a subject who has undergone or is undergoing treatment for a tumor, and for assessing the prognosis of a subject who has a tumor.

Finally, the present invention provides kits for use in detecting, treating and preventing tumors.

Additional aspects of the present invention will be apparent in view of the description which follows.

BRIEF DESCRIPTION OF THE FIGURES

FIG. 8 sets forth the nucleotide sequence of ATF5 (SEQ ID NO: 1).

FIG. 9 sets forth the amino acid sequence of ATF5 (SEQ ID NO:2).

DETAILED DESCRIPTION OF THE INVENTION

Figure 1A:
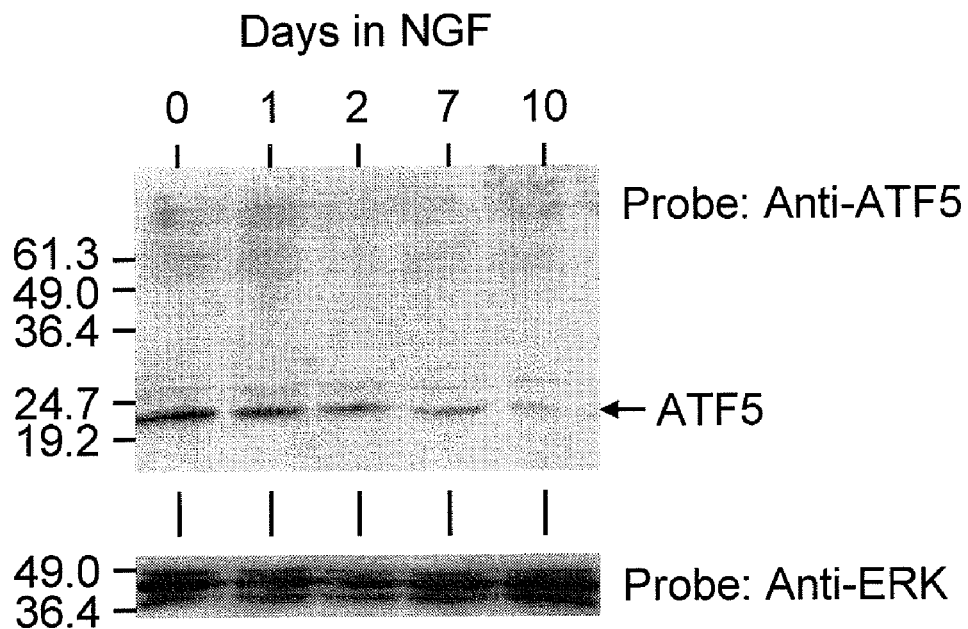
FIG. 1 shows that nerve growth factor (NGF) down-regulates ATF5 protein in PC12 cells, and demonstrates a reciprocal relationship with neurite outgrowth. (A) Time course of the effect of NGF treatment on ATF5 protein expression in PC12 cells. Cells were exposed to NGF for the indicated times, and 135 µg of whole cell extracts were subjected to Western immunoblotting, first with anti-ATF5, then, after stripping, with anti-ERK to normalize for loading. Numbers at the left of the figure indicate the positions of molecular weight markers (in kDa). Comparable results were achieved in 3 independent experiments. (B) Comparison of the kinetics of NGF-dependent down-regulation of ATF5 expression, and promotion of neurite outgrowth. The relative levels of ATF5 expression were determined by densitometry, and normalized to levels of ERK protein in the same sample; the levels are reported in arbitrary units. Proportions of cells bearing neurites of a length at least twice the diameter of the cell body were determined in the same cultures, by scoring at least 200 cells per time point.

As described above, a key step in the formation of the nervous system is the determination of proliferating neural progenitor cells to exit the cell cycle and undergo neuronal differentiation. Despite major advances in identification and characterization of such progenitor cells, the mechanisms that govern this determination are only partially understood.

One system with potential to address this issue is the PC12 line of pheochromocytoma cells (Greene and Tischler, Establishment of a noradrenergic clonal line of rat adrenal pheochromocytoma cells which respond to nerve growth factor. *Proc. Natl. Acad Sci. USA*, 73:2424-28, 1976; Burstein and Greene, Evidence for RNA synthesis-dependent and -independent pathways in stimulation of neurite outgrowth by nerve growth factor. *Proc. Natl. Acad. Sci. USA*, 75:6059-63, 1978). In the presence of the neurotrophic factor, nerve growth factor (NGF), proliferating neuroblast-like PC12 cells acquire, by means of a transcription-dependent mechanism, a neuronal phenotype characterized by formation of axons, up-regulation of a number of neuronal markers, and transition to a post-mitotic state.

To identify genes responsible for this neuronal differentiation, the inventors employed serial analysis of gene expression (SAGE) to provide a comprehensive profile and comparison of transcripts present in PC12 cells, before and after 9 days of treatment with NGF (Angelastro et al., Identification of diverse nerve growth factor-regulated genes by serial analysis of gene expression (SAGE) profiling. *Proc. Natl. Acad. Sci. USA*, 97:10424-29, 2000). Of the approximately 22,000 unique transcripts detected in the cells, approximately 4% underwent a 6-fold or greater increase or decrease in expression after NGF exposure. Among the identified genes with the greatest change in expression was ATF5, a member of the activating transcription factor (ATF/CREB) family. In response to NGF, ATF5 transcripts, which were among the most highly expressed in the cells prior to treatment, fell by 25-fold in relative expression.

Relatively few studies have been carried out to characterize ATF5 (also known as ATFX and ATF-7) and its biological functions (Nishizawa and Nagata, cDNA clones encoding leucine-zipper proteins which interact with G-CSF gene promoter element 1-binding protein. *FEBS Lett.*, 299:36-38, 1992; Pati et al., Human Cdc34 and Rad6B ubiquitin-conjugating enzymes target repressors of cyclic AMP-induced transcription for proteolysis. *Mol. Cell Biol.*, 19:5001-13, 1999; Peters et al., ATF-7, a novel bZIP protein, interacts with the PRL-1 protein-tyrosine phosphatase. *J. Biol Chem.*, 276:13718-726, 2001; Persengiev et al., Inhibition of apoptosis by ATFx: a novel role for a member of the ATF/CREB family of mammalian bZIP transcription factors. *Genes Dev.*, 16:1806-14, 2002). ATF5 is a b-zip transcription factor that forms homodimers that, at least in vitro, bind cyclic AMP (cAMP) responsive element (CRE) DNA-binding sites. In addition, ATF5 represses cAMP-induced transcription in intact cells (Pati et al., Human Cdc34 and Rad6B ubiquitin-conjugating enzymes target repressors of cyclic AMP-induced transcription for proteolysis. *Mol. Cell Biol.*, 19:5001-13, 1999; Peters et al., ATF-7, a novel bZIP protein, interacts with the PRL-1 protein-tyrosine phosphatase. *J. Biol. Chem.*, 276:13718-726, 2001), and has been shown to inhibit apoptosis (Persengiev et al., Inhibition of apoptosis by ATFx: a novel role for a member of the ATF/CREB family of mammalian bZIP transcription factors. *Genes Dev.*, 16:1806-14, 2002). This raised the possibility that ATF5 might interfere with the activity of transcription factors, such as CREB, that appear to promote neuronal differentiation via CRE-mediated gene activation (Finkbeiner et al., CREB: a major mediator of neuronal neurotrophin responses. *Neuron*, 19:1031-47, 1997; Dawson and Ginty, CREB family transcription factors inhibit neuronal suicide. *Nat. Med.*, 8:450-51, 2002; Lonze et al., Apoptosis, axonal growth defects, and degeneration of peripheral neurons in mice lacking CREB. *Neuron*, 34:371-85, 2002). These properties, along with its down-regulation by NGF, suggest that ATF5 is a negative regulator of neuronal differentiation, via CRE and other (as yet undiscovered) DNA-binding sites.

The present invention relates to several findings concerning the levels of expression of ATF5 in cells of the nervous system. In particular, the inventors have discovered that ATF5 is highly expressed in the nuclei of neuroprogenitor cells (in both the developing and adult nervous systems), and that it functions in these cells to block their differentiation into neurons, astroglia, and oligodendroglia. In contrast, ATF5 is only detected outside the nucleus in oligodendroglia and Schwann cells (myelin-forming cells in the CNS and the peripheral nervous system (PNS), respectively), and is not detected in mature neurons or astroglia. Studies also indicate that ATF5 is highly expressed in human neuroblastoma cells.

The inventors have also discovered that ATF5 is widely expressed by various tumor types. In particular, the inventors have shown that ATF5 is expressed not only in highly proliferative neural tumors, e.g., glioblastomas, but is also expressed in multiple neoplasias including, but not necessarily limited to: breast, ovary, endometrium, gastric, colon, liver, pancrease, kidney, bladder, prostate, testis, skin, esophagus, tongue, mouth, parotid, larynx, pharynx, lymph node, lung, and brain tumors. Further, the inventors have demonstrated for the first time that interfering with the function or expression of ATF5 promotes apoptosis of glioblastoma multiforme tumors (GBM) in vitro and in vivo. The inventors have also shown for the first time that selective interference with ATF5 function in other carcinoma types, e.g., breast tumors, also triggers cell death. Importantly, the effect of ATF5 interference is specific in that interfering with ATF5 function triggers increased cell death in neoplastic cells, but not normal cells.

The present invention also relates to a role for ATF5 in the differentiation of progenitor cells, including but not limited to neuroprogenitor cells. For example, the inventors have observed that forced constitutive expression of ATF5 protein in neuroprogenitor cells blocks their differentiation into neurons and glial cells. The inventors have also observed that specific suppression of ATF5 protein synthesis, or forced constitutive expression of a blocking form of the protein, strongly promotes differentiation of neuroprogenitor cells.

Furthermore, the present invention relates to regulation of ATF5 expression. In particular, the inventors' findings indicate that ATF5 expression is regulated by neurotrophic factors, and, therefore, is an essential part of the mechanism by which they promote neuronal differentiation.

Accordingly, the present invention provides a method for promoting differentiation of a stem cell or a neural progenitor cell into a differentiated cell, as well as a differentiated cell produced by this method. Differentiation is the cellular process by which cells become structurally and functionally specialized during development. As used herein, the term "promoting differentiation" means activating, enhancing, inducing, initiating, or stimulating differentiation of a stem cell or a progenitor cell. The stem cell can be a neural stem cell and the progenitor cell can be a neural progenitor cell.

Neural stem cells, for example, are cultured cells, derived from the pluripotent inner cell mass of blastocyst stage embryos, that are capable of replicating indefinitely. In general, neural cells have the potential to differentiate into neural cells (i.e., they are pluripotent); thus, they may serve as a continuous source of new neural cells. The neural stem cell of the present invention may be obtained from any animal, but is preferably obtained from a mammal (e.g., human, domestic animal, or commercial animal). In one embodiment of the present invention, the neural stem cell is a murine neural stem cell. In another, preferred, embodiment, the neural stem cell is obtained from a human.

As used herein, a "differentiated neural cell" is a partially-differentiated or fully-differentiated cell of the central nervous system (CNS) or peripheral nervous system (PNS), and includes, without limitation, a fully-differentiated ganglion cell, glial (or neuroglial) cell (e.g., an astrocyte, astroglial cell, oligodendrocyte, oligodendroglial cell, or Schwann cell), granule cell, neuronal cell (or neuron), and stellate cell, as well as any neural progenitor cells thereof. Progenitor cells are parent cells which, during development and differentiation, give rise to a distinct cell lineage by a series of cell divisions. Neural progenitor cells, for example, are committed to a cell lineage that will develop, eventually, into fully-differentiated neural cells of the CNS or PNS; however, such neural progenitor cells may not yet be dedicated to a particular type, or subclass, of neural cell.

Initially, neural progenitor cells may acquire a rostral character (e.g., rostral neural progenitor cells), followed by a positional identity (e.g., cerebellar progenitor cells, cerebral progenitor cells, or spinal progenitor cells). Such partially-differentiated neural progenitor cells may become committed to a cell line that will differentiate into a specific type of neural cell (e.g., progenitor cells of astrocytes, astroglial cells, ganglion cells, granule cells, neurons, oligodendrocytes, oligodendroglial cells, Schwann cells, or stellate cells), and, thereafter, give rise to fully-differentiated neural cells (e.g., astrocytes, astroglial cells, ganglion cells, granule cells, neurons, oligodendrocytes, oligodendroglial cells, Schwann cells, or stellate cells). Accordingly, the partially-differentiated neural cell of the present invention may be a cell, with a neural identity, that has acquired a directional or positional character, or that has committed to developing into a particular class of neural cell, but is not a fully-differentiated neural cell.

The neural progenitor cell of the present invention may be obtained from any animal, but is preferably obtained from a mammal (e.g., human, domestic animal, or commercial animal). In one embodiment of the present invention, the neural progenitor cell is a murine neural progenitor cell. In another, preferred, embodiment, the neural progenitor cell is obtained from a human.

A "neuronal cell", or "neuron", as used herein, is a conducting or nerve cell of the nervous system that typically consists of a cell body (perikaryon) that contains the nucleus and surrounding cytoplasm; several short, radiating processes (dendrites); and one long process (the axon), which terminates in twig-like branches (telodendrons), and which may have branches (collaterals) projecting along its course. Examples of neurons include, without limitation, cerebellar neurons, or neurons from the cerebellum (e.g., basket cells, Golgi cells, granule cells, Purkinje cells, and stellate cells); cortical neurons, or neurons from the cerebral cortex (e.g., pyramidal cells and stellate cells, including interneurons, midbrain neurons, and neurons of the substantia nigra); hippocampal cells, or cells from the hippocampus (including granule cells); cells of the Pons; neurons of the dorsal root ganglia (DRG); motor neurons; peripheral neurons; sensory neurons; neurons of the spinal cord; ventral interneurons; and primary neurons (neurons taken directly from the brain, and, in general, placed into a tissue culture dish), all of which may be cholinergic, dopaminergic, GABAergic, or serotonergic.

Differentiation of neural stem cells and neural progenitor cells into partially- or fully-differentiated neural cells may be detected by known cellular or molecular procedures, and assays and methods disclosed herein. In one embodiment of the present invention, the differentiated neural cell is a post-mitotic neuron. The term "post-mitotic", as used herein, refers to a neuron that is in G0 phase (a quiescent state), and is no longer dividing or cycling. In another embodiment of the present invention, the differentiated neural cell is marked, in that it expresses enhanced green fluorescent protein (eGFP), as described herein. The eGFP exogenous reporter may be particularly useful in a method for isolating and/or purifying a population of differentiated neural cells, as described below.

The method of the present invention comprises inhibiting ATF5 in a stem cell, progenitor cell or tumor cell. As used herein, "ATF5" includes both an "ATF5 protein" and an "ATF5 analogue". Unless otherwise indicated, "protein" shall include a protein, protein domain, polypeptide, or peptide, and any fragment thereof. The ATF5 protein has the amino acid sequence set forth in FIG. 9, including conservative substitutions thereof. As described below, Western immunoblotting permitted the inventors to deduce the major cellular form of ATF5 protein. The ATF5 cDNA sequence predicts two potential in-frame methionine start sites that would lead to proteins of approximately 30 and 20 kDa. The inventors' observation that the major form of ATF5 in cells has an apparent molecular mass of 20-22 kDa indicates favored utilization of the second site. When a canonical Kozak initiation consensus sequence was included upstream of the first methionine, the larger protein was expressed, thereby indicating that the 22-kDa form is not formed by cleavage of a 30-kDa precursor. Accordingly, the ATF5 protein of the present invention further includes both the 22-kDa and 30-kDa isomers thereof.

As used herein, "conservative substitutions" are those amino acid substitutions which are functionally equivalent to a substituted amino acid residue, either because they have similar polarity or steric arrangement, or because they belong to the same class as the substituted residue (e.g., hydrophobic, acidic, or basic). The term "conservative substitutions" includes substitutions having an inconsequential effect on the ability of ATF5 to interact with CRE, particularly in respect of the use of said interaction for the identification and design of agonists of ATF5, for molecular replacement analyses, and/or for homology modeling.

An "ATF5 analogue", as used herein, is a functional variant of the ATF5 protein, having ATF5 biological activity, that has 60% or greater (preferably, 70% or greater) amino-acid-sequence homology with the ATF5 protein. As further used herein, the term "ATF5 biological activity" refers to the activity of a protein or peptide that demonstrates an ability to associate physically with, or bind with, CRE (i.e., binding of approximately two fold, or, more preferably, approximately five fold, above the background binding of a negative control), under the conditions of the assays described herein, although affinity may be different from that of ATF5.

It will be obvious to the skilled practitioner that the numbering of amino acid residues in ATF5, or in the ATF5 analogues or peptidomimetics covered by the present invention, may be different than that set forth herein, or may contain certain conservative amino acid substitutions that produce the same ATF5-CRE associating activity as that described herein. Corresponding amino acids and conservative substitutions in other isoforms or analogues are easily identified by visually inspecting the relevant amino acid sequences, or by using commercially available homology software programs.

In accordance with methods described herein, ATF5 may be inhibited in a stem cell, progenitor cell or neoplastic cell by disabling, disrupting, or inactivating the function or activity of ATF5 in the cell, or by diminishing the amount or level of ATF5 in the cell. For example, ATF5 in a cell may be inhibited by targeting ATF5 directly. Additionally, activity of ATF5 in a cell may be inhibited indirectly, by targeting an enzyme or other endogenous molecule that regulates or modulates the functions or levels of ATF5 in the cell. ATF5 expression may also be inhibited by engineering the ATF5 gene so that ATF5 is expressed on an inducible promoter. In such a case, ATF5 expression would be sustained in the presence of a suitable inducing agent, but would shut down once the supply of inducer was depleted, thereby resulting in a decrease in the amount or level of ATF5 in the cell.

Preferably, activity of the ATF5 in the cell is inhibited or decreased by at least 10% in the method of the present invention. More preferably, activity of the ATF5 is decreased by at least 20%. Activity of the ATF5 is inhibited in the stem, progenitor or tumor cell by an amount effective to promote differentiation of the stem cell, progenitor cell, tumor cell. This amount may be readily determined by the skilled artisan, based upon known procedures, including analysis of titration curves established in vivo, and methods disclosed herein.

By way of example, activity of the ATF5 in a neuron may be inhibited by directly or indirectly inactivating, interfering with, or down-regulating the CRE-binding function of ATF5 in the neural stem cell or neural progenitor cell (e.g., by the modulation or regulation of proteins that interact with ATF5). The ATF5 in a neural stem cell or neural progenitor cell may be inactivated, for example, by contacting the neural stem cell or neural progenitor cell with a small molecule or protein mimetic that inhibits ATF5 or that is reactive with (i.e., has affinity for, binds to, or is directed against) ATF5. Examples of methods for contacting the cell with (treating the cell with) a molecule or protein mimetic include, without limitation, absorption, electroporation, immersion, injection, liposome delivery, transfection, vectors, and other protein-delivery and nucleic-acid-delivery vehicles and methods, as described below.

Activity of ATF5 in a neural stem cell or neural progenitor cell also may be inhibited by directly or indirectly causing, inducing, or stimulating the down-regulation of ATF5 expression within the cell. Accordingly, in one embodiment of the present invention, activity of ATF5 is inhibited in a neural stem cell or neural progenitor cell by contacting the cell with a modulator of ATF5 expression, in an amount effective to promote differentiation of the cell. The modulator may be a protein, polypeptide, peptide, nucleic acid (including DNA or RNA), antibody, Fab fragment, F(ab')$_2$ fragment, molecule, compound, antibiotic, drug, or an agent reactive with (i.e., has affinity for, binds to, or is directed against) ATF5, that inhibits or down-regulates ATF5 expression. A Fab fragment is a univalent antigen-binding fragment of an antibody, which is produced by papain digestion. An F(ab')$_2$ fragment is a divalent antigen-binding fragment of an antibody, which is produced by pepsin digestion.

Modulators of ATF5 may be identified using a simple screening assay. For example, to screen for candidate modulators of ATF5, neural progenitor cells may be plated onto microtiter plates, then contacted with a library of drugs. Any resulting decrease in, or down-regulation of, ATF5 expression then may be detected using a luminescence reporter, nucleic acid hybridization, and/or immunological techniques known in the art, including an ELISA. Additional modulators of ATF5 expression may be identified using screening procedures well known in the art or disclosed herein. Modulators of ATF5 will include those drugs which inhibit or down-regulate expression of ATF5. In this manner, candidate modulators also may be screened for their ability to promote differentiation of neural stem cells or neural progenitor cells, and, therefore, their ability to treat neural tumors, as discussed below.

In one embodiment of the present invention, ATF5 in a neural stem cell or neural progenitor cell is inhibited by contacting the cell with an ATF5 inhibitor. As used herein, "an ATF5 inhibitor" shall include a protein, polypeptide, peptide, nucleic acid (including DNA, RNA, and an antisense oligonucleotide), antibody (monoclonal and polyclonal, as described above), Fab fragment (as described above), F(ab')$_2$ fragment (as described above), molecule, compound, antibiotic, drug, and any combinations thereof, and may be an agent reactive with ATF5, as defined above. By way of example, the ATF5 inhibitor of the present invention may be a neurotrophic factor. As used herein, a "neurotrophic factor" is a factor involved in the nutrition or maintenance of neural tissue. Neurotrophic factors, may further the development and differentiation of committed neural progenitor cells, or they may induce or enhance the growth and survival of differentiated neural cells. A classic example of a neurotrophic factor is NGF (nerve growth factor). Other examples of neurotrophic factors for use in the present invention include, without limitation, GDNF, NT3, CNTF, and BDNF, as well as cognate receptors thereof (including TrkB and TrkC). These factors may be obtained from R&D Systems, Inc. (Minneapolis, Minn.).

Additionally, the ATF5 inhibitor of the present invention may be an ATF5 transgene, comprising the ATF5 gene and an inducible promoter, in the absence of a suitable inducer. In a cell containing such a transgene, ATF5 expression would be sustained in the presence of a suitable inducing agent; however, ATF5 expression would be shut down once the supply of inducer was depleted. Thus, an ATF5 transgene, comprising the ATF5 gene and an inducible promoter, would, in the absence of a suitable inducer, effectively bring about a decrease in the amount or level of ATF5 in the cell, thereby functioning as an ATF5 inhibitor.

The ATF5 inhibitor of the present invention also may be an interfering RNA, or RNAi, including ATF5 small interfering RNA (51RNA), as disclosed herein. As used herein, "RNAi" refers to a double-stranded RNA (dsRNA) duplex of any length, with or without single-strand overhangs, wherein at least one strand, putatively the antisense strand, is homologous to the target mRNA to be degraded. As further used herein, a "double-stranded RNA" molecule includes any RNA molecule, fragment, or segment containing two strands forming an RNA duplex, notwithstanding the presence of single-stranded overhangs of unpaired nucleotides. Additionally, as used herein, a double-stranded RNA molecule includes single-stranded RNA molecules forming functional stem-loop structures, such that they thereby form the structural equivalent of an RNA duplex with single-strand overhangs. The double-stranded RNA molecule of the present invention may be very large, comprising thousands of nucleotides; preferably, however, it is small, in the range of 21-25 nucleotides. In a preferred embodiment, the RNAi of the present invention comprises a double-stranded RNA duplex of at least 19 nucleotides.

In one embodiment of the present invention, RNAi is produced in vivo by an expression vector containing a gene-silencing cassette coding for RNAi (see, e.g., U.S. Pat. No. 6,278,039, *C. elegans* deletion mutants; U.S. Patent Application No. 2002/0006664, Arrayed transfection method and uses related thereto; WO 99/32619, Genetic inhibition by double-stranded RNA; WO 01/29058, RNA interference pathway genes as tools for targeted genetic interference; WO 01/68836, Methods and compositions for RNA interference; and WO 01/96584, Materials and methods for the control of nematodes). In another embodiment of the present invention, RNAi is produced in vitro, synthetically or recombinantly, and transferred into the microorganism using standard molecular-biology techniques. Methods of making and transferring RNAi are well known in the art. See, e.g., Ashrafi et al., Genome-wide RNAi analysis of *Caenorhabditis elegans* fat regulatory genes. *Nature*, 421:268-72, 2003; Cottrell et al., Silence of the strands: RNA interference in eukaryotic pathogens. *Trends Microbiol.*, 11:37-43, 2003; Nikolaev et al., Parc. A Cytoplasmic Anchor for p53. Cell, 112:29-40, 2003; Wilda et al., Killing of leukemic cells with a BCR/ABL fusion gene RNA interference (RNAi). Oncogene, 21:5716-24, 2002; Escobar et al., RNAi-mediated oncogene silencing confers resistance to crown gall tumorigenesis. *Proc. Natl. Acad Sci. USA*, 98:13437-42, 2001; and Billy et al., Specific interference with gene expression induced by long, double-stranded RNA in mouse embryonal teratocarcinoma cell lines. *Proc. Natl. Acad Sci. USA*, 98:14428-33, 2001.

Furthermore, the ATF5 inhibitor of the present invention may be an oligonucleotide antisense to ATF5. Oligonucleotides antisense to ATF5 may be designed based on the nucleotide sequence of ATF5, which is readily available (FIG. 8). For example, a partial sequence of the ATF5 nucleotide sequence (generally, 18-20 base pairs), or a variation sequence thereof, may be selected for the design of an antisense oligonucleotide. This portion of the ATF5 nucleotide sequence may be within the 5' domain. A nucleotide sequence complementary to the selected partial sequence of the ATF5 gene, or the selected variation sequence, then may be chemically synthesized using one of a variety of techniques known to those skilled in the art, including, without limitation, automated synthesis of oligonucleotides having sequences which correspond to a partial sequence of the ATF5 nucleotide sequence, or a variation sequence thereof, using commercially-available oligonucleotide synthesizers, such as the Applied Biosystems Model 392 DNA/RNA synthesizer.

Once the desired antisense oligonucleotide has been prepared, its ability to inhibit ATF5 then may be assayed. For example, the oligonucleotide antisense to ATF5 may be contacted with neural progenitor cells, and the levels of ATF5 expression or activity in the cells may be determined using standard techniques, such as Western-blot analysis and immunostaining. Alternatively, the antisense oligonucleotide may be delivered to neural progenitor cells using a liposome vehicle, then the levels of ATF5 expression or activity in the cells may be determined using standard techniques, such as Western-blot analysis. Where the level of ATF5 expression in the cells is reduced in the presence of the designed antisense oligonucleotide, it may be concluded that the oligonucleotide could be a useful ATF5 inhibitor.

It is within the confines of the present invention that oligonucleotide antisense to ATF5 or ATF5 interfering RNA (e.g., siRNA) may be linked to another agent, such as a drug or a ribozyme, in order to increase the effectiveness of treatments using ATF5 inhibition, increase the efficacy of targeting, and/or increase the efficacy of degradation of ATF5 RNA. Examples of antineoplastic drugs to which the antisense oligonucleotide may be linked include, without limitation, carboplatin, cyclophosphamide, doxorubicin, etoposide, and vincristine. Moreover, oligonucleotide antisense to ATF5 may be prepared using modified bases (e.g., a phosphorothioate) to make the oligonucleotide more stable and better able to withstand degradation.

The ATF5 inhibitor of the present invention also may be a dominant-negative form of the protein (e.g., NTAzip-ATF5), as disclosed herein. In one embodiment, the dominant-negative form of ATF5 is expressed on an inducible promoter.

Additional ATF5 inhibitors may be identified using screening procedures well known in the art, and methods described below.

The present invention contemplates the use of proteins and protein analogues generated by synthesis of polypeptides in vitro, e.g., by chemical means or in vitro translation of mRNA. For example, ATF5 and inhibitors thereof may be synthesized by methods commonly known to one skilled in the art (*Modern Techniques of Peptide and Amino Acid Analysis* (New York: John Wiley & Sons, 1981); Bodansky, M., *Principles of Peptide Synthesis* (New York: Springer-Verlag New York, Inc., 1984). Examples of methods that may be employed in the synthesis of the amino acid sequences, and analogues of these sequences, include, but are not limited to, solid-phase peptide synthesis, solution-method peptide synthesis, and synthesis using any of the commercially-available peptide synthesizers. The amino acid sequences of the present invention may contain coupling agents and protecting groups, which are used in the synthesis of protein sequences, and which are well known to one of skill in the art.

A method of the present invention comprises inhibiting ATF5 in a stem cell or progenitor cell by contacting the cell with an ATF5 inhibitor. The inhibitor is provided in an amount effective to produce a differentiated cell. This amount may be readily determined by the skilled artisan, based upon known procedures and methods disclosed herein. The inventors have demonstrated herein that neurons cultured in the presence of neurotrophic factors survive and elaborate processes. Accordingly, in another embodiment, the method of the present invention further comprises the step of contacting a neural stem cell or neural progenitor cell with at least one neurotrophic factor, contemporaneously with, or following, inhibition of ATF5. The neurotrophic factors of the present invention are provided in amounts effective to produce a fully-differentiated neural cell of the CNS or PNS (e.g., a neuron). These amounts may be readily determined by the skilled artisan, based upon known procedures and methods disclosed herein.

In the method of the present invention, neural stem cells or neural progenitor cells may be contacted with effective amounts of an ATF5 inhibitor and neurotrophic factors in vitro, or in vivo in a subject. The inhibitor and factors may be contacted with a neural stem cell or neural progenitor cell by introducing the inhibitor and factors into the cell. Where contacting is effected in vitro, the inhibitor and factors may be added directly to the culture medium, as described herein. Alternatively, the inhibitor and factors may be contacted with a neural stem cell or neural progenitor cell in vivo in a subject, by introducing the inhibitor and factors into the subject (e.g., by introducing the inhibitor and factors into cells of the subject), or by administering the inhibitor and factors to the subject. The subject may be any neural or developed animal, but is preferably a mammal (e.g., a human, domestic animal, or commercial animal). More preferably, the subject is a human.

Where the inhibitor and factors are contacted with the cell in vivo, the subject is preferably an embryo. However, it is within the confines of the present invention for the cells to be transplanted into a fully-grown human or animal subject, and for the inhibitor and factors then to be administered to the human in order to effect differentiation of the neural stem cells or neural progenitor cells into differentiated neural cells in vivo in the subject. The cells may be contained in nervous tissue of a subject, and may be detected in nervous tissue of the subject by standard detection methods readily determined from the known art, examples of which include, without limitation, immunological techniques (e.g., immunohistochemical staining), fluorescence imaging techniques, and microscopic techniques.

The inhibitor and factors of the present invention may be contacted with neural stem cells or neural progenitor cells, either in vitro or in vivo in a subject, by known techniques used for the introduction and administration of proteins, nucleic acids, and other drugs. Examples of methods for contacting the cells with (i.e., treating the cells with) an ATF5 inhibitor or a neurotrophic factor (in protein or nucleic acid form) include, without limitation, absorption, electroporation, immersion, injection, introduction, liposome delivery, transfection, transfusion, vectors, and other protein-delivery and nucleic-acid-delivery vehicles and methods. When target cells are localized to a particular portion of a subject, it may be desirable to introduce the inhibitor and factors directly to the cells, by injection or by some other means (e.g., by introducing the inhibitor and factors into the blood or another body fluid).

Where the inhibitor or neurotrophic factor is a protein or other molecule, it may be introduced into a neural stem cell or neural progenitor cell directly, in accordance with conventional techniques and methods disclosed herein. Additionally, a protein inhibitor or factor may be introduced into a neural stem cell or neural progenitor cell indirectly, by introducing into the cell a nucleic acid encoding the inhibitor or factor, in a manner permitting expression of the protein inhibitor or factor. The inhibitor or factor may be introduced into neural stem cells or neural progenitor cells, in vitro or in vivo, using conventional procedures known in the art, including, without limitation, electroporation, DEAE Dextran transfection, calcium phosphate transfection, monocationic liposome fusion, polycationic liposome fusion, protoplast fusion, creation of an in vivo electrical field, DNA-coated microprojectile bombardment, injection with recombinant replication-defective viruses, homologous recombination, in vivo gene therapy, ex vivo gene therapy, viral vectors, and naked DNA transfer, or any combination thereof. Recombinant viral vectors suitable for gene therapy include, but are not limited to, vectors derived from the genomes of such viruses as retrovirus, HSV, adenovirus, adeno-associated virus, Semiliki Forest virus, cytomegalovirus, lentivirus, and vaccinia virus. The amount of nucleic acid to be used is an amount sufficient to express an amount of protein effective to produce a differentiated neural cell. These amounts may be readily determined by the skilled artisan. It is also within the confines of the present invention that a nucleic acid encoding a protein inhibitor or factor may be introduced into suitable neural stem cells or neural progenitor cells in vitro, using conventional procedures, to achieve expression of the protein inhibitor or factor in the cells. Cells expressing protein inhibitor or factor then may be introduced into a subject to produce a differentiated neural cell in vivo.

In accordance with the method of the present invention, ATF5 inhibitors and neurotrophic factors may be administered to a human or animal subject by known procedures, including, without limitation, oral administration, parenteral administration, and transdermal administration. Preferably, the inhibitors or factors are administered parenterally, by intracranial, intraspinal, intrathecal, or subcutaneous injection. The inhibitors and factors of the present invention also may be administered to a subject in accordance with any of the above-described methods for effecting in vivo contact between neural stem cells/neural progenitor cells and ATF5 inhibitors/neurotrophic factors.

For oral administration, an inhibitor or factor formulation may be presented as capsules, tablets, powders, granules, or as a suspension. The formulation may have conventional additives, such as lactose, mannitol, corn starch, or potato starch. The formulation also may be presented with binders, such as crystalline cellulose, cellulose derivatives, acacia, corn starch, or gelatins. Additionally, the formulation may be presented with disintegrators, such as corn starch, potato starch, or sodium carboxymethylcellulose. The formulation also may be presented with dibasic calcium phosphate anhydrous or sodium starch glycolate. Finally, the formulation may be presented with lubricants, such as talc or magnesium stearate.

For parenteral administration (i.e., administration by injection through a route other than the alimentary canal), an inhibitor or factor may be combined with a sterile aqueous solution that is preferably isotonic with the blood of the subject. Such a formulation may be prepared by dissolving a solid active ingredient in water containing physiologically-compatible substances, such as sodium chloride, glycine, and the like, and having a buffered pH compatible with physiological conditions, so as to produce an aqueous solution, then rendering said solution sterile. The formulation may be presented in unit or multi-dose containers, such as sealed ampoules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual.

For transdermal administration, an inhibitor or factor may be combined with skin penetration enhancers, such as propylene glycol, polyethylene glycol, isopropanol, ethanol, oleic acid, N-methylpyrrolidone, and the like, which increase the permeability of the skin to the inhibitor or factor, and permit the inhibitor or factor to penetrate through the skin and into the bloodstream. The inhibitor/enhancer or factor/enhancer compositions also may be further combined with a polymeric substance, such as ethylcellulose, hydroxypropyl cellulose, ethylene/vinylacetate, polyvinyl pyrrolidone, and the like, to provide the composition in gel form, which may be dissolved in solvent, such as methylene chloride, evaporated to the desired viscosity, and then applied to backing material to provide a patch.

The present invention provides a method for promoting differentiation of neural stem cells or neural progenitor cells into differentiated neural cells, and for purifying and isolating the neural cells so generated using enhanced green fluorescent protein (eGFP) as a genetic marker. The method described herein for promoting differentiation of neural stem cells or neural progenitor cells in vitro provides a source of neurons, or other neural cells of the CNS or PNS, that are available for transplant into a subject. Thus, this method is particularly useful for producing neural cells for use in treating conditions associated with nervous tissue degeneration.

The term "nervous tissue", as used herein, refers to tissue of the nervous system, which includes the differentiated neural cells of the present invention and progenitors thereof. As further used herein, "nervous tissue degeneration" means a condition of deterioration of nervous tissue, wherein the nervous tissue changes to a lower or less functionally-active form. It is believed that, by promoting differentiation of neural stem cells or neural progenitor cells, the method described herein will be useful in repopulating various injured and/or degenerated nervous tissues in a subject, through production of differentiated neural cells and subsequent transplant thereof into a subject in need of such transplantation.

Accordingly, the present invention provides a method for treating nervous tissue degeneration in a subject in need of treatment for nervous tissue degeneration, comprising promoting differentiation of neural stem cells or neural progenitor cells into differentiated neural cells, in accordance with the methods described herein, and transplanting the differentiated neural cells into the subject, thereby treating the nervous tissue degeneration. By way of example, the method of the present invention may comprise the following steps: (a) obtaining or generating a culture of neural stem cells or neural progenitor cells; (b) contacting the culture of neural stem cells or neural progenitor cells with an amount of an ATF5 inhibitor effective to produce differentiated neural cells; (c) optionally, contacting the differentiated neural cells with at least one neurotrophic factor; and (d) transplanting the differentiated neural cells into the subject, in an amount effective to treat the nervous tissue degeneration. In one embodiment of the invention, the subject is an embryo. In another embodiment of the invention, the subject is a human. Preferably, the subject has nervous tissue degeneration.

Nervous tissue degeneration may arise in the CNS or PNS, and may be caused by, or associated with, a variety of disorders, conditions, and factors, including, without limitation, primary neurologic conditions (e.g., neurodegenerative diseases), demyelinating conditions, CNS and PNS traumas and injuries, and acquired secondary effects of non-neural dysfunction (e.g., neural loss secondary to degenerative, pathologic, or traumatic events). Examples of CNS traumas include, without limitation, blunt trauma, hypoxia, and invasive trauma. Examples of acquired secondary effects of non-neural dysfunction include, without limitation, cerebral palsy, congenital hydrocephalus, muscular dystrophy, stroke, and vascular dementia, as well as neural degeneration resulting from any of the following: an injury associated with cerebral hemorrhage, developmental disorders (e.g., a defect of the brain, such as congenital hydrocephalus, or a defect of the spinal cord, such as spina bifida), diabetic encephalopathy, hypertensive encephalopathy, intracranial aneurysms, ischemia, kidney dysfunction, subarachnoid hemorrhage, trauma to the brain and spinal cord, treatment by such therapeutic agents as chemotherapy agents and antiviral agents, vascular lesions of the brain and spinal cord, and other diseases or conditions prone to result in nervous tissue degeneration.

In one embodiment of the present invention, the nervous tissue degeneration is a peripheral neuropathy in the PNS. As defined herein, the term "peripheral neuropathy" refers to a syndrome of sensory loss, muscle weakness, muscle atrophy, decreased deep-tendon reflexes, and/or vasomotor symptoms. In a subject who has a peripheral neuropathy, myelin sheaths (or Schwann cells) may be primarily affected, or axons may be primarily affected. The peripheral neuropathy may affect a single nerve (mononeuropathy), two or more nerves in separate areas (multiple mononeuropathy), or many nerves simultaneously (polyneuropathy).

Examples of peripheral neuropathies that may be treated by the methods disclosed herein include, without limitation, peripheral neuropathies associated with acute or chronic inflammatory polyneuropathy, amyotrophic lateral sclerosis (ALS), collagen vascular disorder (e.g., polyarteritis nodosa, rheumatoid arthritis, Sjögren's syndrome, or systemic lupus erythematosus), diphtheria, Guillain-Barré syndrome, hereditary peripheral neuropathy (e.g., Charcot-Marie-Tooth disease (including type I, type II, and all subtypes), hereditary motor and sensory neuropathy (types I, II, and III, and peroneal muscular atrophy), hereditary neuropathy with liability to pressure palsy (HNPP), infectious disease (e.g., acquired immune deficiency syndrome (AIDS)), Lyme disease (e.g., infection with *Borrelia burgdorferi*), invasion of a microorganism (e.g., leprosy—the leading cause of peripheral neuropathy worldwide, after neural trauma), leukodystrophy, metabolic disease or disorder (e.g., amyloidosis, diabetes mellitus, hypothyroidism, porphyria, sarcoidosis, or uremia), neurofibromatosis, nutritional deficiencies, paraneoplastic disease, peroneal nerve palsy, polio, porphyria, postpolio syndrome, Proteus syndrome, pressure paralysis (e.g., carpal tunnel syndrome), progressive bulbar palsy, radial nerve palsy, spinal muscular atrophy (SMA), a toxic agent (e.g., barbital, carbon monoxide, chlorobutanol, dapsone, emetine, heavy metals, hexobarbital, lead, nitrofurantoin, orthodinitrophenal, phenytoin, pyridoxine, sulfonamides, triorthocresyl phosphate, the vinca alkaloids, many solvents, other industrial poisons, and certain AIDS drugs (including didanosine and zalcitabine), trauma (including neural trauma—the leading cause of peripheral neuropathy, worldwide), and ulnar nerve palsy (Beers and Berkow, eds., *The Merck Manual of Diagnosis and Therapy*, 17$^{th}$ ed. (Whitehouse Station, N.J.: Merck Research Laboratories, 1999) chap. 183). In a preferred embodiment of the present invention, the peripheral neuropathy is ALS or SMA.

In another embodiment of the present invention, the nervous tissue degeneration is a neurodegenerative disease. Examples of neurodegenerative diseases that may be treated by the methods disclosed herein include, without limitation, Alzheimer's disease, amyotrophic lateral sclerosis (Lou Gehrig's Disease), Binswanger's disease, Huntington's chorea, multiple sclerosis, myasthenia gravis, Parkinson's disease, and Pick's disease.

It is also within the confines of the present invention for the method described herein to be used to treat nervous tissue degeneration that is associated with a demyelinating condition. Demyelinating conditions are manifested in loss of myelin—the multiple dense layers of lipids and protein which cover many nerve fibers. These layers are provided by oligodendroglia in the CNS, and Schwann cells in the PNS. In patients with demyelinating conditions, demyelination may be irreversible; it is usually accompanied or followed by axonal degeneration, and often by cellular degeneration. Demyelination can occur as a result of neuronal damage or damage to the myelin itself—whether due to aberrant immune responses, local injury, ischemia, metabolic disorders, toxic agents, or viral infections.

Central demyelination (demyelination of the CNS) occurs in several conditions, often of uncertain etiology, that have come to be known as the primary demyelinating diseases. Of these, multiple sclerosis is the most prevalent. Other primary demyelinating diseases include adrenoleukodystrophy (ALD), adrenomyeloneuropathy, AIDS-vacuolar myelopathy, HTLV-associated myelopathy, Leber's hereditary optic atrophy, progressive multifocal leukoencephalopathy (PML), subacute sclerosing panencephalitis, and tropical spastic paraparesis. In addition, there are acute conditions in which demyelination can occur in the CNS, e.g., acute disseminated encephalomyelitis (ADEM) and acute viral encephalitis. Furthermore, acute transverse myelitis, a syndrome in which an acute spinal cord transection of unknown cause affects both gray and white matter in one or more adjacent thoracic segments, can also result in demyelination. Finally, there are animal models which mimic features of human demyelinating diseases. Examples include experimental autoimmune neuritis (EAN), demyelination induced by Theiler's virus, and experimental autoimmune encephalomyelitis (EAE)—an autoimmune disease which is experimentally induced in a variety of species and which resembles MS in its clinical and neuropathological aspects.

The differentiated neural cells of the present invention may be transplanted into a subject in need of treatment by standard procedures known in the art, as well as the methods described herein. By way of example, neural stem cells or neural progenitor cells may be induced with an ATF5 inhibitor, to produce differentiated neural cells. At an appropriate time post-induction (e.g., 3-4 days after induction), the cells may be prepared for transplantation (e.g., partially triturated), and then transplanted into a subject (e.g., into the spinal cord of a chick, HH stage 15-17). To accommodate transplanted tissue, the subject may be suction-lesioned prior to implantation. In one embodiment of the present invention, the differentiated neural cells are transplanted into the spinal cord of a subject, thereby repopulating the subject's spinal cord, and the nervous tissue degeneration is a peripheral neuropathy associated with ALS or SMA.

In another embodiment of the present invention, the neural stem cells or neural progenitor cells contain an ATF5 transgene that has been engineered to express ATF5 on an inducible promoter. In this embodiment of the present invention, ATF5 may be expressed in the presence of a suitable inducing agent, thereby permitting propagation of the neural stem cells or neural progenitor cells in vitro. Once the cells are transplanted into the subject, however, the inducing agent would be withdrawn, resulting in decreased ATF5 expression, and thereby promoting differentiation of the transplanted cells. Expression of ATF5 would be sustained in the presence of the inducer, and would be shut down once the supply of inducer was depleted (e.g., upon transplant into a subject).

In an alternative embodiment, a dominant-negative form of ATF5 (an ATF5 inhibitor) may be introduced into the neural stem cells or neural progenitor cells on an inducible promoter. The transgene could be maintained in an uninduced state in vitro, permitting propagation of the cells, and then induced with a suitable inducing agent, in vivo in a subject, thereby promoting differentiation of the neural stem cells or neural progenitor cells.

In the method of the present invention, the differentiated neural cells are transplanted into a subject in need of treatment in an amount effective to treat the nervous tissue degeneration. As used herein, the phrase "effective to treat the nervous tissue degeneration" effective to ameliorate or minimize the clinical impairment or symptoms of the nervous tissue degeneration. For example, where the nervous tissue degeneration is a peripheral neuropathy, the clinical impairment or symptoms of the peripheral neuropathy may be ameliorated or minimized by alleviating vasomotor symptoms, increasing deep-tendon reflexes, reducing muscle atrophy, restoring sensory function, and strengthening muscles. The amount of differentiated neural cells effective to treat nervous tissue degeneration in a subject in need of treatment will vary depending upon the particular factors of each case, including the type of nervous tissue degeneration, the stage of the nervous tissue degeneration, the subject's weight, the severity of the subject's condition, the type of differentiated neural cells, and the method of transplantation. This amount may be readily determined by the skilled artisan, based upon known procedures, including clinical trials, and methods disclosed herein.

In view of the above-described method for promoting differentiation of neural stem cells and neural progenitor cells into differentiated neural cells, the present invention further provides a method for producing differentiated neural cells, comprising the steps of: (a) obtaining or generating a culture of neural stem cells or neural progenitor cells; (b) contacting the culture of neural stem cells or neural progenitor cells with an amount of an ATF5 inhibitor effective to produce a subclass of differentiated neural cells; and (c) optionally, contacting the differentiated neural cells with at least one neurotrophic factor. The present invention also provides a population of cells, comprising the differentiated neural cells produced by this method. In one embodiment, some or all of the cells express eGFP.

In the method of the present invention, any of steps (b)-(c) may be performed in vitro, or in vivo in a subject. Following any in vitro steps, cells may be transplanted into a subject such that the remaining steps are performed in vivo. Accordingly, the method of the present invention further comprises the step of transplanting the neural progenitor cells or the differentiated neural cells into a subject. For example, the neural stem cells or neural progenitor cells may contain an ATF5 transgene that has been engineered to express ATF5 on an inducible promoter. In this embodiment of the present invention, ATF5 would be expressed in the presence of a suitable inducing agent, thereby permitting propagation of the neural stem cells or neural progenitor cells in vitro. Thereafter, the cells may be transplanted into a subject, such that steps (b) and (c) are carried out in vivo. Because the inducing agent would be withdrawn upon transplantation of the cells into the subject, ATF5 expression would be decreased, thereby promoting differentiation of the transplanted cells. Similarly, a culture of neural stem cells or neural progenitor cells may be contacted with an ATF5 inhibitor in vitro, to produce differentiated neural cells. The neural cells so produced then may be transplanted into a subject, such that step (c) is carried out in vivo. In an alternative method, a culture of neural stem cells or neural progenitor cells may be contacted with an ATF5 inhibitor in vitro, to produce differentiated neural cells; and, optionally, the differentiated neural cells may be contacted with at least one neurotrophic factor in vitro. The differentiated neural cells then may be transplanted into a subject. In one embodiment of the present invention, the neurons are transplanted into the spinal cord of the subject.

Because the selective degeneration of specific classes of CNS neurons underlies many neurological disorders, research into the growth, survival, and activity of neurons remains a priority. Unfortunately, however, live neurons are not readily available for such studies. For this reason, the present invention will be of particular importance to researchers in the fields of neuroscience and neurology, as it provides a potentially-unlimited source of neural cells to be studied. Accordingly, the present invention also provides for uses of the above-described neural progenitor cells and differentiated neural cells in particular areas of research.

The neural progenitor cells and differentiated neural cells of the present invention will be useful in the analysis of neuron development, function, and death—research which is critical to a complete understanding of neurological diseases. Furthermore, the neural progenitor cells and differentiated neural cells of the present invention will be useful in monitoring synaptic differentiation at sites of contact with target muscles. Finally, the neural progenitor cells and differentiated neural cells of the present invention will facilitate a direct comparison of normal, healthy neurons with degenerated neurons. For such a comparison, both the healthy and the diseased neural cells may be produced using well-known techniques and methods described herein.

The present invention further provides a method for isolating a pure population of differentiated neural cells and/or purifying a population of differentiated neural cells, comprising the steps of: (a) obtaining or generating a culture of neural stem cells or neural progenitor cells that express enhanced green fluorescent protein (eGFP); (b) contacting the culture of neural stem cells or neural progenitor cells with an amount of an ATF5 inhibitor effective to produce differentiated neural cells, wherein some or all of the differentiated neural cells also express eGFP; (c) optionally, contacting the differentiated neural cells with at least one neurotrophic factor; (d) detecting expression of eGFP in the differentiated neural cells; and (e) isolating the differentiated neural cells that express eGFP. Neural stem cells or neural progenitor cells that express eGFP may be made in accordance with methods disclosed herein.

According to the method of the present invention, expression of eGFP may be detected in differentiated neural cells by either in vitro or in vivo assay. As used herein, "expression" refers to the transcription of the eGFP gene into at least one mRNA transcript, or the translation of at least one mRNA into an eGFP protein. The differentiated neural cells may be assayed for eGFP expression by assaying for eGFP protein, eGFP cDNA, or eGFP mRNA. The appropriate form of eGFP will be apparent based on the particular techniques discussed herein.

Differentiated neural cells may be assayed for eGFP expression, and eGFP expression may be detected in differentiated neural cells, using assays and detection methods well known in the art. Because eGFP provides a non-invasive marker for labeling cells in culture and in vivo, expression of eGFP is preferably detected in differentiated neural cells using various imaging techniques such as phase, and fluorescence imaging techniques, as disclosed herein. Differentiated neural cells expressing high levels of eGFP then may be isolated from a cell suspension by sorting (e.g., by FACS sorting, using a Beckman-Coulter Altra flow cytometer), based upon their eGFP fluorescence and forward light scatter, as described below.

Other methods also may be used to detect eGFP expression in the differentiated neural cells of the present invention. Examples of such detection methods include, without limitation, hybridization analysis, imaging techniques, immunological techniques, immunoprecipitation, radiation detection, Western-blot analysis, and any additional assays or detection methods disclosed herein. For example, differentiated neural cells may be assayed for eGFP expression using an agent reactive with eGFP protein or eGFP nucleic acid. As used herein, "reactive" means the agent has affinity for, binds to, or is directed against eGFP. As further used herein, an "agent" shall include a protein, polypeptide, peptide, nucleic acid (including DNA or RNA), antibody, Fab fragment, $F(ab')_2$ fragment, molecule, compound, antibiotic, drug, and any combinations thereof. In one embodiment of the present invention, the agent reactive with eGFP is an antibody (e.g., αGFP (Molecular Probes, Inc., Eugene, Oreg.; BD Biosciences Clontech, Palo Alto, Calif.)).

Following detection of eGFP expression in differentiated neural cells, the extent of eGFP expression in the cells may be measured or quantified, if desired, using one of various quantification assays. Such assays are well known to one of skill in the art, and may include immunohistochemistry, immunocytochemistry, flow cytometry, mass spectroscopy, Western-blot analysis, or an ELISA for measuring amounts of eGFP protein.

The present invention further provides a method for identifying an agent for use in treating a condition associated with nervous tissue degeneration, as defined above. Examples of conditions associated with nervous tissue degeneration include peripheral neuropathies, demyelinating conditions, and the primary neurologic conditions (e.g., neurodegenerative diseases), CNS and PNS traumas and injuries, and acquired secondary effects of non-neural dysfunction (e.g., neural loss secondary to degenerative, pathologic, or traumatic events) described herein.

The method of the present invention comprises the steps of: (a) obtaining or generating a culture of neural stem cells or neural progenitor cells; (b) contacting the culture of cells with an amount of an ATF5 inhibitor effective to produce neurons, wherein some or all of the neurons are degenerated; (c) contacting the degenerated neurons with a candidate agent; and (d) determining if the agent enhances regeneration or survival of some or all of the degenerated neurons. As used herein, the term "enhance regeneration" means augment, improve, or increase partial or full growth (or regrowth) of a neuron (including neurites and the myelin sheath) that has degenerated. As further used herein, the term "growth" refers to an increase in diameter, length, mass, and/or thickness of a neuron (including neurites and the myelin sheath). Regeneration of the neuron may take place in neurons of both the central nervous system and the peripheral nervous system. Additionally, as used herein, the term "enhance survival" of a neuron means increasing the duration of the neuron's viable lifespan, either in vitro or in vivo. In one embodiment of the present invention, the agent enhances regeneration or survival of degenerated motor neurons.

In the method of the present invention, degenerated neurons may be contacted with a candidate agent by any of the methods of effecting contact between inhibitors or factors or agents and cells, and any modes of introduction and administration, described herein. Regeneration, and enhanced regeneration, of neurons may be measured or detected by known procedures, including Western blotting for myelin-specific and axon-specific proteins, electron microscopy in conjunction with morphometry, and any of the methods, molecular procedures, and assays known to one of skill in the art. In addition, growth of myelin may be assayed using the g-ratio—one measure of the integrity of the axon:myelin association. The g-ratio is defined as the axonal diameter divided by the total diameter of the axon and myelin. This ratio provides a reliable measure of relative myelination for an axon of any given size (Bieri et al., Abnormal nerve conduction studies in mice expressing a mutant form of the POU transcription factor, SCIP. *J. Neurosci. Res.*, 50:821-28, 1997). Numerous studies have documented that a g-ratio of 0.6 is normal for most fibers (Waxman and Bennett, Relative conduction velocities of small myelinated and nonmyelinated fibres in the central nervous system. *Nature New Biol.*, 238: 217, 1972). In one embodiment of the present invention, the degenerated neurons express enhanced green fluorescent protein (eGFP). It is expected that such neurons will allow for inhibited high-throughput drug screening.

The inventors have demonstrated herein that neuronal differentiation may be induced by CRE-mediated gene activation, and that such activation is repressed in neural progenitor cells by factors such as ATF5. Accordingly, the present invention further provides a method for suppressing differentiation of neural stem cells or neural progenitor cells into differentiated neural cells, where such cells might otherwise be determined to differentiate. The method of the present invention comprises contacting the neural stem cells or neural progenitor cells with an amount of ATF5, or a peptidomimetic thereof, effective to suppress differentiation in the neural stem cells or neural progenitor cells. This method will permit a pool of these undifferentiated cells to be generated under conditions in which they might otherwise differentiate and cease proliferation. The ATF5 or mimetic may be in the form of a protein, or a nucleic acid encoding the protein, and may be contacted with the cells in accordance with methods previously described.

The present invention also provides therapeutic compositions, comprising a nucleic acid encoding an ATF5 inhibitor, a vector, and, optionally, a pharmaceutically-acceptable carrier. The pharmaceutically-acceptable carrier must be "acceptable" in the sense of being compatible with the other ingredients of the composition, and not deleterious to the recipient thereof. The pharmaceutically-acceptable carrier employed herein is selected from various organic or inorganic materials that are used as materials for pharmaceutical formulations, and which may be incorporated as analgesic agents, buffers, binders, disintegrants, diluents, emulsifiers, excipients, extenders, glidants, solubilizers, stabilizers, suspending agents, tonicity agents, vehicles, and viscosity-increasing agents. If necessary, pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc, and water, among others.

The formulations of the present invention may be prepared by methods well-known in the pharmaceutical arts. For example, the ATF5 inhibitor protein or nucleic acid may be brought into association with a carrier or diluent, as a suspension or solution. Optionally, one or more accessory ingredients (e.g., buffers, flavoring agents, surface active agents, and the like) also may be added. The choice of carrier will depend upon the route of administration. The pharmaceutical composition would be useful for administering the ATF5 inhibitor of the present invention to a subject to treat a neural tumor, as discussed below. The ATF5 inhibitor is provided in an amount that is effective to treat the neural tumor in a subject to whom the pharmaceutical composition is administered. That amount may be readily determined by the skilled artisan, as described above.

As disclosed herein, the inventors have determined that ATF5 expression is elevated in neural and other tumor types, including but not limited to breast, ovary, endometrium, gastric, colon, liver, pancrease, kidney, bladder, prostate, testis, skin, esophagus, tongue, mouth, parotid, larynx, pharynx, lymph node, lung, and brain tumors. The inventors have also demonstrated for the first time that interfering with the function or expression of ATF5 promotes apoptosis of glioblastoma multiforme tumors in vitro and in vivo. Additionally, the inventors have shown for the first time that selective interference with ATF5 function in other carcinoma types, e.g., breast tumors, also triggers cell death. Therefore, the pharmaceutical composition of the present invention may be useful for treating a neural tumor in a subject. As used herein, the term "tumor" refers to a pathologic proliferation of cells, and includes a neoplasia. The term "neoplasia", and related terms as further used herein, refers to the uncontrolled and progressive multiplication of tumor cells under conditions that would not elicit, or would cause cessation of, multiplication of normal cells. Neoplasia results in the formation of a "neoplasm", which is defined herein to mean any new and abnormal growth, particularly a new growth of tissue, in which the growth of cells is uncontrolled and progressive. As used herein, neoplasms include, without limitation, morphological irregularities in cells in tissue of a subject, as well as pathologic proliferation of cells in tissue of a subject, as compared with normal proliferation in the same type of tissue. Additionally, neoplasms include benign tumors and malignant tumors. Malignant neoplasms are distinguished from benign in that the former show a greater degree of anaplasia, or loss of differentiation and orientation of cells, and have the properties of invasion and metastasis. Thus, neoplasia includes "cancer", which herein refers to a proliferation of tumor cells having the unique trait of loss of normal controls, resulting in unregulated growth, lack of differentiation, local tissue invasion, and metastasis.

Additionally, as used herein, the term "neural tumor" refers to a tumorigenic form of neural cells (i.e., transformed neural cells), and includes astrocytoma cells (i.e., cells of all astrocytomas, including, without limitation, Grades I-IV astrocytomas, anaplastic astrocytoma, astroblastoma, astrocytoma fibrillare, astrocytoma protoplasmaticum, gemistocytic astrocytoma, and glioblastoma multiforme), gliomas, medulloblastomas, neuroblastomas, and other brain tumors. Brain tumors invade and destroy normal tissue, producing such effects as impaired sensorimotor and cognitive function, increased intracranial pressure, cerebral edema, and compression of brain tissue, cranial nerves, and cerebral vessels. Metastases may involve the skull or any intracranial structure. The size, location, rate of growth, and histologic grade of malignancy determine the seriousness of brain tumors. Non-malignant tumors grow slowly, with few mitoses, no necrosis, and no vascular proliferation. Malignant tumors grow more rapidly, and invade other tissues. However, they rarely spread beyond the CNS, because they cause death by local growth. Drowsiness, lethargy, obtuseness, personality changes, disordered conduct, and impaired mental faculties are the initial symptoms in 25% of patients with malignant brain tumors.

Brain tumors may be classified by site (e.g., brain stem, cerebellum, cerebrum, cranial nerves, ependyma, meninges, neuroglia, pineal region, pituitary gland, and skull) or by histologic type (e.g., meningioma, primary CNS lymphoma, or astrocytoma). Common primary childhood tumors are cerebellar astrocytomas and medulloblastomas, ependymomas, gliomas of the brain stem, neuroblastomas, and congenital tumors. In adults, primary tumors include meningiomas, schwannomas, and gliomas of the cerebral hemispheres (particularly the malignant glioblastoma multiforme and anaplastic astrocytoma, and the more benign astrocytoma and oligodendroglioma). Overall incidence of intracranial neoplasms is essentially equal in males and females, but cerebellar medulloblastoma and glioblastoma multiforme are more common in males.

Gliomas are tumors composed of tissue representing neuroglia in any one of its stages of development. They account for 45% of intracranial tumors. Gliomas can encompass all of the primary intrinsic neoplasms of the brain and spinal cord, including astrocytomas, ependymomas, and neurocytomas. Astrocytomas are tumors composed of transformed astrocytes, or astrocytic tumor cells. Such tumors have been classified in order of increasing malignancy: Grade I consists of fibrillary or protoplasmic astrocytes; Grade II is an astroblastoma, consisting of cells with abundant cytoplasm and two or three nuclei; and Grades III and IV are forms of glioblastoma multiforme, a rapidly growing tumor that is usually confined to the cerebral hemispheres and composed of a mixture of astrocytes, spongioblasts, astroblasts, and other astrocytic tumor cells. Astrocytoma, a primary CNS tumor, is frequently found in the brain stem, cerebellum, and cerebrum. Anaplastic astrocytoma and glioblastoma multiforme are commonly located in the cerebrum.

The present invention additionally provides methods for promoting apoptosis in a neoplastic cell comprising contacting the neoplastic cell with an ATF5 inhibitor. The neoplastic cell can be selected from the group consisting of: breast, ovary, endometrium, gastric, colon, liver, pancrease, kidney, bladder, prostate, testis, skin, esophagus, tongue, mouth, parotid, larynx, pharynx, lymph node, lung, and brain. In one embodiment, the neoplastic cell is selected from the group consisting of glioblastoma, astrocytoma, glioma, medulloblastoma and neuroblastoma. In other embodiments, the ATF5 inhibitor is a nucleic acid, which can include, but is not limited to a dominant negative form of ATF5 (e.g. NTAzip-ATF5), or ATF5siRNA. The method of the present invention can be performed in vitro as well as in vivo in a subject. As used herein, "apoptosis" refers to cell death which is wholly or partially genetically controlled.

In view of the foregoing, the present invention further provides a method for treating or preventing a tumor in a subject in need of treatment, comprising administering to the subject a pharmaceutical composition comprising an ATF5 inhibitor and, optionally, a pharmaceutically-acceptable carrier. The ATF5 inhibitor is provided in an amount that is effective to treat the tumor in a subject to whom the composition is administered. As used herein, the phrase "effective" means effective to ameliorate or minimize the clinical impairment or symptoms of the tumor. For example, the clinical impairment or symptoms of the tumor may be ameliorated or minimized by diminishing any pain or discomfort suffered by the subject; by extending the survival of the subject beyond that which would otherwise be expected in the absence of such treatment; by inhibiting or preventing the development or spread of the tumor; or by limiting, suspending, terminating, or otherwise controlling the maturation and proliferation of cells in the tumor. The amount of ATF5 inhibitor effective to treat a tumor in a subject in need of treatment will vary depending upon the particular factors of each case, including the type of tumor, the stage of the tumor, the subject's weight, the severity of the subject's condition, and the method of administration. This amount can be readily determined by the skilled artisan. In one embodiment of the present invention, the pharmaceutical composition comprises a nucleic acid encoding an ATF5 inhibitor, a viral vector, and, optionally, a pharmaceutically-acceptable carrier.

As disclosed herein, according to one proposed pathway, ATF5 binding to CRE DNA-binding sites suppresses differentiation of neural stem cells and neural progenitor cells into differentiated neural cells. Thus, effective ATF5 inhibitors can be designed to replace CRE in its interaction with ATF5. A candidate agent having the ability to bind ATF5 may, as a consequence of this binding, prevent ATF5 binding to CRE through steric hindrance. According to other proposed pathways, ATF5 may act by affecting additional classes of transcription binding sites on DNA. Accordingly, effective ATF5 inhibitors can also be designed to replace these additional binding sites. A candidate agent having the ability to bind ATF5 may, as a consequence of this binding, prevent ATF5 binding to these additional DNA binding sites through steric hindrance.

Accordingly, the present invention also provides a method for identifying an agent that inhibits ATF5, by assessing the ability of a candidate agent to inhibit interaction between ATF5 and CRE. The method of the present invention comprises the steps of: (a) contacting a candidate agent with ATF5, in the presence of CRE; and (b) assessing the ability of the candidate agent to inhibit interaction between ATF5 and CRE. An agent that inhibits interaction between ATF5 and CRE may be either natural or synthetic, and may be an agent reactive with ATF5 (i.e., has affinity for, binds to, or is directed against ATF5). An agent that is reactive with ATF5, as disclosed herein, may have the ability to inhibit interaction between ATF5 and CRE by binding to ATF5. A candidate agent having the ability to bind to ATF5 may, as a consequence of this binding, inhibit ATF5 activity through steric interactions (without binding to CRE itself). A CRE-luciferase reporter assay may be used to gauge such interactions, as described herein (Example 11).

In accordance with the method of the present invention, a CRE-like agent that binds ATF5 may be identified using an in vitro assay (e.g., a direct binding assay, competitive binding assay, etc.). In a direct binding assay, for example, the binding of a candidate agent to ATF5 or a peptide fragment thereof may be measured directly. A candidate agent may be supplied by a peptide library, for example. Alternatively, in a competitive binding assay, standard methodologies may be used in order to assess the ability of a candidate agent to bind ATF5, and thereby inhibit CRE-ATF5 interaction. In such a competitive binding assay, the candidate agent competes with CRE for binding to ATF5 (but does not bind directly to CRE). Once bound to ATF5, the candidate agent could sterically hinder binding of CRE to ATF5, thereby preventing interaction between CRE and ATF5. A competitive binding assay represents a convenient way to assess inhibition of CRE-ATF5 interaction, since it allows the use of crude extracts containing ATF5 and CRE.

A competitive binding assay may be carried out by adding ATF5, or an extract containing ATF5 biological activity (as defined above), to a mixture containing the candidate agent and labeled CRE, both of which are present in the mixture in known concentrations. After incubation, the ATF5-agent complex may be separated from the unbound labeled CRE and unlabeled candidate agent, and counted. The concentration of the candidate agent required to inhibit 50% of the binding of the labeled CRE to ATF5 ($IC_{50}$) then may be calculated.

The binding assay formats described herein employ labeled assay components. Labeling of CRE or ATF5 may be accomplished using one of a variety of different chemiluminescent and radioactive labels known in the art. The label of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the label may be a radioactive marker, including, for example, a radioisotope. The radioisotope may be any isotope that emits detectable radiation, including, without limitation, $^{35}S$, $^{32}P$, $^{125}I$, $^{3}H$, or $^{14}C$. The label may also be luciferase, for use in a CRE-luciferase reporter assay, as described below (Example 11).

Qualitative results of the above-described assays may be obtained by competitive autoradiographic-plate binding assays; alternatively, Scatchard plots may be used to generate quantitative results. The labels of the present invention may be coupled directly or indirectly to the desired component of the assay, according to methods well known in the art. The choice of label depends on a number of relevant factors, including the sensitivity required, the ease of conjugation with the compound to be labeled, stability requirements, and available instrumentation.

Both direct and competitive binding assays may be used in a variety of different configurations. In one competitive binding assay, for example, the candidate agent may compete against labeled CRE (the labeled analyte) for a specific binding site on ATF5 (the capture agent) that is bound to a solid substrate, such as a column chromatography matrix or tube. Alternatively, the candidate agent may compete for a specific binding site on labeled ATF5 (the labeled analyte) against wild-type CRE or a fragment thereof (the capture agent) that is bound to a solid substrate. The capture agent is bound to the solid substrate in order to effect separation of bound labeled analyte from the unbound labeled analyte. In either type of competitive binding assay, the concentration of labeled analyte that binds the capture agent bound to the solid substrate is inversely proportional to the ability of a candidate agent to compete in the binding assay. The amount of inhibition of labeled analyte by the candidate agent depends on the binding assay conditions and on the concentrations of candidate agent, labeled analyte, and capture agent that are used.

Another competitive binding assay, for use in detecting agents that bind to ATF5, may be conducted in a liquid phase. In this type of assay, any of a variety of techniques known in the art may be used to separate the bound labeled analyte (which may be either CRE or ATF5) from the unbound labeled analyte. Following such separation, the amount of bound labeled analyte may be determined. The amount of unbound labeled analyte present in the separated sample is inversely proportional to the amount of bound labeled analyte.

In the further alternative, a homogeneous binding assay may be performed, in which a separation step is not needed. In this type of binding assay, the label on the labeled analyte (which may be either CRE or ATF5) is altered by the binding of the analyte to the capture agent. This alteration in the labeled analyte results in a decrease or increase in the signal emitted by the label, so that measurement of the label at the end of the binding assay allows for detection or quantification of the analyte.

Under specified assay conditions, a candidate agent is considered to be capable of inhibiting the binding of CRE to ATF5 in a competitive binding assay if the amount of binding of the labeled analyte to the capture agent is decreased by 50% or more (preferably 90% or more). Where a direct binding assay configuration is used, a candidate agent is considered to bind ATF5 when the signal measured is twice the background level or higher. Furthermore, as proof of the specificity of the candidate agent identified using an ATF5 competitive binding assay, binding competition also may be performed using purified ATF5 in the presence of washed ribosomes. A functional assay, such as a luciferase assay, also may be used to screen for ATF5 inhibitors, as described herein.

As disclosed herein, ATF5 has been implicated in a number of biological events in neural stem cells, neural progenitor cells, and neuroblastoma cells. For example, it has been shown that ATF5 plays a role in the differentiation of neural stem and progenitor cells, and may be associated with uncontrolled cell proliferation in neuroblastomas and other neural tumors. Accordingly, it is clear that therapeutics designed to inhibit ATF5 (i.e., those which bind to, or are otherwise reactive with, ATF5) may be useful in regulation of a number of ATF5-associated biological events, including differentiation of neural stem cells and neural progenitor cells, and control of proliferation of neural tumor cells.

Thus, once the candidate agent of the present invention has been screened, and has been determined to have a suitable inhibitory effect on ATF5 (i.e., it is reactive with ATF5, it binds ATF5, or it otherwise inactivates ATF5), it may be evaluated for its effect on differentiation of neural stem cells or neural progenitor cells, or on tumor-cell proliferation. In particular, the candidate agent may be assessed for its ability to act as a promoter of differentiation, or as an inhibitor of tumor-cell division proliferation, or to otherwise function as an appropriate tumor-suppressing agent. It is expected that the ATF5 inhibitor of the present invention will be useful for promoting differentiation of neural stem cells and neural progenitor cells, and for treating neural tumors, including those disclosed herein. Furthermore, the inventors propose that the ATF5 inhibitor of the present invention might be useful for restoring proliferation control in tumor cells.

Accordingly, the present invention further comprises the steps of: (c) contacting the candidate agent with neural stem cells or neural progenitor cells containing ATF5; and (d) determining if the agent has an effect on an ATF5-associated biological event in the neural stem cells or neural progenitor cells. As used herein, an "ATF5-associated biological event" includes a biochemical or physiological process in which ATF5 levels or activity have been implicated. As disclosed herein, examples of ATF5-associated biological events include, without limitation, binding to, and interaction with, CRE; regulation of differentiation in neural stem cells or neural progenitor cells; and proliferation of neural tumor cells. As further used herein, a cell "containing ATF5" is a cell in which ATF5, or a derivative or homologue thereof, is naturally expressed or naturally occurs.

According to this method of the present invention, a candidate agent may be contacted with one or more neural stem cells or neural progenitor cells in vitro. For example, a culture of cells may be incubated with a preparation containing the candidate agent. The candidate agent's effect on an ATF5-associated biological event then may be assessed by any biological assays or methods known in the art, including histological analyses. In one embodiment of the present invention, the neural stem cells or neural progenitor cells express luciferase (see Examples 3 and 11).

The present invention is further directed to agents identified by the above-described identification methods. Such agents may be useful for promoting differentiation of neural stem cells or neural progenitor cells, and for treating an ATF5-associated condition. As used herein, an "ATF5-associated condition" is a condition, disease, or disorder in which ATF5 levels or activity have been implicated, and includes the following: an ATF5-associated biological event, and neural tumors. The ATF5-associated condition may be treated in the subject by administering to the subject an amount of the agent effective to treat the ATF5-associated condition in the subject. This amount may be readily determined by one skilled in the art.

Accordingly, in one embodiment, the present invention provides a method for promoting differentiation in neural stem cells or neural progenitor cells, by contacting the cells with the above-described agent, in an amount effective to promote differentiation in the cells. In another embodiment, the present invention provides a method for treating or preventing a neural tumor in a subject, by administering to the subject the above-described agent, in an amount effective to treat or prevent the neural tumor in the subject. In a preferred embodiment of the present invention, the neural tumor is a neuroblastoma.

The present invention also provides a pharmaceutical composition comprising the agent identified by the above-described identification method and a pharmaceutically-acceptable carrier. Examples of suitable pharmaceutically-acceptable carriers, and methods of preparing pharmaceutical formulations and compositions, are described above. The pharmaceutical composition of the present invention would be useful for contacting neural stem cells or neural progenitor cells with an agent that inhibits interaction between CRE and ATF5, in order to promote differentiation of the cells, and would also be useful for treating an ATF5-associated condition. In such a case, the pharmaceutical composition is administered to a subject in an amount effective to treat the ATF5-associated condition.

The inventors have demonstrated herein that ATF5 expression is elevated in neuroblastoma cells. Thus, ATF5 represents a marker for neuroblastoma. Accordingly, the present invention further provides a method for determining whether a subject has a neural tumor, thereby permitting the diagnosis of such a neural tumor in the subject. The subject may be any of those described above. Preferably, the subject is a human. Examples of neural tumors have been previously discussed. In one embodiment of the present invention, the neural tumor is a neuroblastoma. The method of the present invention comprises assaying a diagnostic sample of the subject for ATF5, wherein detection of an ATF5 level elevated above normal is diagnostic of a neural tumor in the subject. As used herein, "ATF5" includes both an ATF5 protein and an ATF5 analogue, as discussed above.

In accordance with the method of the present invention, the diagnostic sample of a subject may be assayed in vitro or in vivo. Where the assay is performed in vitro, a diagnostic sample from the subject may be removed using standard procedures. The diagnostic sample may be any nervous tissue, including brain tissue, which may be removed by standard biopsy. In addition, the diagnostic sample may be any tissue known to have a neural tumor, any tissue suspected of having a neural tumor, or any tissue believed not to have a neural tumor. In a preferred embodiment of the present invention, the diagnostic sample contains post-mitotic cells. More preferably, the diagnostic sample contains neural-tumor cells.

Protein may be isolated and purified from the diagnostic sample of the present invention using standard methods known in the art, including, without limitation, extraction from a tissue (e.g., with a detergent that solubilizes the protein) where necessary, followed by affinity purification on a column, chromatography (e.g., FTLC and HPLC), immunoprecipitation (with an antibody to ATF5), and precipitation (e.g., with isopropanol and a reagent such as Trizol). Isolation and purification of the protein may be followed by electrophoresis (e.g., on an SDS-polyacrylamide gel). Nucleic acid may be isolated from a diagnostic sample using standard techniques known to one of skill in the art.

In accordance with the method of the present invention, a neural tumor in a subject is diagnosed by assaying a diagnostic sample of the subject for ATF5. The level of ATF5 in the sample, for example, may be detected by measuring ATF5 amounts in the sample. A diagnostic sample may be assayed for the level of ATF5 by assaying for ATF5 protein, ATF5 cDNA, or ATF5 mRNA. The appropriate form of ATF5 will be apparent based on the particular techniques discussed herein. Preferably, the diagnostic sample of the present invention is assayed for the level of ATF5 protein. It is contemplated that the diagnostic sample may be assayed for expression of any or all forms of ATF5 protein (including precursor forms, endoproteolytically-processed forms, the 22-kDa and 30-kDa forms, and other forms resulting from post-translational modification) in order to determine whether a subject or patient has a neural tumor.

Alternatively, the level of ATF5 in the sample may be detected by detecting above-normal interaction of ATF5 and CRE. Accordingly, in one embodiment of the present invention, the level of ATF5 elevated above normal is detected by detecting above-normal interaction of ATF5 and CRE. Methods for detecting interaction between CRE and ATF5 have been discussed above.

As used herein, the term "elevated above normal" means that ATF5 is detected at a level that is significantly greater than the level expected for the same type of diagnostic sample taken from a nondiseased subject or patient (i.e., one who does not have a neural tumor) of the same gender and of similar age. As further used herein, "significantly greater" means that the difference between the level of ATF5 that is elevated above normal, and the expected (normal) level of ATF5, is of statistical significance. Preferably, the level of ATF5 elevated above normal is a level that is at least 10% greater than the level of ATF5 otherwise expected in the diagnostic sample. Where ATF5 is expected to be absent from a particular diagnostic sample taken from a particular subject or patient, the normal level of ATF5 for that subject or patient is nil. Where a particular diagnostic sample taken from a particular subject or patient is expected to have a low, constitutive level of ATF5, that low level is the normal level of ATF5 for that subject or patient. As disclosed herein, ATF5 is generally present at lower levels in post-mitotic neurons, than in neural stem cells, neural progenitor cells, or neural tumor cells.

Expected or normal levels of ATF5 for a particular diagnostic sample taken from a subject or patient may be easily determined by assaying nondiseased subjects of a similar age and of the same gender. For example, diagnostic samples may be obtained from at least 30 normal, healthy men between the ages of 25 and 80, to determine the normal quantity of ATF5 in males. A similar procedure may be followed to determine the normal quantity of ATF5 in females. Once the necessary or desired samples have been obtained, the normal quantity of ATF5 in men and women may be determined using a standard assay for quantification, such as flow cytometry, Western-blot analysis, or an ELISA for measuring protein quantities, as described below. For example, an ELISA may be run on each sample in duplicate, and the mean and standard deviation of the quantity of ATF5 may be determined. If necessary, additional subjects may be recruited before the normal quantity of ATF5 is determined. A similar type of procedure may be used to determine the expected or normal level of interaction between ATF5 and CRE for a particular diagnostic sample taken from a subject or patient.

In accordance with the method of the present invention, a diagnostic sample of a subject may be assayed for ATF5 (or for interaction between ATF5 and CRE), and ATF5 (or interaction between ATF5 and CRE) may be detected in a diagnostic sample, using assays and detection methods readily determined from the known art (e.g., immunological techniques, hybridization analysis, fluorescence imaging techniques, and/or radiation detection, etc.), as well as any assays and detection methods disclosed herein (e.g., immunoprecipitation, Western-blot analysis, etc.). For example, a diagnostic sample of a subject may be assayed for ATF5 using an agent reactive with ATF5. The agent may include any of those described above. Preferably, the agent of the present invention is labeled with a detectable marker or label.

In one embodiment of the present invention, the agent reactive with ATF5 is an antibody. As used herein, the antibody of the present invention may be polyclonal or monoclonal. In addition, the antibody of the present invention may be produced by techniques well known to those skilled in the art. Polyclonal antibody, for example, may be produced by immunizing a mouse, rabbit, or rat with purified ATF5 or with a short peptide sequence thereof. Monoclonal antibody then may be produced by removing the spleen from the immunized mouse, and fusing the spleen cells with myeloma cells to form a hybridoma which, when grown in culture, will produce a monoclonal antibody.

The antibodies used herein may be labeled with a detectable marker or label. Labeling of an antibody may be accomplished using one of a variety of labeling techniques, including peroxidase, chemiluminescent labels known in the art, and radioactive labels known in the art. The detectable marker or label of the present invention may be, for example, a nonradioactive or fluorescent marker, such as biotin, fluorescein (FITC), acridine, cholesterol, or carboxy-X-rhodamine, which can be detected using fluorescence and other imaging techniques readily known in the art. Alternatively, the detectable marker or label may be a radioactive marker, including, for example, a radioisotope. The radioisotope may be any isotope that emits detectable radiation, such as 35S, 32P, 125I, 3H, or 14C. Radioactivity emitted by the radioisotope can be detected by techniques well known in the art. For example, gamma emission from the radioisotope may be detected using gamma imaging techniques, particularly scintigraphic imaging. Preferably, the agent of the present invention is a high-affinity antibody labeled with a detectable marker or label.

Where the agent of the present invention is an antibody reactive with ATF5, a diagnostic sample taken from the subject may be purified by passage through an affinity column which contains an anti-ATF5 antibody as a ligand attached to a solid support, such as an insoluble organic polymer in the form of a bead, gel, or plate. The antibody attached to the solid support may be used in the form of a column. Examples of suitable solid supports include, without limitation, agarose, cellulose, dextran, polyacrylamide, polystyrene, sepharose, or other insoluble organic polymers. The antibody may be further attached to the solid support through a spacer molecule, if desired. Appropriate binding conditions (e.g., temperature, pH, and salt concentration) for ensuring binding of the agent and the antibody may be readily determined by the skilled artisan. In a preferred embodiment, the antibody is attached to a sepharose column, such as Sepharose 4B.

Where the agent is an antibody, a diagnostic sample of the subject may be assayed for ATF5 using binding studies that utilize one or more antibodies immunoreactive with ATF5, along with standard immunological detection techniques. For example, the ATF5 protein eluted from the affinity column may be subjected to an ELISA assay, Western-blot analysis, flow cytometry, or any other immunostaining method employing an antigen-antibody interaction. Preferably, the diagnostic sample is assayed for ATF5 using Western blotting.

Alternatively, a diagnostic sample of a subject may be assayed for ATF5 using hybridization analysis of nucleic acid extracted from the diagnostic sample taken from the subject. According to this method of the present invention, the hybridization analysis may be conducted using Northern blot analysis of mRNA. This method also may be conducted by performing a Southern blot analysis of DNA using one or more nucleic acid probes, which hybridize to nucleic acid encoding ATF5. The nucleic acid probes may be prepared by a variety of techniques known to those skilled in the art, including, without limitation, the following: restriction enzyme digestion of ATF5 nucleic acid; and automated synthesis of oligonucleotides having sequences which correspond to selected portions of the nucleotide sequence of the ATF5 nucleic acid, using commercially-available oligonucleotide synthesizers, such as the Applied Biosystems Model 392 DNA/RNA synthesizer.

The nucleic acid probes used in the present invention may be DNA or RNA, and may vary in length from about 8 nucleotides to the entire length of the ATF5 nucleic acid. The ATF5 nucleic acid used in the probes may be derived from mammalian ATF5. The nucleotide sequence for human ATF5, rat ATF5, and mouse ATF5, for example, are known. Using this sequence as a probe, the skilled artisan could readily clone a corresponding ATF5 cDNA from other species. In addition, the nucleic acid probes of the present invention may be labeled with one or more detectable markers or labels. Labeling of the nucleic acid probes may be accomplished using one of a number of methods known in the art—e.g., nick translation, end labeling, fill-in end labeling, polynucleotide kinase exchange reaction, random priming, or SP6 polymerase (for riboprobe preparation)—along with one of a variety of labels—e.g., radioactive labels, such as 35S, 32P, or 3H, or nonradioactive labels, such as biotin, fluorescein (FITC), acridine, cholesterol, or carboxy-X-rhodamine (ROX). Combinations of two or more nucleic acid probes (or primers), corresponding to different or overlapping regions of the ATF5 nucleic acid, also may be used to assay a diagnostic sample for ATF5, using, for example, PCR or RT-PCR.

The detection of ATF5 (or interaction between ATF5 and CRE) in the method of the present invention may be followed by an assay to measure or quantify the extent of ATF5 in a diagnostic sample of a subject. Such assays are well known to one of skill in the art, and may include immunohistochemistry/immunocytochemistry, flow cytometry, mass spectroscopy, Western-blot analysis, or an ELISA for measuring amounts of ATF5 protein. For example, to use an immunohistochemistry assay, histological (paraffin-embedded) sections of tissue may be placed on slides, and then incubated with an antibody against ATF5. The slides then may be incubated with a second antibody (against the primary antibody), which is tagged to a dye or other colorimetric system (e.g., a fluorochrome, a radioactive agent, or an agent having high electron-scanning capacity), to permit visualization of ATF5 present in the sections.

It is contemplated that the diagnostic sample in the present invention frequently will be assayed for ATF5 (or interaction between ATF5 and CRE) not by the subject or patient, nor by his/her consulting physician, but by a laboratory technician or other clinician. Accordingly, the method of the present invention further comprises providing to a subject's or patient's consulting physician a report of the results obtained upon assaying a diagnostic sample of the subject or patient for ATF5.

The present invention further provides a method for assessing the efficacy of therapy to treat a neural tumor in a subject or patient who has undergone or is undergoing treatment for a neural tumor. The method of the present invention comprises assaying a diagnostic sample of the subject or patient for ATF5, wherein a normal level of ATF5 in the diagnostic sample is indicative of successful therapy to treat a neural tumor, and a level of ATF5 elevated above normal in the diagnostic sample is indicative of a need to continue therapy to treat a neural tumor. In one embodiment of the present invention, a level of ATF5 elevated above normal is detected by detecting above-normal interaction between ATF5 and CRE. The neural tumor may be any of those described above. The diagnostic sample may be assayed for ATF5 (or interaction between ATF5 and CRE) in vitro or in vivo. In addition, the diagnostic sample may be assayed for ATF5 (or interaction between ATF5 and CRE) using all of the various assays and methods of detection and quantification described above. This method of the present invention provides a means for monitoring the effectiveness of therapy to treat a neural tumor by permitting the periodic assessment of levels of ATF5 (or interaction between ATF5 and CRE) in a diagnostic sample taken from a subject or patient.

According to the method of the present invention, a diagnostic sample of a subject or patient may be assayed, and levels of ATF5 (or interaction between ATF5 and CRE) may be assessed, at any time following the initiation of therapy to treat a neural tumor. For example, levels of ATF5 (or interaction between ATF5 and CRE) may be assessed while the subject or patient is still undergoing treatment for a neural tumor. Where levels of ATF5 detected in an assayed diagnostic sample of the subject or patient continue to remain elevated above normal, a physician may choose to continue with the subject's or patient's treatment for the neural tumor. Where levels of ATF5 in an assayed diagnostic sample of the subject or patient decrease through successive assessments, it may be an indication that the treatment for a neural tumor is working, and that treatment doses could be decreased or even ceased. Where levels of ATF5 in an assayed diagnostic sample of the subject or patient do not rapidly decrease through successive assessments, it may be an indication that the treatment for a neural tumor is not working, and that treatment doses could be increased. Where ATF5 is no longer detected in an assayed diagnostic sample of a subject or patient at a level elevated above normal, a physician may conclude that the treatment for a neural tumor has been successful, and that such treatment may cease.

It is within the confines of the present invention to assess levels of ATF5 (or interaction between ATF5 and CRE) following completion of a subject's or patient's treatment for a tumor, in order to determine whether the tumor has recurred in the subject or patient. Accordingly, an assessment of levels of ATF5 (or interaction between ATF5 and CRE) in an assayed diagnostic sample may provide a convenient way to conduct follow-ups of patients who have been diagnosed with a tumors. Furthermore, it is within the confines of the present invention to use assessed levels of ATF5 (or interaction between ATF5 and CRE) in an assayed diagnostic sample as a clinical or pathologic staging tool, as a means of determining the extent of a tumor in the subject or patient, and as a means of ascertaining appropriate treatment options.

A correlation exists, in general, between levels of ATF5 in post-mitotic neural cells and neuroblastoma. Therefore, it is also contemplated in the present invention that assaying a diagnostic sample of a subject for ATF5 may be a useful means of providing information concerning the prognosis of a subject or patient who has a neural tumor. Accordingly, the present invention further provides a method for assessing the prognosis of a subject who has a neural tumor, comprising assaying a diagnostic sample of the subject for ATF5, wherein the subject's prognosis improves with a decreased level of ATF5 in the diagnostic sample, and the subject's prognosis worsens with an increased level of ATF5 in the diagnostic sample. In one embodiment of the present invention, the level of ATF5 elevated above normal is detected by detecting above-normal interaction between ATF5 and CRE. Suitable diagnostic samples, assays, and detection and quantification methods for use in the method of the present invention have already been described. This method of the present invention provides a means for determining the prognosis of a subject or patient diagnosed with a neural tumor based upon the level of ATF5, or interaction between ATF5 and CRE, in an assayed diagnostic sample of the subject or patient.

According to the method of the present invention, a diagnostic sample of a subject or patient may be assayed, and levels of ATF5 (or interaction between ATF5 and CRE) may be assessed, at any time during or following the diagnosis of a neural tumor in the subject or patient. For example, levels of ATF5 (or interaction between ATF5 and CRE) in an assayed diagnostic sample may be assessed before the subject or patient undergoes treatment for a neural tumor, in order to determine the subject's or patient's initial prognosis. Additionally, levels of ATF5 (or interaction between ATF5 and CRE) in an assayed diagnostic sample may be assessed while the subject or patient is undergoing treatment for a neural tumor, in order to determine whether the subject's or patient's prognosis has become more or less favorable through the course of treatment.

For example, where the level of ATF5 detected in an assayed diagnostic sample of the subject or patient is, or continues to remain, significantly high, a physician may conclude that the subject's or patient's prognosis is unfavorable. Where the level of ATF5 in an assayed diagnostic sample of the subject or patient decreases through successive assessments, it may be an indication that the subject's or patient's prognosis is improving. Where the level of ATF5 in an assayed diagnostic sample of the subject or patient does not decrease significantly through successive assessments, it may be an indication that the subject's or patient's prognosis is not improving. Finally, where the level of ATF5 is low, or is normal, in a diagnostic sample of the subject or patient, a physician may conclude that the subject's or patient's prognosis is favorable.

The discovery that ATF5 can be detected in a wide variety of tumor cells provides a means of identifying patients with a tumor, and presents the potential for commercial application in the form of a test for the diagnosis of a tumor. The development of such a test could provide general screening procedures. Such procedures can assist in the early detection and diagnosis of a tumor, and can provide a method for the follow-up of patients in whom a level of ATF5 elevated above normal has been detected.

Accordingly, the present invention further provides a kit for use as an assay of a tumor, comprising an ATF5-specific agent and reagents suitable for detecting ATF5. The ATF5-specific agent may be any agent reactive with ATF5 protein or nucleic acid, including a nucleic acid probe which hybridizes to nucleic acid encoding ATF5, an antibody, and any of the agents described above. The agent may be used in any of the above-described assays or methods for detecting or quantifying levels of ATF5. Preferably, the agent of the present invention is labeled with a detectable marker or label.

The present invention is described in the following Examples, which are set forth to aid in the understanding of the invention, and should not be construed to limit in any way the scope of the invention as defined in the claims which follow thereafter.

EXAMPLES

Example 1

Reagents

Cell-culture media, RPMI 1640 and DMEM, and molecular biology reagents, Tag platinum DNA polymerase, SuperScript II reverse transcriptase, and LipofectAMINE 2000, were obtained from Invitrogen, Inc. (Carlsbad, Calif.). Donor horse and fetal bovine serum were obtained from JRH Biosciences, Inc. (Lenexa, Kans.). The Marathon cDNA amplification library kit was obtained from Clontech (Palo Alto, Calif.), and PCR primers were obtained from Integrated DNA Technologies or Life Technologies, Inc. Anti-FLAG M2 antibody was from Sigma Corp. (St. Louis, Mo.).

Cell Culture

PC12 cells were grown on collagen-coated dishes, as previously described (Greene et al., Establishment of a noradrenergic clonal line of rat adrenal pheochromocytoma cells which respond to nerve growth factor. *Proc. Natl. Acad. Sci. USA*, 73:2424-28, 1998), with or without human recombinant nerve growth factor (NGF) (Genentech, Inc.). Dissociated cultures of telencephalic cells were prepared from E14 Sprague-Dawley rats. Telencephalic cells were trypsinized (0.05% in 0.53 mM EDTA; Invitrogen, Inc.) for 30 min (Li et al., Neuronal differentiation of precursors in the neocortical ventricular zone is triggered by BMP. *J. Neurosci.*, 18:8853-62, 1998), and dissociated cells were centrifuged and resuspended in DMEM containing 5% FBS, 10 ng/ml EGF, and 20 ng/ml bFGF, then plated on 24-well dishes coated with polylysine at 3-5×10$^5$ cells per well (Laywell et al., Multipotent neurospheres can be derived from forebrain subependymal zone and spinal cord of adult mice after protracted post-mortem intervals. *Exp. Neurol.*, 156:430-33, 1999). The presence of bFGF promotes proliferation of the progenitor cells, but does not interfere with their differentiation into neurons (Ghosh and Greenberg, Distinct roles for bFGF and NT-3 in the regulation of cortical neurogenesis. *Neuron*, 15:89-03, 1995).

Adherent clonal neurosphere cultures were prepared from newborn mouse subependymal zone cells, as previously described (Kukekov et al., A nestin-negative precursor cell from the adult mouse brain gives rise to neurons and glia. *Glia*, 21:399-07, 1997; Kukekov et al., Multipotent stem/progenitor cells with similar properties arise from two neurogenic regions of adult human brain. *Exp. Neurol.*, 156:333-44, 1999). The cell suspension used to generate neurospheres was filtered through sterile gauze, and visually verified to contain only single cells.

Cloning of Full-Length rATF5 and Plasmid Constructs

SAGE tag, CATGAGAACCTAGTC (SEQ ID NO:3), was found in rat EST, UI-R-G0-ur-g-10-0-UI (GenBank™/EBI accession number AI576016), which, in turn, showed high homology with the 3' end of murine ATF5. To clone the open-reading frame of rat ATF5, PCR antisense primer 5'-CTTGGTTTCTCAGTTGCAC-3' (SEQ ID NO:4) (derived from the sequence of the above EST) was used for 5' RACE PCR, using the Clontech Marathon kit according to the manufacturer's protocol. The first-strand cDNA PCR template was prepared from 5 μg of PC12 cell total RNA, by reverse transcription with Superscript II. The products of the 5' RACE PCR included the second of 2 potential Kozak start sites.

Cloning of the rATF5 open-reading frame that included the first potential start site was achieved with sense PCR primer, 5'-TGCACCTGTGCCTCAGCCATGTC-3' (SEQ ID NO:5). This sequence was obtained from an EST sequence (GenBank™/EBI accession number AW917099) that overlapped with the 5' end of the 5' RACE PCR product described above. Both potential rATF5 forms were FLAG-tagged, by PCR, with sense primers, 5'-CTCGAGAACCATGGACTACAAG-GACGATGATGACAAAGGATCACTCCTGGCGAC CCT-3' (SEQ ID NO:6), and 5'-CTCGAGAAGCATGGACTA-CAAGGACGATGATG ACAAAGGAGCATCCCTACTCAAGAA-3' (SEQ ID NO:7). 5'-GAATTCTCGAG CTTGGTTTCTCAGTTG-CAC-3' (SEQ ID NO:8) was the antisense primer for both ATF5s. NTAzip-ATF5 was constructed by overlapping PCR, using FLAG-tagged ATF5 (potential start site 2 form) as the template.

PCR product 1 was produced with 5'-CTCGAGAAG-CATGGACTACAA GGACGATGATGACAAAGGAG-CATCCCTACTCAAGAA-3' (SEQ ID NO:7) and 5'-TTCT-TCTGCTTCTTTTTCTAGTAGTTCTTCGTTTTCTCTTG-CTAGTTCTTCTGCTCTTTG TTCGAGG GTGCTG-GCAGGACTAGGATA-3' (SEQ ID NO:9) as primers, and PCR product 2 was made with
5'-GCAAGAGAAAACGAAGAACTACTA-GAAAAAGAAGCAGAAGAACTAGAACAAGA AATG-CAGAGCTAGAGGGCGAGTGCCAAGGG-3' (SEQ ID NO:10) and 5'-GAATTCTCGAGCTTG GTTTCTCAGT-TGCAC-3' (SEQ ID NO:11) as primers. Products 1 and 2 were mixed, and the product (FL-NTAzip-ATF5) was PCR amplified with 5'-CTCGAGAAGCATGGACTACAAG-GACGATGATGACAAAGGAGCATCCCTACTCAAGA A-3' (SEQ ID NO:7) and 5'-GAATTCTCGAGCTTGGTTT CTCAGTTGCAC-3' (SEQ ID NO:8). To generate NTAzip-ATF5, the activation domain was removed from FL-NTAzip-ATF5 by PCR, using primers 5'-GAATTCAACCATGGAC-TACAAGGACGA TGATGACAAAATGGCATCTATGACTG-GAGGACAACAAATGGGAAGAGACCCA GACCTC-GAACAAAGAGCAGAA-3' (SEQ ID NO:11) (sense) and 5'-GAATTCT CGAGCTTGGTTTCTCA GTTGCAC-3' (SEQ ID NO:8) (antisense).

NTAzip-ATF5 was N-terminal FLAG-tagged with a predicted open-reading frame of MDYKDDDDKMASMTG-GQQMGRDPDLEQRAEELRENEELLEKEAEELE QENAELEGECQGLEARNRELRERAESV-EREIQYVKDLLIEVYKARSQRTRSA (SEQ ID NO:12), where the DNA binding motif was replaced with an amphipathic acidic α-helical sequence, as marked in bold (Moll et al., Attractive interhelical electrostatic interactions in the proline- and acidic-rich region (PAR) leucine zipper subfamily preclude heterodimerization with other basic leucine zipper subfamilies. *J. Biol. Chem.*, 275:34826-832, 2000). All PCR products were subcloned into the Topo II pCR 2.1 vector, and were sequenced to verify identity. After confirmation, all full-length constructs were subcloned into the EcoR1 sites of the pCMS-eGFP vector.

Retrovirus plasmids were constructed by blunt ligation of eGFP into the XhoI site of QCX (Julius et al., Q vectors, bicistronic retroviral vectors for gene transfer. *Biotechniques*, 28:702-08, 2000). Subsequently, full-length FLAG-ATF5 was blunt ligated into the BsiWI site of QCX-eGFP, to form the bicistronic Q vector construct (QC-FLAG-ATF5-eGFP) for retrovirus production.

The CRE-luciferase reporter plasmid was constructed by annealing synthetic oligo 5'-TCGAGTCATGGTAAAAAT-GACGTCATGGTAATTATCATGGTAAAAAT GACGT-CATGGTAATTATCATGGTAAAAAT-GACGTCATGGTAATTA-3' (SEQ ID NO:13) to 5'-AGC TTAATTACCATGACGTCATTTTTACCAT-GATAATTACCATGACGTCATT TTTACCA TGATAAT-TACCATGACGTCATTTTTACCATGAC-3' (SEQ ID NO:14), to form a double-stranded DNA (Peters et al., ATF-7, a novel bZIP protein, interacts with the PRL-1 protein-tyrosine phosphatase. *J Biol. Chem.*, 276:13718-26, 2001). The annealed DNA was ligated into the XhoI and HindIII sites of the GL3 plasmid. VPI6-CREB (Columbia University) was subcloned into the EcoRI and XbaI sites of the pCMS-eGFP vector.

ATF5 Antiserum

The CTRGDRKQKKRDQNK (SEQ ID NO:15) peptide, corresponding to ATF5 DNA-binding-domain I (plus an N-terminal cysteine, for conjugation to keyhole limpet hemocyanin), was used as the antigen for production of rabbit antiserum.

Western-Blot Analysis

Cultured cells and adult mouse cortex were harvested in Laemmli sample buffer. The protein concentrations were measured by the Bradford assay (Bio-Rad, Hercules, Calif.), and cell proteins were resolved by SDS-PAGE on a 12% gel. The separated proteins were electrophoretically transferred from the gel to Hybond P membrane (Amersham) (Towbin et al., Electrophoretic transfer of proteins from polyacrylamide gels to nitrocellulose sheets: procedure and some applications. *Proc. Natl. Acad. Sci. USA*, 76:4350-54, 1979). The membranes were blocked for 1 h in PBS containing 5% milk and 1% BSA, and immunolabeled overnight with ATF5 antipeptide antiserum, at 1:1000, in PBS containing 5% milk and 1% BSA. For detection, the blots were washed and probed with goat anti-rabbit HRP-conjugated antibody (Pierce), and then visualized on film using an enhanced chemiluminescence detection kit (ECL) (Amersham). For the PC12 cell NGF time course, to normalize for protein loading, the blots were stripped of immunocomplexes, as described by Amersham, and reprobed with ERK1 C-16 antibody (Santa Cruz) and goat anti-rabbit HRP-conjugated antibody, followed by ECL film visualization. Densitometry was carried out with NIH Image 1.62 software.

Immunochemistry

For PC12 cells, fluorescence immunohistochemistry was carried out, as previously described (Angelastro et al., Characterization of a novel isoform of caspase-9 that inhibits apoptosis. *J. Biol. Chem.*, 276:12190-200, 2001). For dissociated telencephalic cultures, the cells were fixed with 4% paraformaldehyde and 2% sucrose in PBS, for 15 min. After 3 washes in PBS, the cells were blocked in 10% non-immune goat serum and 0.3% Triton X-100 for 1 h. The cultures were immunolabeled separately with the following combinations: (1) rabbit anti-GFP (1:1000 dilution; Clontech) and mouse anti-nestin (1:500; rat-401 from the DSBH antibody collection, University of Iowa); (2) rabbit anti-GFP (1:1000 dilution) and mouse TUJ1 (1:2000 dilution; Covance); (3) mouse GFP (1:500; Sigma) and rabbit anti-neurofilament 160 kDa (1:200; Columbia University); or (4) mouse GFP (1:500) and rabbit anti-GFAP (1:500; Dako) antibody, in 10% non-immune goat serum and 0.3% Triton X100, for 1 h, followed by secondary labeling with goat FITC-conjugated anti-rabbit or rhodamine-conjugated anti-mouse antibodies (Alexa) at 1:5000.

For immunolabeling, embryos were fixed in 4% paraformaldehyde in 0.1 M phosphate buffer, overnight, then cryoprotected in 30% sucrose; they were then frozen in O.C.T. compound (Tissue-TEK). Cryosectioned (14 µm) embryos were blocked for 1 h in 10% non-immune goat serum and 0.3% Triton X-100. The sections were then incubated with ATF5 antiserum (1:500) and TUJ1 antibody (1:2000), in 2.5% non-immune goat serum and 0.3% Triton X-100, overnight. The sections were subsequently incubated for 1 h with goat FITC-conjugated anti-rabbit and rhodamine-conjugated anti-mouse antibodies, in 10% non-immune goat serum and 0.3% Triton X-100.

For adherent neurospheres, cells were fixed with 4% paraformaldehyde in PBS/2% sucrose for 10 min, at room temperature, and then permeabilized for 5 min with 0.5% Triton X-100 in ice-cold PBS/2% sucrose. After blocking with 25% goat or bovine serum in PBS, for 20 min, the cultures were incubated with primary antibodies (diluted in 25% serum in PBS for 30 min, at room temperature, followed by 3 washes with PBS), and then incubated with the appropriate secondary goat anti-rabbit or anti-mouse antibodies conjugated with FITC (Alexa Fluor 488, Molecular Probes, A 11001) or Texas Red-X (Molecular Probes, T 6391) for 30 min, at room temperature, at 1:200. The cultures were then incubated with the second set of primary and secondary antibodies, as above. Immunochemical reagents were anti-AC133/2 antibody (Miltenyl Biotech), anti-neurofilament 160 (clone NN18, Sigma), anti-beta tubulin isotype III (clone SDL.3D10, Sigma), and goat anti-tau antiserum (clone C-17, Santa Cruz), all diluted according to the manufacturers' recommendations.

Confocal microscopy was carried out on either a Zeiss LSM 410 confocal laser scanning microscope (neural brain sections) or on a Bio-Rad Confocal Microscope System 1024ES (neurosphere cultures). Images were obtained under conditions that were identical for both fluorochromes. Confocal images of XY and YZ planes confirmed co-localization in brain sections.

In Situ Hybridization

Non-radioactive in situ hybridization of sections was carried out as previously described (Mendelsohn et al., Stromal cells mediate retinoid-dependent functions essential for renal development. *Development*, 126:1139-48, 1999). The antisense ATF5 probe was synthesized using T3 RNA polymerase, and the pCMS-eGFP-ATF5 construct was digested with NheI as the template. The corresponding sense probe was synthesized using T7 RNA polymerase, and the pCMS-eGFP-ATF5 construct was digested with NotI as the template.

Transient Transfections

For PC12 cells, transfection was carried out using 0.5 µg of plasmid well and 6 µl/well of LipofectAMINE 2000, for 9 h. Thereafter, the cells were re-fed with fresh culture medium, and then handled as described. For telencephalic cells, transfection was performed with 2.0 µg of plasmid/well and 2 µl/well of LipofectAMINE 2000 for 7 h followed by an exchange of medium. For transfection of ATF5 siRNA (AAN19; AAG UCA GCU GCU CUC AGG UAC (SEQ ID NO:16)), 6.67 µg/well of pCMS-EGFP vector were mixed with 80 pmol/well of siRNA in 100 µl of DMEM medium. An equal amount of DMEM medium, premixed with 1 µl of LipofectAMINE 2000/well, was added to, and mixed with, the vector and siRNA. After 30 min, the final mixture was added to ⅙ the volume containing the cells, and the cells were re-fed with fresh culture medium after 7 h of transfection. For the control, telencephalic cells were transfected with pCMS-EGFP vector alone.

Retrovirus Production and Infection of Telencephalic Cells

Nonreplicating retrovirus was made by transfecting subconfluent GP2 293 cells (grown in DMEM plus 10% FBS) with 5 µg of QCX-eGFP or pLeGFP, and 5 µg of pVSV-G, for production of empty eGFP retrovirus (as described by Clontech). Similarly, GP2 293 cells were transfected with 5 µg of QC-FLAG-ATF5-eGFP or pLeGFP-FLAG-NTAzip-ATF5, and 5 µg of pVSV-G, to make the bicistronic FLAG-ATF5-eGFP or fusion eGFP-FLAG-NTAzip-ATF5 retroviruses, respectively. After 48 h, medium was collected, and the virus was concentrated by centrifugation at 50,000×g, at 4° C. The final titer was approximately $1 \times 10^6$ virus particles per ml. The telencephalic cells were infected with 5-10 µl of retrovirus, one day after plating, and the cells were fixed 7 days after infection.

Scoring of Neuronal Differentiation

Transfected cells were detected by positive immunostaining for eGFP. Co-staining with anti-FLAG established that the GFP-positive PC12 cells also expressed ATF5 constructs.

NGF-treated PC12 cells (transfected unless otherwise noted) were scored for processes of length greater than two cell diameters (about 20 µm) (Greene et al., Culture and Experimental Use of the PC12 Rat Pheochromocytoma Cell Line. In: *Culturing Nerve Cells*, 2nd ed., Goslin, G. K., ed. (Cambridge, Mass.: The MIT Press, 1998) pp. 161-87. Transfected telencephalic neurons were scored for the presence of processes with lengths greater than two cell diameters (about 20 µm) and for co-staining with TUJ1, nestin, or NF-M antisera antibodies.

CRE-Luciferase Reporter Assay

PC12 cells were co-transfected with 1 µg of pCMS-eGFP (empty, or containing FLAG-tagged-ATF5 or FLAG-tagged NTAzip-ATF5) and with 0.2 µg of pG13-CRE-luciferase reporter and 1 µg of LacZ plasmid per well; cells were then transfected with 2 µl/well of LipofectAMINE 2000 24 h prior to harvesting. The cells were treated with NGF for a total of 1 h to 3 days. Luciferase levels were assayed using the Promega Luciferase System with Reporter Lysis Buffer, as described by the manufacturer. The level of LacZ activity was measured, as previously described (Sambrook et al., Molecular Cloning. In: *A Laboratory Manual*, 2nd ed. (Cold Spring Harbor, N.Y.: Cold Spring Harbor Laboratory Press, 1989) pp. 16-66.

Statistical Analysis

Multiple comparisons among the data from different plasmid transfections and retrovirus infections were achieved using Tucky's one way ANOVA test. Comparisons for pairs of data were conducted with Student's t-distribution test.

Results

Reciprocal Effects of NGF on ATF5 Protein Expression and Neurite Outgrowth

The inventors' previous findings revealed that long-term NGF treatment promotes a 25-fold down-regulation of ATF5 transcripts in PC12 cells (Angelastro et al., Identification of diverse nerve growth factor-regulated genes by serial analysis of gene expression (SAGE) profiling. *Proc. Natl. Acad. Sci. USA*, 97:10424-429, 2000). To determine whether this is reflected at the level of protein expression, the inventors cloned the coding sequence of rat ATF5 (GenBank/EBI accession number AY123225), and an antiserum was raised against a peptide corresponding to a portion of the deduced sequence of the DNA-binding domain. Western immunoblotting with this antiserum detected a single major band in extracts of PC12 cells (FIG. 1A), and in extracts of HEK-293 cells, primary human neuroblastoma, and mouse brain (data not shown), with an apparent molecular mass of 20-22 kDa. The nucleotide sequence of rat ATF5 indicates two potential in-frame Kozak start sites, and the apparent molecular mass of 20-22 kDa indicates preferential use of the second.

Figure 1B:
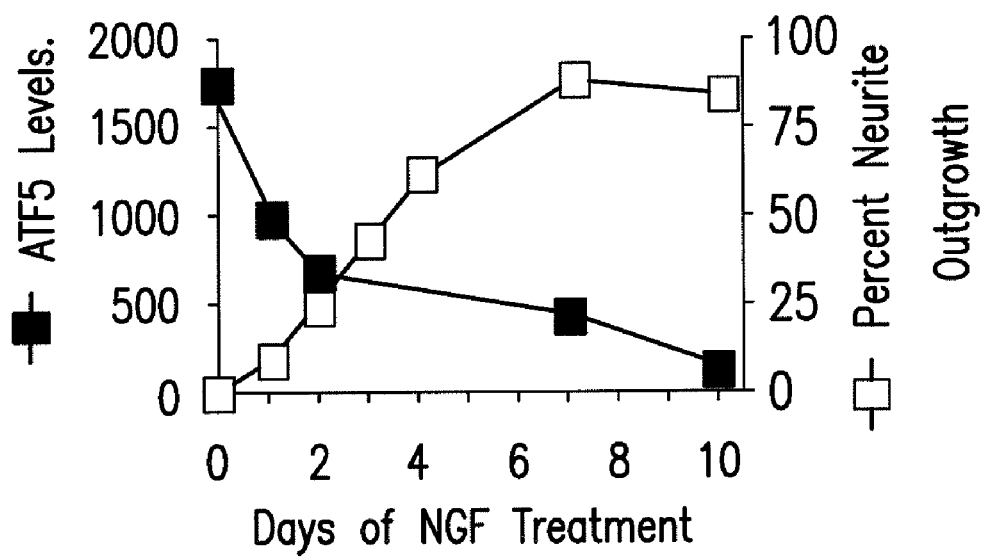

A time course of ATF5 protein expression in PC12 cells, in response to NGF treatment, revealed a drop in levels by 1 day, and a progressive fall thereafter, with relatively little detectable expression by day 10 (FIGS. 1A and 1B). Quantification of neurite outgrowth in the same sets of cultures revealed a reciprocal relationship with ATF5 expression (FIG. 1B).

Figure 2A:
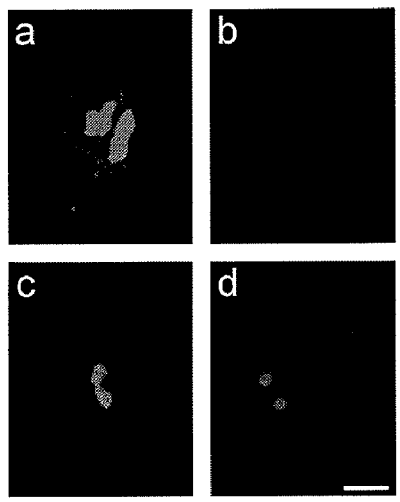
FIG. 2 shows that overexpression of ATF5 represses neurite outgrowth in PC12 cells, while NTAzip-ATF5 accelerates neuritogenesis. (A) Detection and NGF response of PC12 cells expressing exogenous ATF5. PC12 cells were transiently transfected with pCMS-eGFP (panels a and b) or pCMS-eGFP expressing FLAG-tagged ATF5 (panels c and d). Two days after transfection, the cultures were treated with NGF. Five days after transfection (i.e., after 3 days of NGF exposure), the cells were fixed and co-stained with rabbit anti-GFP (panels a and c) or mouse anti-FLAG antibody (panels b and d), with detection by FITC (GFP) and rhodamine-conjugated secondary antibody (FLAG-ATF5). Scale bar represents 50 μm (B) Quantification of the effects of exogenous ATF5 and of NTAzip-ATF5 on NGF-promoted neurite outgrowth. PC12 cells were transiently transfected with pCMS-eGFP, without insert or expressing FLAG-tagged ATF5 or FLAG-tagged NTAzip-ATF5. Two days after transfection, the cultures were treated with NGF. Cultures were fixed at the indicated times, after commencement of NGF exposure, and immunostained with anti-GFP and anti-FLAG, as above. Transfected cells (positive for FLAG and/or GFP staining) were assessed for the presence or absence of neurites. The proportions of transfected cells bearing neurites are reported ±SEM, with n=3 cultures (and at least 300 transfected cells assessed per culture). Comparable results were achieved in 4 additional independent experiments. In all cases (including the data shown), ANOVA analysis indicated a p value of <0.05 at the 72-h point of NGF treatment for eGFP vs. ATF5. (C) NTAzip accelerates NGF-promoted neurite outgrowth. Cultures were transfected, treated, and assessed as in (B), at 24 h after NGF exposure. Values represent the mean±SEM for results of 4 independent experiments. In each experiment, the data were normalized to the percentage of neurite-bearing cells transfected with pCMS-eGFP. The average percentage of such cells was 10.6±3.7. NTAzip vs. eGFP: p<0.02, Student's t-distribution test.
Figure 2B:
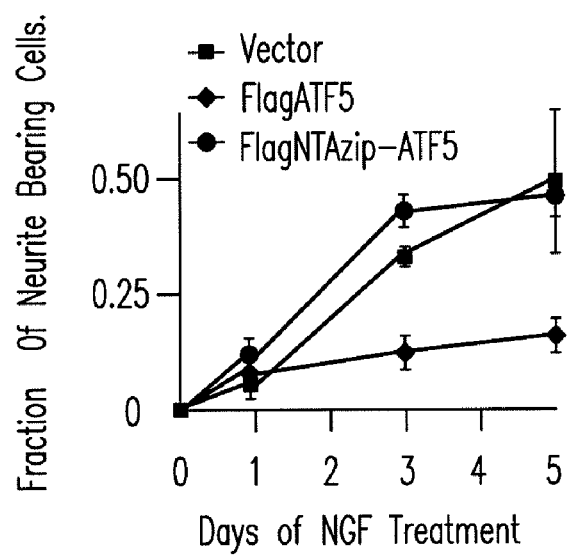

Exogenous ATF5 Represses NGF-Promoted Neurite Outgrowth, While a Dominant-Negative ATF5 Accelerates Initial Neuritogenesis The inverse behaviors of ATF5 expression and neurite outgrowth suggested a possible causal relationship. To test this, FLAG-tagged ATF5 was subcloned into the pCMS-eGFP vector, and transfected into PC12 cells. Two days later, NGF was added, and the transfected cells (expressing eGFP and tagged ATF5) were assessed over time for the appearance of neurites. In contrast to cells transfected with empty vector, those expressing exogenous ATF5 showed markedly repressed genesis of neurites over a 5-day time course (FIGS. 2A and 2B).

To assess the possibility that exogenous ATF5 might act, at least in part, by non-physiologically sequestering and "squelching" the actions of binding partners, the inventors also prepared a construct encoding an N-terminally-truncated form of FLAG-tagged ATF5, possessing an enhanced b-Zip domain (NTAzip-ATF5). This was achieved by deleting the N-terminal acidic activation domain, and replacing the DNA-binding domain with an amphipathic acidic α-helical sequence containing leucine repeats at each seventh residue.

Without activation and DNA-binding domains, NTAzip-ATF5 does not interact with DNA or directly affect gene transcription. However, because this protein includes the intact ATF5 leucine zipper, it retains specific interactions with endogenous ATF5 and with heterologous binding partners. In addition, the Azip amphipathic acidic α-helical domain should tightly associate with the basic DNA-interaction domains of ATF5-binding partners, thereby blocking their functions (Vinson et al., Dimerization specificity of the leucine zipper-containing bZIP motif on DNA binding: prediction and rational design. *Genes Dev.*, 7:1047-58, 1993; Krylov et al., Extending dimerization interfaces: the bZIP basic region can form a coiled coil. *EMBO J.*, 14:5329-37, 1995; Moitra et al., Life without white fat: a transgenic mouse. *Genes Dev.*, 12:3168-81, 1998; Moll et al., Attractive interhelical electrostatic interactions in the proline- and acidic-rich region (PAR) leucine zipper subfamily preclude heterodimerization with other basic leucine zipper subfamilies. *J. Biol. Chem.*, 275:34826-832, 2000). Thus, if exogenous ATF5 acts by non-specific squelching, rather than by binding to DNA, NTAzip-ATF5 should have a similar effect. However, in contrast to ATF5, NTAzip-ATF5 did not block NGF-promoted neurite outgrowth (FIG. 2B), thus ruling out a non-specific action of the former.

Figure 2C:
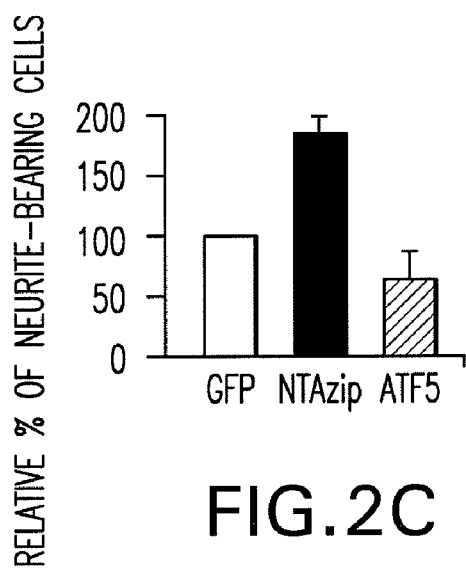

In addition to serving as a control for non-specific squelching, NTAzip-ATF5 acts as a dominant-negative for ATF5, thereby permitting evaluation of the consequences of ATF5 loss-of-function. In the absence of NGF, transfected NTAzip-ATF5 did not stimulate neurite outgrowth (data not shown). However, cells transfected with NTAzip-ATF5, and then exposed to NGF, showed a significantly faster (two-fold) initial appearance of neurites, as compared with controls (FIG. 2C). This reinforces the notion that a physiologic function of ATF5 is suppression of neurite outgrowth, and that its down-regulation is required for this process to occur. After the first 1-2 days of NGF treatment, the effect of NTAzip-ATF5 is much less apparent, presumably due to down-regulation of endogenous ATF5.

ATF5 is Highly Expressed in Ventricular Zones of Developing Brain

Figure 3A:
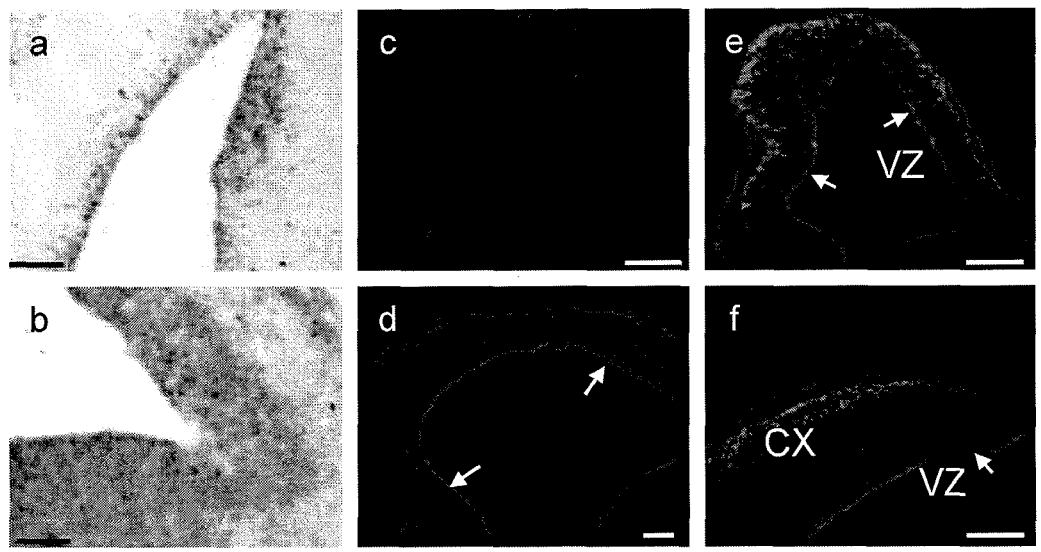
FIG. 3 illustrates that ATF5 is differentially expressed in the ventricular zones of E12-E15 rat brain. (A) Expression of ATF5 message in developing rat brain (panels a and b). In situ hybridization was carried out using an ATF5 antisense probe in saggital sections of E15 rat brain. Panel a shows the area around the fourth ventricle, and panel b shows the telencephalon. There was no positive signal with a control ATF5 sense probe. Expression of ATF5 protein is shown in coronal sections of E12 (panels c and d) and E14 (panels e and f) rat telencephalon. (panel c) Staining with pre-immune serum. (panels d-f) Co-staining with anti-ATF5 (red) and anti-tubulin β (III) (TUJ1 antibody; green). Arrows indicate staining of ATF5 in the ventricular zone (VZ). CX=cortex; scale bar for panel a represents 100 μm (B) High-power confocal images of reciprocal expression of ATF5 (red) and tubulin β (III) in coronal sections of E14 rat telencephalon. Immunochemical staining was carried out as in (A). Images showing the ventricular zone (panel a) and cortex (panel b) are from the same section, and were photographed in the same confocal Z-plane section (1.3 μm). Arrowhead shows a migratory cell undergoing a transition from a progenitor to a neuron, by exhibiting both ATF5 and tubulin β (III) staining. Co-localization was confirmed by YZ and XZ confocal images. Scale bar for panel B represents 20 μm.

The suppression of neurite outgrowth by ATF5 in PC12 cells, and the potential suitability of this system for modeling the transition of neural progenitor cells to differentiated post-mitotic neurons, led the inventors to examine expression of ATF5 in the developing nervous system. In situ hybridization revealed specific expression of ATF5 transcripts in E12-15 rat neural nasal epithelium (see, also, Hansen et al., Mouse Atf5: molecular cloning of two novel mRNAs, genomic organization, and odorant sensory neuron localization. *Genomics*, 80:344-50, 2002), dorsal root and trigeminal ganglia, and brain (FIG. 3 and data not shown). The only signal of comparable strength detected outside the nervous system at these stages was in liver (data not shown). Within E12-15 rat brain, expression was highest in the ventricular zone (VZ) of the neural epithelium adjacent to the lateral ventricles and the fourth ventricle—sites of intense proliferation of neural cell precursors—and was decreased in overlying structures containing migrating and post-mitotic neurons (FIG. 3A, panels a and b).

Figure 3B:
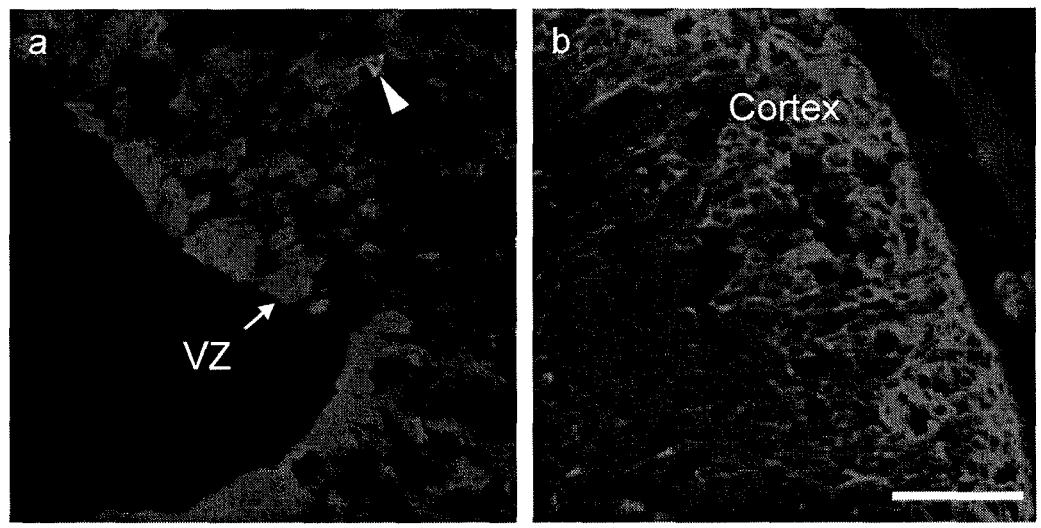
Figure 4:
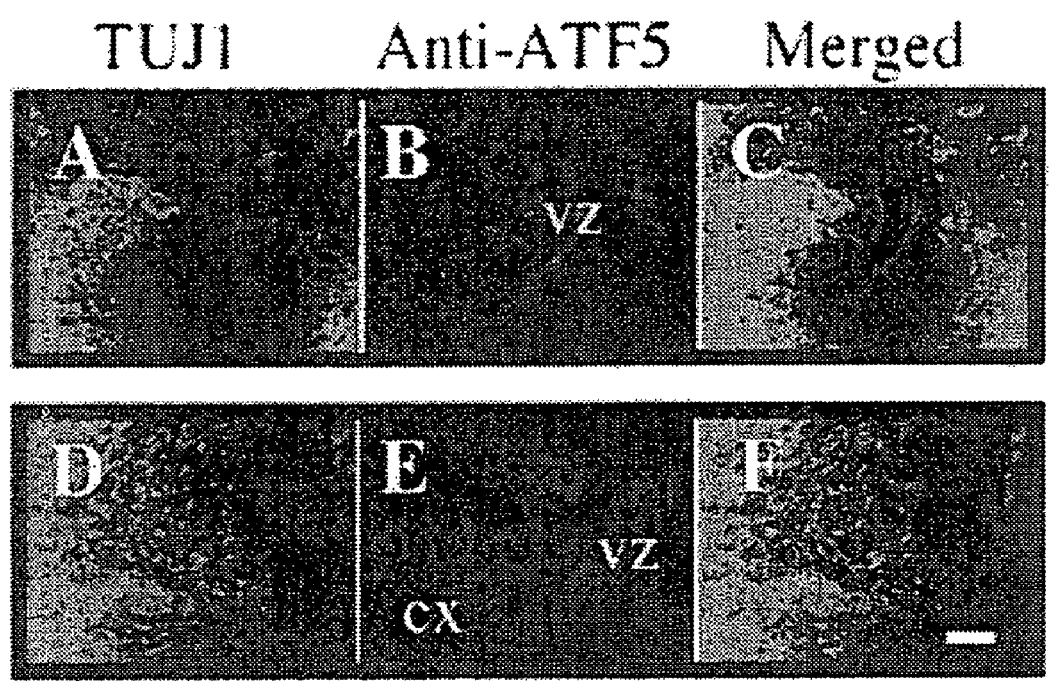
FIG. 4 demonstrates reciprocal expression of ATF5 and tubulin β (III) in E17 rat brain. (A-C) Expression of ATF5 (red) and tubulin β (III) (green) in the area of the anterior (A-C) and posterior (D-F) lateral ventricles of the E17 rat brain. Immunohistochemical staining was carried out as in FIG. 3 and the Examples. Scale bar represents 100 μm.

In view of the pattern of ATF5 transcripts in developing brain, the inventors next examined ATF5 protein expression in developing brain, using immunohistochemistry. ATF5 protein was strongly expressed in the VZ of E12 and E14 telencephalon, and fell to undetectable levels toward the surface of the developing cortex (FIG. 3A, panels c-f; FIG. 3B). Double staining with the TUJ1 antibody that recognizes tubulin βIII, a marker for post-mitotic neurons (Lee et al., Posttranslational modification of class III beta-tubulin. *Proc. Natl. Acad. Sci. USA*, 87:7195-99, 1 990), showed a converse pattern of staining (FIGS. 3A and 3B), indicating that ATF5 is highly expressed in proliferating neural progenitor cells and undetectable in differentiated neurons. A comparable pattern was also observed in E14 rat embryo telencephalon, at higher magnification, using confocal microscopy (FIG. 3B). At E17, ATF5 expression remained largely confined to the VZ, in contrast to the large expansion of TUJ1-positive staining in the cortical area (FIGS. 4A-4F).

Figure 5:
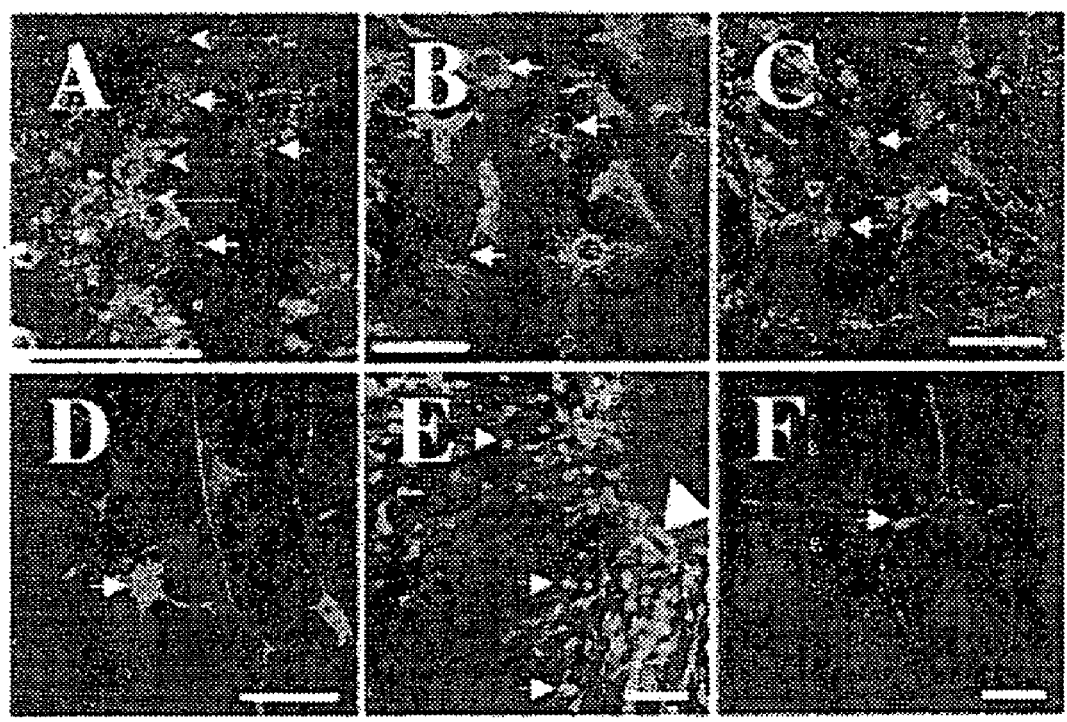
FIG. 5 shows that ATF5 is expressed in neural stem cells and progenitor cells, but not in mature neurons in attached neurosphere cultures. Attached clonal neurosphere cultures were established from the subventricular zone and hippocampal dentate gyrus of newborn mouse brain, and maintained as described in the Examples. Cultures were fixed and co-stained as follows: (A) ATF5 (red) and AC133 (green), a stem cell marker. Thick arrows show examples of nuclear staining, thin arrows show cytoplasmic staining. (B) ATF5 (red) and nestin (green), a marker for neural progenitor cells. Arrows indicate nuclear staining. (C, D) ATF5 (red) and NF-M (green), a marker for the neuronal lineage. Arrows show nuclear staining in (C) and cell body in (D). (E, F) ATF5 (red) and anti-tau (green), a neuronal marker. Comparable results were achieved in 10 independent experiments. Arrows show neurons at the periphery of the cultures; arrowhead shows stem and neural progenitor cells at the center of the culture. Stained cells were examined and photographed by confocal microscopy. The scale bar is 20 μm for (A), and 50 μm for (B-F).

ATF5 is a Marker For Neural Stem/Progenitor Cells, but not for Mature Neurons in Clonal Neural Progenitor Cell Cultures The above findings indicate that ATF5 is highly expressed in proliferating PC12 cells and in VZ progenitor cells, but not in post-mitotic neurons. To further examine the correlation between ATF5 expression and neuronal differentiation, the inventors prepared cultures of neural progenitor cells from the neurogenic subventricular zone or hippocampal dentate gyrus of newborn mouse brain. Clones derived from single-cell suspensions were expanded and cultured as neurospheres, under non-adherent conditions, in the presence of EGF, bFGF, and insulin, and then plated onto poly-L-ornithine and laminin, with 10% fetal bovine serum, to trigger substrate attachment and neurogenesis (Kukekov et al., Multipotent stem/progenitor cells with similar properties arise from two neurogenic regions of adult human brain. *Exp. Neurol.*, 156:333-44, 1999; Laywell et al., Identification of a multipotent astrocytic stem cell in the immature and adult mouse brain. *Proc. Natl. Acad. Sci. USA*, 97:13883-888, 2000). Cells at the centers of the cultured neurospheres proliferate as stem/progenitor cells, while those that migrate to the culture periphery differentiate into neurons and glia (FIG. 5E).

ATF5 expression was very high at the 3-dimensional core of the cultures. Co-staining with antibodies to the AC133 antigen, a marker for hematopoietic and neural stem cells (Yin et al., AC133, a novel marker for human hematopoietic stem and progenitor cells. *Blood*, 90:5002-12, 1997; Uchida et al., Direct isolation of human central nervous system stem cells. *Proc. Natl. Acad. Sci. USA*, 97:14720-25, 2000; Bhatia, AC133 expression in human stem cells. *Leukemia*, 15:1685-88, 2001; Yu et al., AC133-2, a novel isoform of human AC133 stem cell antigen. *J. Biol. Chem.*, 277:20711-716, 2002), revealed extensive co-expression with ATF5 in this region (FIG. 5A). AC133 antigen localization appeared to be largely at the cell surface and plasma membrane, while ATF5 appeared to be mainly localized to nuclei. ATF5 was also extensively expressed in cells positive for nestin (FIG. 5B), an intermediate filament expressed by neuroectodermal progenitors (Lendahl et al., CNS stem cells express a new class of intermediate filament protein. *Cell*, 60:585-95, 1990).

Co-localization experiments were also carried out with ATF5 and neuronal markers. The 160-kDa neurofilament protein, NF-M, was detected in cells outgrowing towards the culture periphery. A sub-population of such cells, which generally appeared to have short, neurite-like processes, co-stained for nuclear ATF5 (FIG. 5C). For such cells, staining of ATF5 and NF-M appeared to be of relatively low intensity, indicating that these were immature neuronal cells in transition with rising levels of NF-M expression and falling levels of ATF5. Another population of cells, with more advanced neuronal morphology, strongly stained for NF-M, but was negative for expression of ATF5 (FIG. 5D). Finally, co-staining with antiserum, for the neuronal marker, tau (Takemura et al., In situ localization of tau mRNA in developing rat brain. *Neuroscience*, 44:393-07, 1991), revealed a set of tau-positive cells, at the periphery of the cultures, with clear neuronal morphology (FIGS. 5E and 5F). Unlike the progenitor cells in the centers of the cultures, that were positive for ATF5 expression and negative for tau, the tau-positive cells in the periphery did not co-stain for ATF5. Taken together, these observations indicate that ATF5 is expressed in neural stem (AC133+) and progenitor (nestin+) cells, including those committed to the neuronal lineage, and are down-regulated in differentiated, post-mitotic neurons (tau+).

Figure 6A:
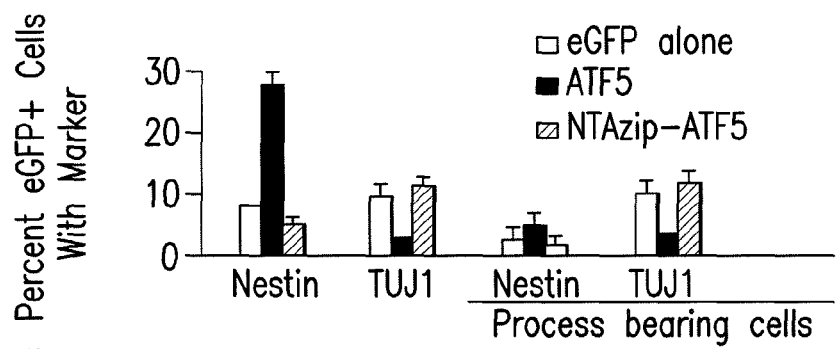
FIG. 6 illustrates that ATF5 represses, and NTAzip-ATF5 promotes, neurite outgrowth and expression of neuronal markers in neural progenitor cells. (A) Cultured E14 telencephalic cells were transiently transfected with pCMS-eGFP containing either no insert (empty vector), FLAG-ATF5, or NTAzip-ATF5. Three days following transfection, the cultures were fixed and co-immunostained for GFP and either nestin or tubulin β(III) (TUJ1 antibody). Transfected cells (GFP+) were assessed for the presence of neurite-like processes, and for co-expression of the indicated markers. Values represent the mean±SEM for 3 cultures in which at least 300 transfected cells were evaluated per culture. Comparable results were achieved in 4 independent experiments. ANOVA analysis of transfected cells: total cells—nestin/eGFP alone vs. nestin/ATF5, p<0.001; TUJ1/eGFP alone vs. TUJ1/ATF5, p<0.05; nestin/eGFP alone vs. nestin/NTAzip, and TUJ1/eGFP alone vs. TUJ1/NTAzip, no significant difference; process-bearing cells—TUJ1/GFP alone vs. TUJ1/ATF5, p<0.05; nestin/eGFP alone vs. nestin/NTAzip and TUJ1/eGFP alone vs. TUJ1/NTAzip, no significant difference. (B) Cultured E14 telencephalic cells were infected with retroviruses expressing eGFP or FLAG-ATF5 and eGFP. One week after infection, the cultures were fixed and assessed as in (A), and assessed for NF-M expression. Comparable results were achieved in 3 independent experiments. ANOVA analysis: total cells—nestin/eGFP alone vs. nestin/ATF5, p<0.001; TUJ1/GFP alone vs. TUJ1/ATF5, p<0.01; NFM/eGFP vs. NFM/ATF5, p<0.001; process-bearing cells—TUJ1/GFP alone vs. TUJ1/ATF5, p<0.001; NFM/GFP alone vs. NFM/ATF5, p<0.01; nestin/eGFP alone vs. nestin/ATF5, no significant difference; TUJ1 vs. NFM, no significance both with eGFP alone and with eGFP plus ATF5. (C) E14 telencephalon cells were infected with retroviruses expressing eGFP, eGFP and FLAG-ATF5, or eGFP-FLAG-NTAzip-ATF5. Four days after infection, the cultures were fixed and evaluated as in (A). Comparable results were achieved in 2 independent experiments. ANOVA analysis: nestin/GFP alone vs. nestin/ATF5, p<0.001; total and process-bearing cells—TUJ1/eGFP alone vs. TUJ1/ATF5, p<0.01; TUJ1/GFP alone vs. TUJ1/NTAzip, p<0.5. (D) Cultured E14 telencephalic cells were transiently transfected with pCMS-eGFP, with or without ATF5 siRNA. Four days following transfection, the cultures were fixed and co-immunostained either for GFP and TUJ1 antibody, or with GFP and ATF5 antiserum. Transfected cells (GFP+) were assessed for the presence of the neuronal marker, tubulin β(III) (TUJ1), or ATF5. Values represent the mean±SEM for six cultures in which at least 300 transfected cells were evaluated per culture. Comparable results were achieved in 3 independent experiments (two experiments with E14 telencephalon cells cultured with serum plus EGF and FGF2, and one experiment with only serum). ANOVA analysis: TUJ1/eGFP alone vs. TUJ1/ATF5 siRNA, p<0.001; ATF5/GFP alone vs. ATF5/ATF5 siRNA, p<0.001. (E) ATF5 suppresses NT3-promoted neuronal differentiation. E15 telencephalon cells were infected with retroviruses expressing eGFP, eGFP and FLAG-ATF5, or eGFP-FLAG-NTAzip-ATF5, all ±NT3. Four days after infection and maintenance ±NT3 treatment, the cultures were fixed and evaluated, as in (A), for eGFP and TUJ1 expression. Comparable results were achieved in 2 independent experiments. ANOVA analysis: −NT3/eGFP alone vs. +NT3/GFP alone, p<0.001; −NT3/eGFP alone vs. −NT3/ATF5, p<0.05; +NT3/eGFP alone vs. +NT3/ATF5, p<0.001; −NT3/eGFP alone vs. −NT3/NTAzip, p<0.001; +NT3/GFP alone vs. +NT3/NTAzip, no significant difference.

ATF5 Represses, but Dominant-Negative ATF5 and ATF5 Small Interfering RNA Accelerate, Neuronal Differentiation of Neural Progenitor Cells The above-described expression pattern of ATF5 raised the possibility that the presence of this protein, as in PC12 cells, may block proliferating neural progenitor cells from undergoing neuronal differentiation. To assess this, rat E14 telencephalic cell cultures containing a mixture of proliferating progenitor cells and post-mitotic neurons, and a small number of glial cells (Ghosh and Greenberg, Distinct roles for bFGF and NT-3 in the regulation of cortical neurogenesis. *Neuron*, 15:89-03, 1995), were transfected with pCMS-eGFP containing either no insert, FLAG-ATF5, or FLAG-NTAzip-ATF5. Transfected cells (identifiable by eGFP expression) were scored 3 days later for neuronal morphology and expression of nestin and tubulin βIII (FIG. 6A). In contrast with the cells transfected with empty vector, few cells transfected with ATF5 exhibited neuronal morphology.

In addition, ATF5 greatly repressed expression of the neuronal marker, tubulin βIII. On the other hand, ATF5 significantly increased the proportion of cells expressing nestin, a marker for neural progenitor cells. NTAzip-ATF5 did not mimic ATF5, ruling out a potential non-physiological squelching action of ATF5, as in the case of PC12 cells. In comparison with control transfectants, somewhat fewer cells transfected with NTAzip-ATF5 expressed nestin, although a greater number tended to express neuronal markers.

Figure 6B:
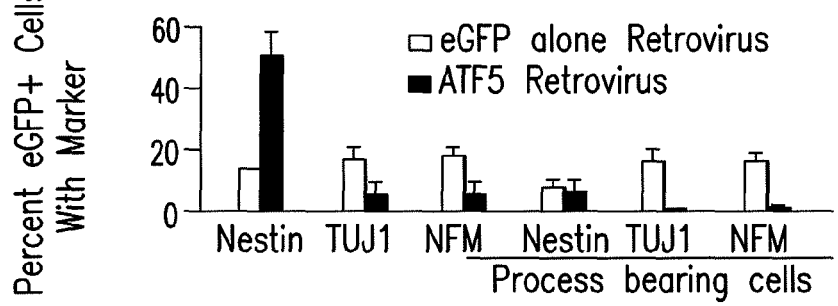
Figure 6C:
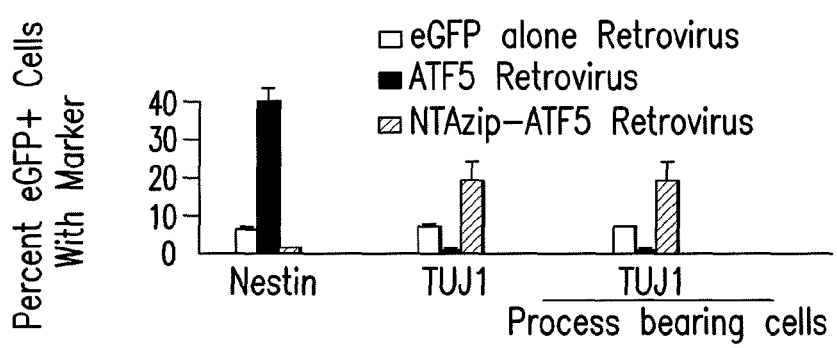

To ensure initial expression only in proliferating cells of the inventors' telencephalic cell cultures, and to permit transgene delivery at an early point after establishment of the cultures (which was technically unfeasible with the inventors' transfection conditions), the inventors constructed, and infected the cells at 1 day in vitro with, retroviral vectors expressing either eGFP, eGFP-FLAG-NTAzip-ATF5, or FLAG-ATF5 and eGFP. In this paradigm, ATF5 once again suppressed neurite outgrowth and expression of neuronal markers (NF-M and TUJ1), and led to an increase in proportion of nestin-positive cells at either 7 (FIG. 6B) or 4 (FIG. 6C) days after infection. Moreover, loss of function of endogenous ATF5, promoted by NTAzip-ATF5, significantly enhanced the genesis of neurite-bearing, TUJ1-positive cells in cultures assessed at 3 (data not shown) and 4 (FIG. 6C) days following viral exposure. The double-negative construct also promoted a fall in nestin positive cells, which presumably reflected the increase in neuronal differentiation. The increase in TUJ1-positive cells was greater than can be accounted for by the fall of nestin-positive cells, indicating either that the antibody the inventors employed led to an underestimation of the numbers of nestin-positive progenitor cells in the cultures, or that at least some neurons were generated from a population of nestin-expressing progenitors.

Figure 6D:
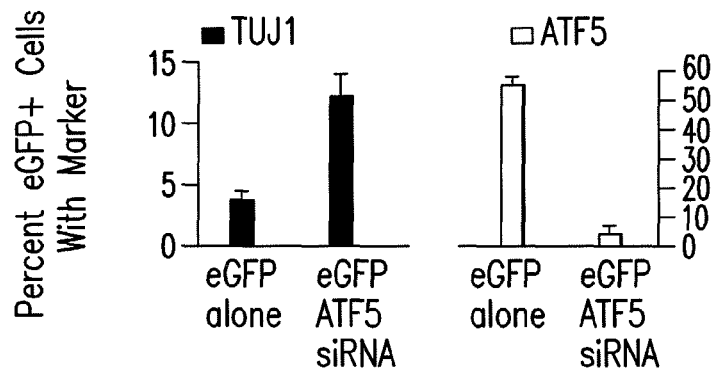

To corroborate the inventors' findings that NTAzip-ATF5 accelerates neurogenesis by specifically interfering with the function of endogenous ATF5, rather than through non-specific actions, the inventors employed small interfering RNA (siRNA) to selectively down-regulate endogenous ATF5. After 3 days in vitro, E14 telencephalic cells were transfected with GFP or with GFP plus ATF5 siRNA. On the fourth day after transfection with the siRNA, the proportion of transfected cells with detectable endogenous ATF5 fell by 96%, as compared with controls (FIG. 6D). Significantly, the reduction of endogenous ATF5 resulted in a 3.4-fold increase in neurogenesis, as judged by the appearance of TUJ1 staining (FIG. 6D) and neurite outgrowth (data not shown). In contrast, an irrelevant siRNA synthesized to target down-regulation of the protein, POSH, had no effect on development of neuronal markers or processes. Taken together, these findings support a model in which ATF5 suppresses the transition between neural progenitor cells and post-mitotic neurons, and in which loss of or interference with, ATF5 function accelerates neuronal differentiation.

Figure 6E:
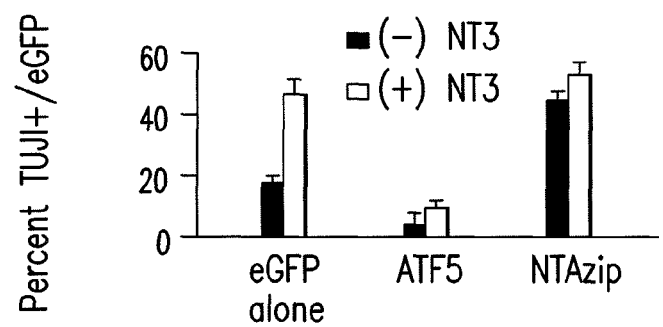

The limited degree of neuronal differentiation in the telencephalic cultures appears to occur in response to endogenous factors. To determine whether ATF5 can also regulate CNS neuronal differentiation promoted by a defined trophic agent, the inventors tested the effects of exogenous ATF5 and NTAzip-ATF5 in the presence and absence of NT3, a neurotrophin previously reported to drive telencephalic progenitor cell differentiation into neurons (Ghosh and Greenberg, Distinct roles for bFGF and NT-3 in the regulation of cortical neurogenesis. *Neuron*, 15:89-03, 1995). As shown in FIG. 6E, NT3 nearly tripled the level of neurogenesis in the cultures, and ATF5 suppressed this by 5- to 6-fold. Contrastingly, NTAzip-ATF5 had no significant effect on neurogenesis in the presence of NT3—unlike its marked promotion of neuronal differentiation in the absence of NT3. The latter observation would suggest that neuronal differentiation in the cultures is maximally stimulated by NT3, and cannot be further promoted by interfering with endogenous ATF5 activity. Furthermore, it appears that NT3 leads to down-regulation of endogenous ATF5, as none of the neurons formed in its presence exhibited detectable ATF5 immunostaining (data not shown). In conclusion, these findings indicate that, as in the case of NGF, NT3 promotes neurogenesis by a mechanism that can be suppressed by exogenous ATF5, and which includes loss of endogenous ATF5 expression.

Inhibition of Neurite Outgrowth by ATF5 Involves Repression of CRE Transactivation The work of Peters et al. (ATF-7, a novel bZIP protein, interacts with the PRL-1 protein-tyrosine phosphatase. *J. Biol. Chem.*, 276:13718-26, 2001) has established that ATF5 homodimers specifically bind to CRE elements, and that there is evidence that CRE plays an important role in neuronal differentiation and maintenance (Finkbeiner et al., CREB: a major mediator of neuronal neurotrophin responses. *Neuron*, 19:1031-47, 1997). Hence, the inventors next determined whether ATF5 regulates CRE activity in neuronal cells, and whether this action plays a role in ATF5-mediated suppression of neuronal differentiation.

The inventors also wished to determine whether the presence of NGF would affect the capacity of ATF5 to regulate CRE activity. Accordingly, PC12 cells were co-transfected with a CRE-luciferase reporter construct, a lacZ expression construct (for normalization of transfection efficiency), and pCMS-eGFP containing either no insert, FLAG-ATF5, or FLAG-NTAzip-ATF5. One day later, the cells were harvested and assessed for reporter activity. A portion of the cultures were treated with NGF for 2 days prior to, and during, the 24 h after transfection (3-day NGF treatment); others were either unexposed to NGF, or exposed to the factor at the time of transfection (1-day NGF treatment) or during the last hour before harvesting (1-h NGF treatment).

Figure 7A:
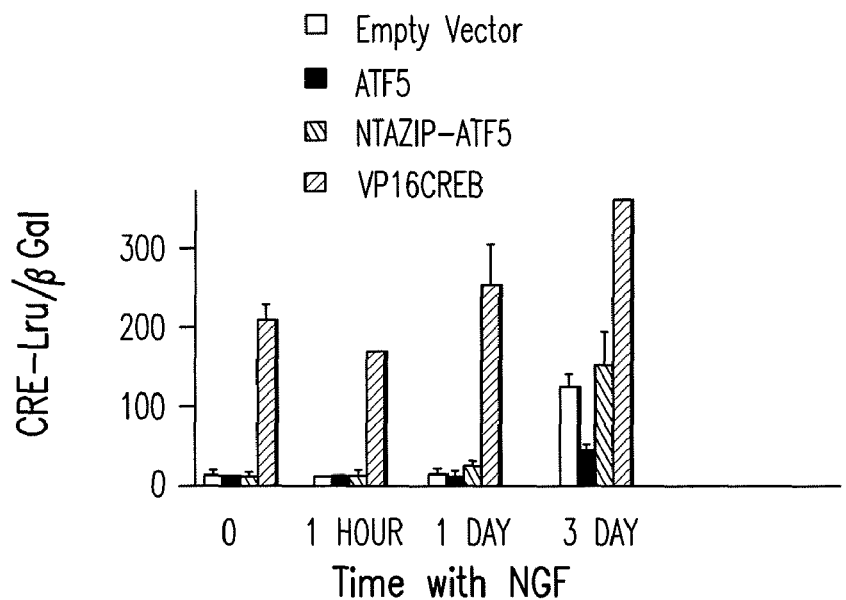
FIG. 7 demonstrates that NTAzip-ATF5 and VP16-CREB reverse ATF5-promoted repression of CRE-mediated gene expression and of neurite outgrowth. (A) PC12 cells were co-transfected with pG13-CRE luciferase, pcDNA-LacZ, and 1 µg/culture of pCMS-eGFP expressing either no insert (empty vector), FLAG-ATF5, FLAG-NTAzip-ATF5, or VP16-CREB. The cultures were also exposed to NGF for 2 days prior to and during the time of transfection (for a total of 3 days), during the time of transfection (1 day), or during the last hour prior to harvesting. One day after transfection, the cells were harvested and assessed for luciferase expression and LacZ activity (β-GAL). Values represent mean normalized CRE-luciferase activity (in arbitrary units)±SEM (n=3). Comparable results were achieved in three independent experiments. Student's t-distribution test: empty vector (eGFP alone) vs. VP16CREB at all times, p<0.001; GFP alone vs. ATF5, p<0.033 by day 3. (B) PC12 cells were co-transfected with pG13-CRE luciferase, pcDNA-LacZ, and the indicated combinations of pCMS-eGFP expressing either no insert (GFP), FLAG-ATF5 (ATF5), FLAG-NTAzip-ATF5 (AZIP), or VP16-CREB. The latter vectors were each used at 0.5 µg/culture, and empty vector was added, as needed, to bring the total DNA level to 1 µg/culture. Cultures were harvested 1 day later, or assayed for luciferase expression and LacZ activity (β-GAL). Where indicated, NGF was added to the medium 1 h before harvesting. Values represent mean normalized CRE-luciferase activity (in arbitrary units) ±SEM (n=6), with data pooled from 2 independent experiments. Student's t-distribution test: −NGF-eGFP alone vs. ATF5, p<0.003; eGFP alone vs. NTAzip, p<0.0003; eGFP alone vs. ATF5/NTAzip, no significant difference; eGFP alone vs. VP16CREB and VP16CREB/ATF5, p<0.0001; +NGF-eGFP alone vs. ATF5, p<0.0001; eGFP alone vs. NTAzip, p<0.02; eGFP alone vs. ATF5/NTAzip, p<0.02; eGFP alone vs. VP16CREB and VP16CREB/ATF5, p<0.0001. (C) PC12 cells were co-transfected with the indicated constructs, and NGF was added to the medium 2 days later. Transfected cells (identified for eGFP) were assessed for neurite outgrowth at the indicated times. Values represent means±SEM of results for 3 cultures in which at least 300 transfected cells were scored per culture. Comparable results were obtained in 2 independent experiments. ANOVA analysis after 72 h of NGF-treatment: eGFP alone vs. ATF5, eGFP p<0.001; eGFP alone vs. NTAzip-ATF5, NTAzip/ATF5, Vp16CREB, or Vp16CREB/ATF5, no significant difference.

Without NGF treatment, or after 1 h of NGF treatment, there was relatively little constitutive CRE transactivation. The effect of exogenous ATF5 was somewhat variable at this time, with suppression of activity in some experiments and not others (FIGS. 7A and 7B), possibly reflecting cell-culture conditions. At 1 day with NGF, there was a small (50%), but statistically significant, increase in CRE activity, in comparison with naïve cells; this was reduced to baseline by exogenous ATF5. At day 3, there was a 10-fold increase in CRE reporter activity, as compared with untreated cells, and this was again substantially reduced by exogenous ATF5. NTAzip-ATF5 did not reduce CRE activity, thereby making it unlikely that ATF5 interferes with CRE transactivation by non-physiologic interaction with CRE-regulatory proteins. Moreover, neither ATF5 nor NTAzip-ATF5 expression suppressed expression of a SRE reporter (data not shown). In addition to establishing that ATF5 suppresses CRE transactivation in intact neuronal cells, these findings indicate that NGF elevates basal CRE activity, and that this occurs at a time when endogenous ATF5 levels have fallen by about ⅔ (FIG. 1).

Figure 7B:
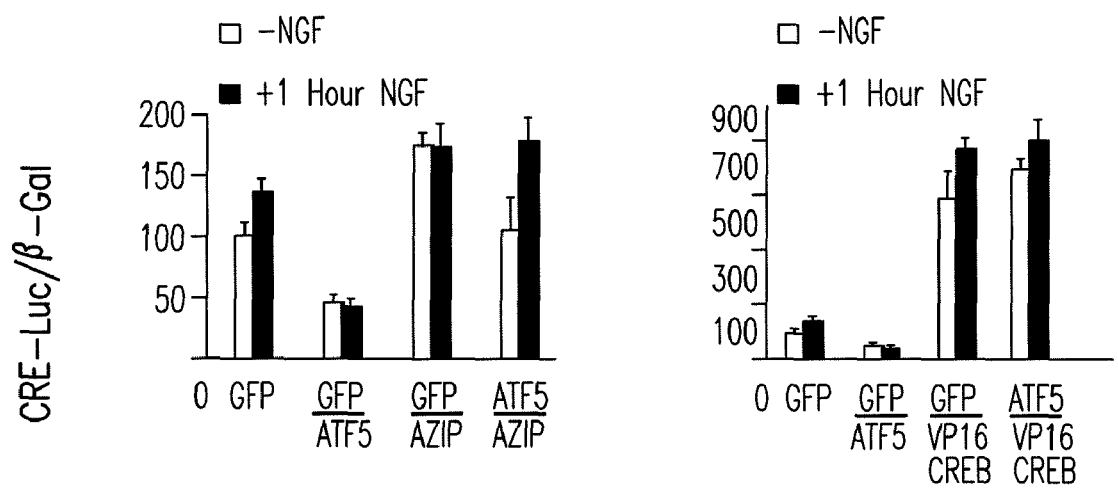
Figure 7C:
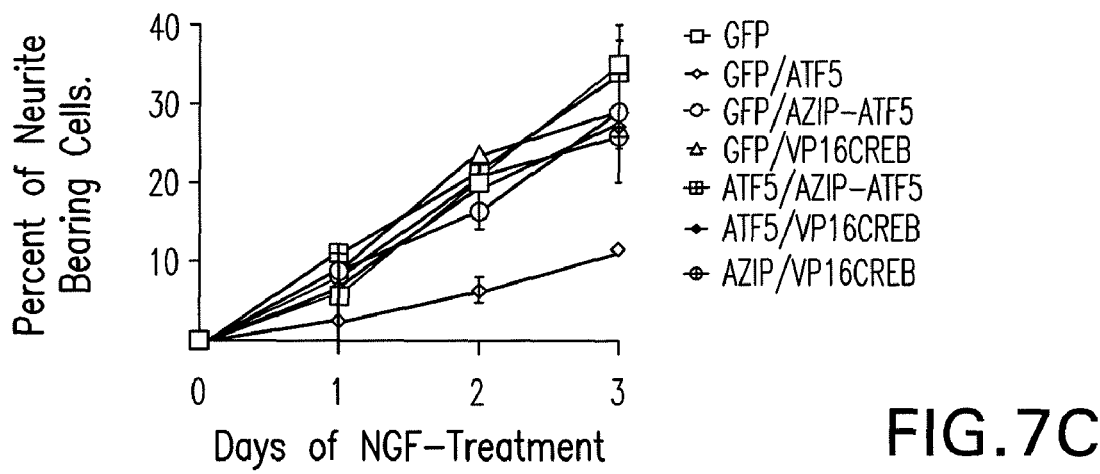

If ATF5 suppresses neuronal differentiation by binding to CRE and inhibiting its transactivation, then one might predict that this action should be reversed, either by a dominant-negative ATF5 protein without DNA binding or activation sites, or by a strong competitive CRE activator. The former characteristics are fulfilled by NTAzip-ATF5, which should form tight heterodimers with ATF5, but does not bind DNA. In support of the inventors' hypothesis, co-expression of NTAzip-ATF5 blocked inhibition of CRE reporter activity by ATF5 (FIG. 7B), and reversed ATF5-dependent suppression of NGF-promoted neurite outgrowth (FIG. 7C).

With respect to a competitive CRE activator, the inventors employed VP16-CREB, a constitutively-active form of the CRE-binding protein, CREB (Lu et al., The herpesvirus transactivator VP16 mimics a human basic domain leucine zipper protein, luman, in its interaction with HCF. *J. Virol.*, 72:6291-97, 1998; Barco et al., Expression of constitutively active CREB protein facilitates the late phase of long-term potentiation by enhancing synaptic capture. Cell, 108:689-03, 2002). Co-transfection of pCMS-eGFP-VP16-CREB into PC12 cells produced strong transactivation of the CRE reporter (FIG. 7A), and this was essentially unaffected by the additional co-transfection of FLAG-ATF5 (FIG. 7B).

The inventors next assessed whether driving CRE with VP16-CREB would reverse the actions of ATF5 on neurite outgrowth. Transfection of PC12 cells with pCMS-eGFP-VP16-CREB alone did not elicit neurite outgrowth in the absence of NGF, and, as in the case of FLAG-NTAzip-ATF5, enhanced the initial rate of neuritogenesis in the presence of NGF (FIG. 7C). Significantly, co-transfection of VP16-CREB, along with FLAG-ATF5, reversed the suppression of NGF-stimulated neurite outgrowth that was achieved with ATF5 alone (FIG. 7C). Taken together, these findings further support a model in which CRE transactivation is required for neuronal differentiation, but is reversibly blocked by ATF5.

Regulation of Endogenous ATF5 Protein in PC12 Cells and Neural Progenitor Cells

In consonance with their past observations of ATF5 transcripts, the inventors found that ATF5 protein is expressed in PC12 cells, and drops to nearly undetectable levels during NGF-promoted neuronal differentiation. Similarly, both ATF5 transcripts and protein are highly expressed in neural progenitor cells, and absent from post-mitotic neurons. The observed decrease in ATF5 protein expression most likely reflects the down-regulation of ATF5 transcripts. ATF5 has been reported to be a substrate for ubiquitin-conjugating enzymes, including Cdc34 (Pati et al., Human Cdc34 and Rad6B ubiquitin-conjugating enzymes target repressors of cyclic AMP-induced transcription for proteolysis. *Mol. Cell Biol.*, 19:5001-13, 1999); thus, it is likely to have a relatively rapid turnover that would produce efficient loss of expression following transcriptional down-regulation.

Western immunoblotting permitted the inventors to deduce the major cellular form of ATF5 protein. The ATF5 cDNA sequence predicts two potential in-frame methionine start sites that would lead to proteins of approximately 30 and 20 kDa. The inventors' observation that the major form of ATF5 in cells has an apparent molecular mass of 20-22 kDa indicates favored utilization of the second site. When a canonical Kozak initiation consensus sequence was included upstream of the first methionine, the larger protein was expressed (data not shown), thereby indicating that the 22-kDa form is not formed by cleavage of a 30-kDa precursor.

ATF5 Represses Neuronal Differentiation of Neural Progenitor Cells

The down-regulation of ATF5 expression by NGF in PC12 cells, the progressive loss of ATF5 expression that occurs as cells leave the ventricular zone and enter the developing cortex, and the presence of ATF5 in neural stem and progenitor cells, but not in well-differentiated neurons in neurosphere cultures, suggested to the inventors that this factor may play a causal role in regulating neuronal differentiation. In support of this supposition, exogenous ATF5 suppressed both neurite outgrowth in PC12 cell cultures and differentiation of cultured neural progenitor cells. Conversely, loss of ATF5 function (evoked by NTAzip, an ATF5 dominant-negative) nearly doubled the initial rate of NGF-promoted neuritogenesis by PC12 cells, and significantly enhanced neurogenesis in telencephalic cell cultures. In particular, an ATF5 siRNA that effectively reduced endogenous ATF5 levels also promoted a 3.6-fold enhancement of neurogenesis by cultured telencephalic cells.

The effect of exogenous ATF5 does not appear to be limited solely to neurite outgrowth, as virally-induced ATF5 expression in proliferating progenitor cells also blocked the appearance of several neuronal markers and led to an increase in numbers of cells that expressed nestin—a marker for neural progenitor cells. The increase in numbers of nestin-positive cells induced by exogenous ATF5 appeared to be greater than could be accounted for merely by simply blocking progenitor-cell differentiation. One possible explanation is that nestin-positive cells expressing exogenous ATF5 continued to proliferate, instead of leaving the cell cycle and differentiating.

Taken together, the inventors' observations with developing rat brain and neurosphere cultures indicate a scenario in which ATF5 is highly expressed in neural stem cells and neuroprogenitor cells, and suppresses their differentiation. The action of appropriate neurotrophic factors leads to down-regulation of ATF5, thereby permitting differentiation of neural progenitor cells into neurons. Therefore, the inventors' present findings suggest that ATF5 acts in a permissive, rather than instructional, manner, in that it does not appear to play a role in directly specifying cell fate per se; rather, it appears to act as a negative suppressor that must be down-regulated to permit the transition of neural progenitor cells to neurons. In this role, ATF5 would function to prevent stem cells and progenitor cells from undergoing terminal differentiation until stimulated by appropriate neurotrophic agents.

Further support for the notion that ATF5 acts as a negative permissive regulator, rather than as an instructional factor, comes from the inventors' observations with NTAzip-ATF5. This modified form of ATF5 should act as a dominant-negative that prevents interaction of ATF5 with DNA as well as with other potential protein-binding partners. This is borne out by the capacity of NTAzip-ATF5 to reverse the effect of ATF5 on CRE reporter activity. Nevertheless, when expressed in PC12 cells, NTAzip did not promote neurite outgrowth in the absence of NGF. Thus, although ATF5 down-regulation appears to be necessary for neuronal differentiation, loss of ATF5 activity does not appear to be sufficient to promote this process. Factors such as NGF appear to down-regulate negative permissive agents such as ATF5 and to provide instructional information that actively promotes neuronal differentiation. In the CNS neuroprogenitor cultures employed herein, down-regulation and instructional activity were likely to be supplied by endogenously-synthesized and released factors, such as NT3 and BDNF (Ghosh and Greenberg, Distinct roles for bFGF and NT-3 in the regulation of cortical neurogenesis. *Neuron,* 15:89-03, 1995).

The expression pattern of NGF during embryogenesis makes it unlikely that this factor is a key regulator of ATF5 expression in developing brain. However, many other potential neurotrophic factors are present there that could fulfill a similar role. For instance, BDNF and NT3, and their cognate receptors, TrkB and TrkC, are present in rat ventricular progenitor cells at E13 and E15 (Fukumitsu et al., Simultaneous expression of brain-derived neurotrophic factor and neurotrophin-3 in Cajal-Retzius, subplate and ventricular progenitor cells during early development stages of the rat cerebral cortex. *Neuroscience,* 84:115-27, 1998). BDNF (Ahmed et al., BDNF enhances the differentiation but not the survival of CNS stem cell-derived neuronal precursors. *J. Neurosci.,* 15:5765-78, 1995) and NT3 (Ghosh and Greenberg, Distinct roles for bFGF and NT-3 in the regulation of cortical neurogenesis. *Neuron,* 15:89-03, 1995) promote differentiation of cultured neuronal progenitor cells.

The inventors' experiments were focused on neuronal differentiation, and did not establish whether ATF5 also affects glial cell differentiation. However, the following evidence suggests that ATF5 may also be a negative regulator of astrocyte differentiation: the localization of ATF5 in brain areas that also give rise to glial progenitor cells; the co-localization of ATF5 with nestin, which is present in progenitor cells for both neurons and glia; and the inventors' preliminary observations that ATF5 co-localizes with GFAP in neuroprogenitor cell cultures and that exogenous ATF5 suppresses GFAP expression. Although ATF5 expression negatively correlates with neuronal differentiation, this may not be the case universally for differentiation of other cell types. Peters et al. (ATF-7, a novel bZIP protein, interacts with the PRL-1 protein-tyrosine phosphatase. *J. Biol. Chem.,* 276:13718-26, 2001) reported that ATF5 transcripts were markedly elevated when human Caco-2 cells reached confluency and spontaneously differentiated into a brush-border-bearing polarized cell layer.

Suppression of Neuronal Differentiation by ATF5 Involves CRE

Based on reports that ATF5 homodimers bind CRE, but not C/EBP or AP1, sites (Peters et al., ATF-7, a novel bZIP protein, interacts with the PRL-1 protein-tyrosine phosphatase. *J. Biol. Chem.,* 276:13718-726, 2001), and that ATF5 represses cAMP-mediated activation of a CRE reporter in JEG3 cells (Pati et al., Human Cdc34 and Rad6B ubiquitin-conjugating enzymes target repressors of cyclic AMP-induced transcription for proteolysis. *Mol. Cell Biol.,* 19:5001-13, 1999), the inventors examined the effect of ATF5 on the activity of a CRE reporter in PC12 cells. The inventors' findings confirm that ATF5 suppresses cellular CRE transactivation. As discussed above, it is significant that NTAzip-ATF5 did not mimic the suppressive actions of ATF5 on neurite outgrowth and CRE activity; rather, it antagonized these effects, thereby indicating that ATF5 acts by binding to DNA, instead of by non-specific "squelching" of binding partners.

The inventors observed that basal CRE activity substantially increased by 3 days of NGF treatment. One potential cause for this is the concurrent fall in endogenous ATF5 expression, and subsequent loss of ATF5-mediated CRE repression; however, the inventors cannot rule out the possibility that NGF regulates additional proteins that affect CRE activity.

Although NTAzip-ATF5 blocked the inhibitory effects of exogenous ATF5 on its own, it had no, or relatively little, effect on CRE reporter activity. If, as the inventors propose, CRE-dependent gene activation is suppressed by endogenous ATF5, then it might have been anticipated that basal CRE activation would be elevated in response to NTAzip-ATF5. Since this was not the case, this raises the possibility that one or more factors, in addition to ATF5, act to suppress CRE in neural progenitor cells, and that these are also down-regulated during neuronal differentiation.

To assess whether interference with CRE-mediated gene regulation might account for the mechanism by which ATF5 interferes with neuronal differentiation, the inventors co-expressed it with VP16-CREB, a constitutively-active fusion protein that includes the CREB DNA-binding domain and transactivation domain of the HSV VP16 protein. VP16-CREB potently activated the CRE reporter, and this effect was not blocked by co-expression of ATF5. Significantly, co-expressed VP16-CREB overrode ATF5-mediated inhibition of neurite outgrowth. This finding supports a model in which neuronal differentiation requires CRE-mediated gene activation, and in which such activation is repressed in neural progenitor cells by factors such as ATF5. In this light, it is of interest that PACAP, a potent activator of adenylate cyclase, promotes mitotic exit and neuronal differentiation of cultured cortical neuron precursor cells (Dicicco-Bloom et al., The PACAP ligand/receptor system regulates cerebral cortical neurogenesis. *Ann. N Y. Acad. Sci.,* 865:274-89, 1998), and that NGF-promoted differentiation of PC12 cells is synergized by cell-permeant cAMP derivatives (Gunning et al., Differential and synergistic actions of nerve growth factor and cyclic AMP in PC12 cells. *J. Cell Biol.,* 89:240-45, 1981).

In summary, the inventors' findings indicate that both positive and negative regulators govern the transition of neural progenitor cells to neurons. On one hand, ATF5 is highly expressed in neural stem cells and neuroprogenitor cells, and suppresses their neuronal differentiation, apparently by competing for binding to CREs. On the other hand, neuronal differentiation is accompanied by, and appears to require, down-regulation of ATF5 expression. This can be accomplished by neurotrophic factors such as NGF and NT3. Though such down-regulation may be necessary, it is not sufficient to permit neuronal differentiation. The latter also appears to require instructive signals that may be imparted by neurotrophic factors and/or activators of adenylate cyclase.

Example 2

Materials and Methods

Reagents

Cell culture medium DMEM, molecular biology reagents and LipofectAMINE 2000 were from Invitrogen, Inc. Fetal bovine serum was from JRH Biosciences. Mouse monoclonal anti-GFP IgG$_1$ was from Sigma. Goat anti-mouse Alexa 488, Alexa 568, goat anti-mouse IgG$_{2a}$ Alexa 488, goat anti-mouse IgG$_1$ Alexa 568, goat anti-rabbit Alexa 488 and 568, and mouse IgG$_{2a}$ anti-GFP antibody were from Molecular Probes. Rabbit anti-GFP antibody was from BD Biosciences (Clontech). Rabbit anti-Ki67 was from Novacastra. Normal 10% goat-serum was from Zymed. Polyclonal rabbit anti-ATF5 was as previously described (7).

Immunostaining of human glioblastomas

Paraffin sections (10 µm) of surgically excised glioblastoma multiforme tumors (WHO, Grade IV) were provided by the Department of Pathology, Columbia University. Paraffin was removed by heating the sections at 60° C. for one to two hours followed by 3 incubations in 100% xylene for 5 min each. Subsequent incubations were in 100%, 95%, 75% and 50% and 0% ethanol for 5 min each. The sections were then subjected to antigen retrieval by incubation in 10 mM citrate buffer (pH=6.0) at 100° C. in a Black & Decker HS 800 steamer for 40 min. Endogenous peroxidase was blocked by incubation with 0.3% hydrogen peroxide for 10 min followed by 3 washes in water. The tissue was then permeabilized by incubation with 0.04% Tween 20 in TBS (3× for 5 min each) and immunostained with ATF5 antiserum (1:600) in PBS containing 1% BSA for one hour at room temperature. Visualization was achieved with DAB reagent following the manufacturer's protocol (DAKO, Envision System kit). The sections were counterstained with light hematoxylin to reveal nuclei and cellular morphology. Antiserum against the Ki67 antigen (1:1000) was used as a positive immunostaining control.

Cell Culture

Glioma cell lines rat C6 (13) and RG2 (14), and human U87 (15), U373 (15), U251 (15), T98 (16), U138 (15), and DBTRG-05 (17) were grown in DMEM medium supplemented with 10% fetal bovine serum. Cells were passaged into 24-well culture dishes for transfections. Primary astrocytes were obtained by the method of Levison and McCarthy (18) and were passaged up to 5 times with trypsin and grown in DMEM medium plus 10% fetal bovine serum.

Transient Transfections pLeGFP mock, pLeGFPfusionFlag-Tagged-NTAzip-ATF5, pSIREN-RetroQ-ZsGreen encoding 21 bp complementary hairpin loop-siRNA Luciferase mock control and pSIREN-RetroQ-ZsGreen-U 21 bp complementary hairpin loop-siRNA rat ATF5 (GATCCGTCAGCTGCTCTCAGG-TACTTCAAGAGAGTACCTGAGAGCAGCTGACCTTTT TTCTAGAG (SEQ ID NO:17) were transfected into cell monolayers in 24-well dishes using 1 µg of plasmid/well and 2 µl/well of LipofectAMINE 2000 for 9 hours, after which time the cells were re-fed with fresh culture medium.

For transient transfections of oligo ribonucleotide duplexes, 80 pmole/well of ATF5 siRNA ($AAN_{19}$; rat AAG UCA GCU GCU CUC AGG UAC (SEQ ID NO:18) or human AAG UCG GCG GCU CUG AGG UAC) (SEQ ID NO:19) oligo ribonucleotide duplexes (Qiagen) and 1 µg/well of pCMS-EGFP vector were incubated with cells in 100 µl of DMEM medium and 2 µl/well of LipofectAMINE 2000 for 9 hours followed by an exchange of medium. For the control, cells were transfected with pCMS-EGFP vector alone.

In Vivo Induction of Atf5 Loss-of-Function

Non-replicating retroviruses encoding eGFP or Flag-Tagged-NTAzip-ATF5 were prepared as previously described (Angelastro, et al. Regulated expression of ATF5 is required for the progression of neural progenitor cells to neurons. *J. Neurosci.,* 23: 4590-4600, 2003). Adult rats were deeply anesthetized using ketamine and xylazine, and access to the brain was achieved by drilling a 0.5 mm diameter hole into the skulls of the animals 1 mm anterior and 3 mm lateral to the bregma on the right side and stereotactically injecting cells $1\times10^4$ in 5 µl and at a depth of 3.5 mm. After 10 days of tumor growth, the retroviruses ($1.25\times10^4$ CFU in 5 µl) was stereotactically injected into the growing tumors, using the same coordinates. Three days later, the rats were deeply anesthetized using ketamine and xylazine and were perfused transcardially with PBS, which was followed by 4% paraformaldehyde in PBS. The brains were removed and were post-fixed overnight in 4% paraformaldehyde, and were subsequently cryoprotected in 30% sucrose for two days. The brains were frozen in O.C.T. compound (Tissue-TEK) and then cryosectioned (10 µm coronal sections). Sections were stained for TUNEL following the manufacturer's protocol (Roche in Situ Cell Death Detection Kit, TMR Red, Cat. No. 2 156 792). The sections were blocked overnight at 4° C. with 10% goat serum in PBS containing 0.3% Triton X-100 (PBS-T) and then incubated overnight at 4° C. with rabbit anti-GFP antibody (1:500, Clontech) in PBS-T. After washing with PBS-T, the sections were then immunostained with goat anti-rabbit Alexa 488 secondary antibody (1:1000) for 2 hr at room temperature and then washed with PBS-T. Nuclei were stained with Hoechst dye 33342 (1 µg/ml) for 5 min and the sections were coverslipped with Gel/mount slide mounting medium.

Quantitative Assessment of Cell Death

Transfected cell cultures were fixed and immunostained for the expression of eGFP as previously described Angelastro et al. (Angelastro, et al. Regulated expression of ATF5 is required for the progression of neural progenitor cells to neurons. *J. Neurosci.,* 23: 4590-4600, 2003) and then incubated with Hoechst dye 33342 at 1 µg/ml in PBS and 0.3% Triton X-100 for 5 min at room temperature to detect apoptotic nuclei (Angelastro, et al. Characterization of a novel isoform of caspase-9 that inhibits apoptosis. *J. Biol. Chem.,* 276: 12190-12200, 2001). eGFP+ cells possessing condensed nuclei and fragmented chromatin were scored as apoptotic. For brain sections, eGFP+ cells were located and scored for the presence or absence of TUNEL labeling. Only cells with TUNEL positive nuclei (as indicated by co-staining with Hoechst dye 33342) were scored. Tumors were well demarcated and examination of the sections by phase microscopy and with respect to nuclear staining indicated whether cells were within or outside of the margins of the tumors. Separate staining of additional sections for either eGFP or TUNEL alone revealed no cross-over of signals. This was also verified in the double-stained sections by the presence of cells that were either TUNEL+ and eGFP− or vice versa.

Human Glioblastomas Express Nuclear ATF5

Figure 10:
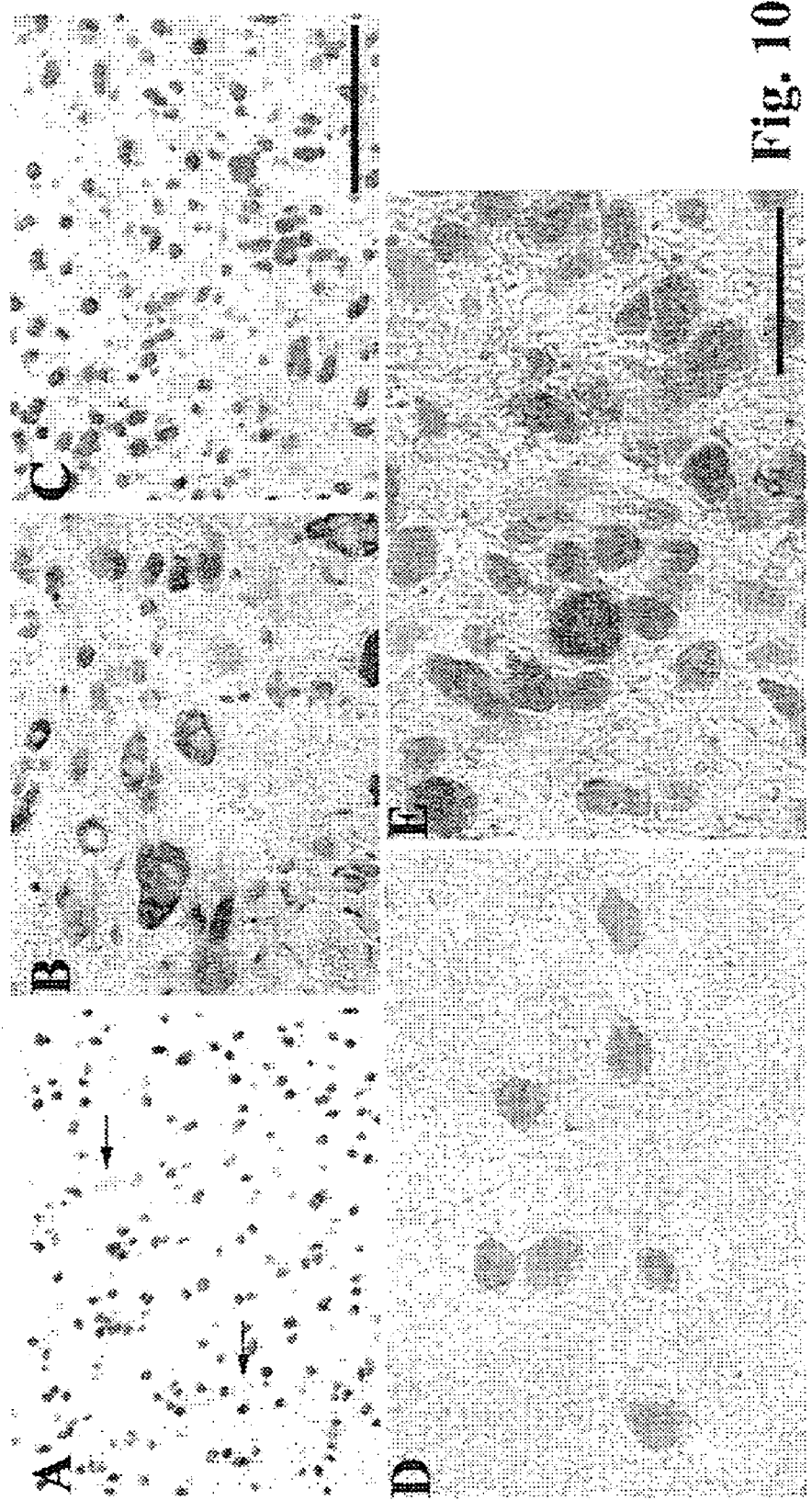
FIG. 10 shows expression of ATF5 in human glioblastomas. Examples of immunostaining for ATF5 (brown DAB product) in paraffin sections within (A-C, E) and outside of (D) Grade IV glioblastomas. (A) Arrows show the nuclei of neurons lacking positive ATF5 staining. In contrast, many of the surrounding nuclei of glioblastoma cells stain positively for ATF5. (B,C) Nuclear ATF5 staining in a giant-cell GBM (B) and in another GBM with variably-sized nuclei. (D,E) In sections from another patient, ATF5 staining is absent cells in the cortex outside the area of tumor infiltration (D), but present within the tumor (E). Scale bar is 10 µM for A-C, and 2 µm for D and E.

As discussed above, proliferative neural progenitor cells express high levels of nuclear ATF5 whereas mature neurons and glia express little or no detectable levels of this protein (Angelastro, et al. Regulated expression of ATF5 is required for the progression of neural progenitor cells to neurons, *J. Neurosci.,* 23: 4590-4600, 2003). Therefore, the inventors assessed whether ATF5 might be expressed in highly proliferative glial tumors. A series of 29 surgically resected human glioblastoma multiforme tumors (GBM, WHO Grade IV) were immunostained with ATF5 antiserum (McLendon, et al. Tumors of central neuroepithelial origin., p. 307-571, 1998; Kleihues, et al. Histology Typing of Tumours of the Central Nervous System, *Berlin: Springer-Verlag,* 1993). Positive specific nuclear staining was seen in the majority of glioma cells within all 29 tumors (FIG. 10). Tumor cells were identified on the basis of cytologic atypia. ATF5 staining was also seen in some cells with relatively round nuclei, which may represent reactive astrocytes, and in some endothelial cells in regions of microvascular proliferation (not shown). In contrast, there was little or no staining of neurons in the surrounding tissue.

Figure 11A:
FIG. 11 shows expression of ATF5 in glioma cell lines, cultured astrocytes and HEK 293 cells. (A) Western immunoblot probed with Anti-ATF5 antiserum reveals expression of ATF5 in lysates of rat PC12, C6 and RG2 glioma cells, human U251 glioma cells and human embryonic kidney 293 cells and the absent in low passage (passage 1-2; LP) neonatal astrocytes. (B) Percentages of cells in cultures of human and rat glioblastoma lines and of high passage (passage 5; HP) neonatal rat astrocytes positive for staining for endogenous ATF5 and for endogenous Ki67. GFP+ cells were scored 5 days after transfection with pLeGFP-C1. Values represent the mean±SEM for 3 cultures in which at least 100 transfected cells were evaluated per culture. Inspection of non-transfected cells revealed a similar level of staining.
Figure 11B:
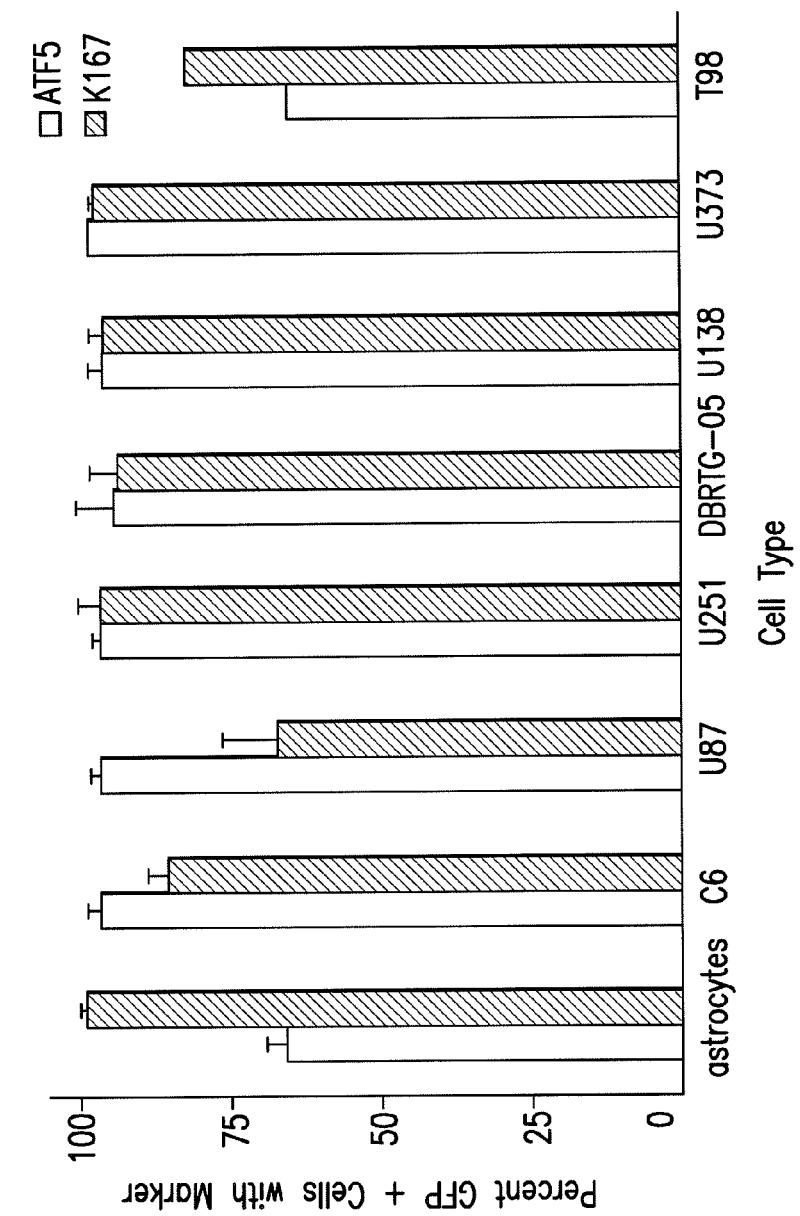

We also examined ATF5 expression by 6 well-characterized human and 2 rat glioma cell lines. All eight lines expressed nuclear ATF5 with 60-100% of the cells showing positive staining (FIG. 11). Western blotting confirmed the presence of ATF5 protein in these lines as a single 22 kDa band (FIG. 11 and data not shown). In contrast to the gliomas lines, cultured normal non-neoplasmic rat astrocytes isolated from neonatal rats, in first or second passage, as in vivo, showed little or no ATF5 expression as assessed by immunostaining and western immunoblotting (FIG. 11A). However, 60% of the cultured astrocytes expressed the protein when activated by 4-5 passages in vitro (FIG. 11B).

Figure 12:
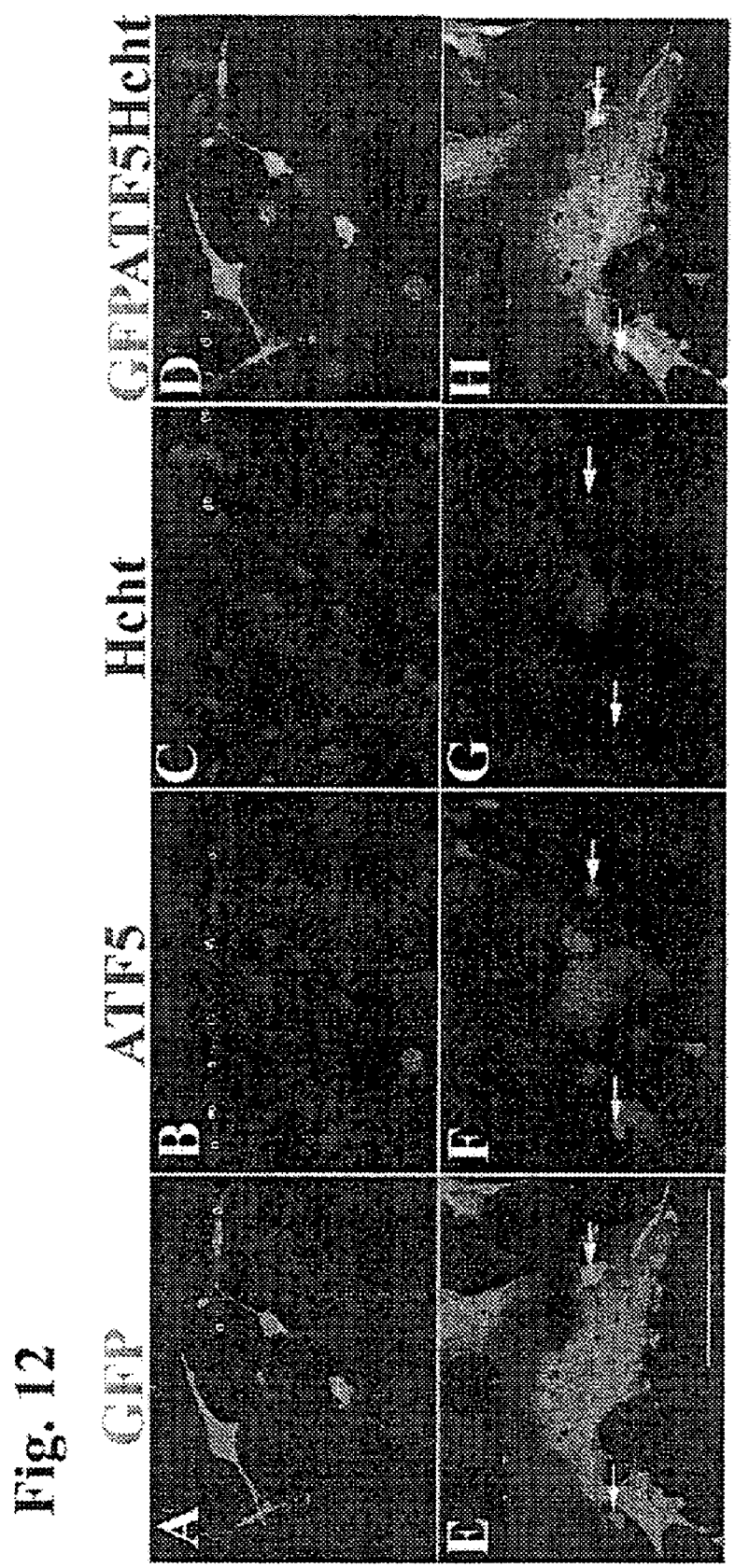
FIG. 12 demonstrates that dominant negative NT-Azip-ATF5 promotes multi-nucleated and apoptosis of U87 cells. U87 cells were transfected with pLeGFP-C1 (A-D), or transfected with pLeGFP-C1-NT-Azip-ATF5 (E-H). U87 cells were immunostained with anti-eGFP (A) and (E); or anti-ATF5-antiserum (B) and (F); Hoechst dye (C) and (G). All three staining were merged (D) and (H). Arrows show apoptotic nuclei. Scale bar is 10 µm.

Interfering with the Function or Expression of ATF5 Promotes Apoptosis of Glioma Cells, but not Activated Astrocytes, In Vitro We have observed that interfering with the expression or function of ATF5 in neural progenitor cells causes them to exit the cell cycle and to undergo accelerated differentiation (Angelastro, et al. Regulated expression of ATF5 is required for the progression of neural progenitor cells to neurons. *J. Neurosci.*, 23: 4590-4600, 2003). We therefore next determined whether glioma cells respond similarly. To interfere with function, we transfected the glioma lines with a dominant negative ATF5 construct (eGFP-NTAzip-ATF5) (Angelastro, et al. Regulated expression of ATF5 is required for the progression of neural progenitor cells to neurons. *J. Neurosci.*, 23: 4590-4600, 2003). Surprisingly, all 7 lines tested responded to the d/n construct by showing high levels of death compared with cells transfected with a control construct expressing eGFP (FIG. 12, 13A). By 5 days, 25-40% of the cells transfected with the d/n construct exhibited condensed chromatin indicative of apoptotic death (as compared with 2-8% of such cells transfected with the control construct). There was also significant increased amount of floating cellular debris in the cultures transfected with d/n construct, suggesting that the level of cell death was even higher than measured. To confirm that death was apoptotic and to determine whether it was caspase-dependent, C6 cells were transfected with d/n ATF5 in the presence and absence of the general caspase inhibitor BAF (Deshmukh, et al. Genetic and metabolic status of NGF-deprived sympathetic neurons saved by an inhibitor of ICE family proteases. *J. Cell Biol.*, 135: 1341-1354, 1996). This resulted in a 4-fold reduction in cell death. (data not shown).

To corroborate our findings with NTAzip-ATF5 and to rule out possible non-specific actions of d/n ATF5, we also employed a small interfering RNA oligoduplex (siRNA) that selectively down-regulates ATF5 expression (Angelastro, et al. Regulated expression of ATF5 is required for the progression of neural progenitor cells to neurons. *J. Neurosci.*, 23: 4590-4600, 2003). Compared with a control construct, the ATF5 siRNA promoted death of all 4 human glioma lines tested (FIG. 13B). We also used a construct that expresses a short hairpin ATF5 siRNA driven by a U6 promoter and that reduced by 80% the proportion of transfected cells (as compared with cells transfected with a control construct) that were positive for ATF5 immunostaining. In comparison with the control short hairpin siRNA-luciferase construct, the short hairpin ATF5 siRNA construct significantly elevated death in cultures of C6 rat gliomas cells (FIG. 13B). As in the case of cultures transfected with d/n ATF5, the cultures transfected with ATF5 siRNA constructs contained large amounts of floating debris, presumably derived from dead cells.

Death of cultured glioma cells caused by loss of ATF5 function or expression appeared to independent of p53. Although U87 and C6 cells express wild-type p53, lines U138, U251, U273 and T98 all have mutated, non-functional p53 genes (Asai, et al. Negative effects of wild-type p53 and s-Myc on cellular growth and tumorigenicity of glioma cells. Implication of the tumor suppressor genes for gene therapy. *J. Neurooncol.*, 19: 259-268, 1994; Yamagishi, et al. Modification of the radiosensitivity of human cells to which simian virus 40 T-antigen was transfected. *J. Radiat. Res. (Tokyo)*, 36: 239-247, 1995; Badie, et al. Combined radiation and p53 gene therapy of malignant glioma cells. *Cancer Gene Ther.*, 6: 155-162, 1999; Vogelbaum, et al. Overexpression of bax in human glioma cell lines. *J. Neurosurg.*, 91: 483-489, 1999). In addition, co-transfection with d/n p53 failed to rescue C6 cells from the apoptotic effects of d/n ATF5 (data not shown).

Figure 13:
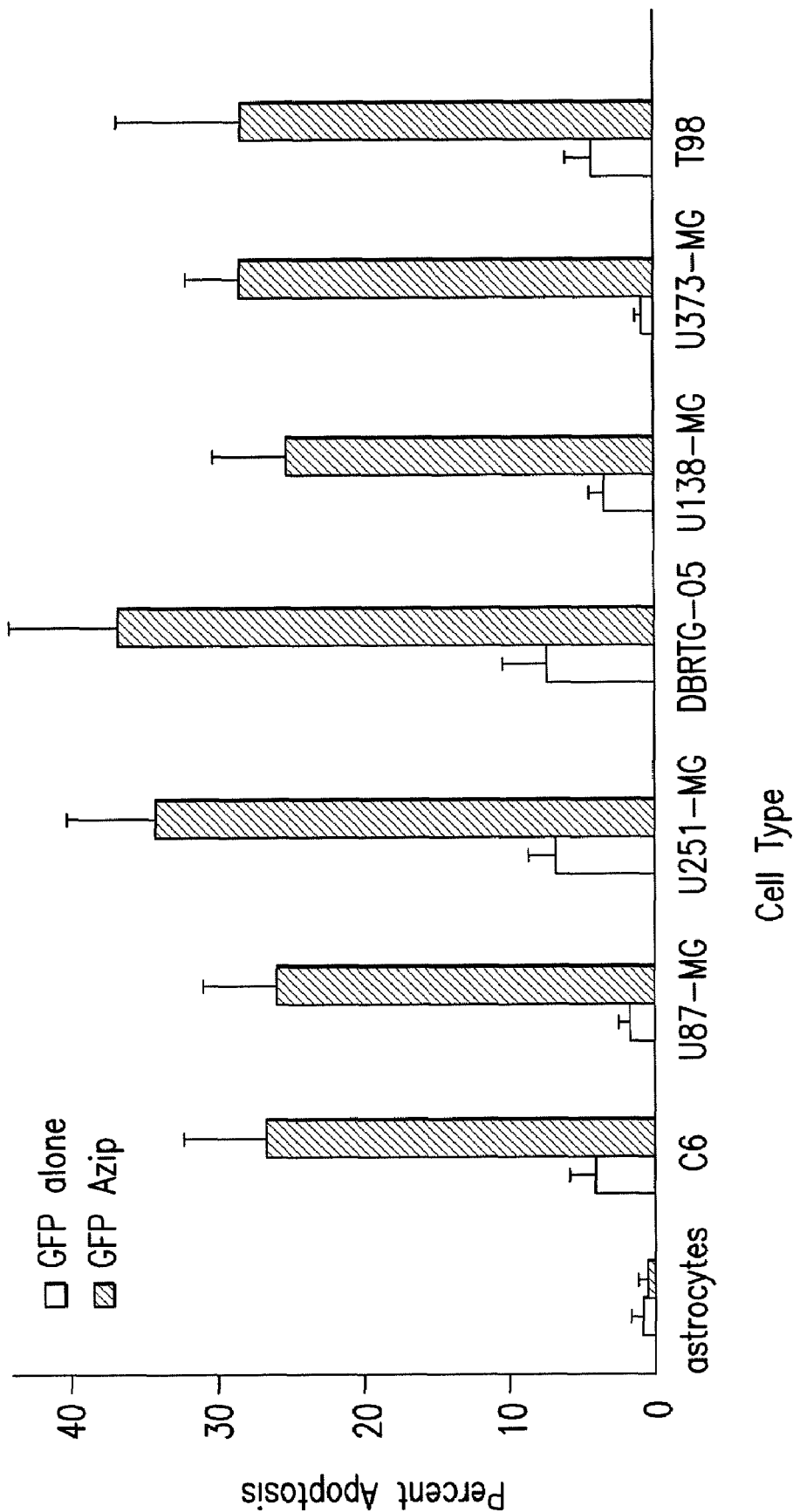
FIG. 13 shows that dominant negative ATF5 promotes and apoptosis of U87 cells. U87 cells were transfected with pLeGFP-C1 (A-D), or pLeGFP-C1-NT-Azip-ATF5 (E-H) and immunostained 5 days later with anti-eGFP (A,E)) or anti-ATF5 (B,F) antisera and with Hoechst nuclear dye 33258 (C,G). The merged images are shown in panels D and H. Arrows show apoptotic nuclei. Scale bar is 10 µm.

We next tested the ATF5 d/n and siRNA constructs for their capacity to trigger death of cultured astrocytes. In contrast with the cultured glioma cells, interfering with ATF5 function or expression had no significant effect on survival of either first passage rat astrocytes (data not shown) or on rat astrocytes that had undergone 5 passages (FIG. 13). As noted above, a majority of the latter cells express ATF5 (FIG. 11). In addition, two cell lines that express ATF5, HEK293 cells (Aiello, et al. Adenovirus 5 DNA sequences present and RNA sequences transcribed in transformed human embryo kidney cells (HEK-Ad-5 or 293). *Virology*, 94: 460-469, 1979) and CAD cells (Qi, et al. Characterization of a CNS cell line, CAD, in which morphological differentiation is initiated by serum deprivation. *J. Neurosci.*, 17: 1217-1225, 1997) showed no excess cell death when transfected with d/n ATF5 (data not shown). PC12 pheochromocytoma cells and embryonic neural progenitor cells also express high levels of ATF5 and their capacity to differentiate is accelerated by ATF5 d/n and siRNA constructs (Angelastro, et al. Regulated expression of ATF5 is required for the progression of neural progenitor cells to neurons. *J. Neurosci.*, 23: 4590-4600, 2003). However, in neither case did we observe promotion of death (data not shown). Taken together, these findings indicate that interfering with ATF5 function or expression causes death of cultured glioma cells but not of non-neoplastic astrocytes, or of several additional ATF5+ cell types.

ATF5 Loss-of-Function Promotes Selective Death of GBM Cells In Vivo

To extend our in vitro findings to an in vivo model and to further examine the specificity of the death evoked by ATF5 loss-of-function, we infected cells in rat glioma with a retrovirus expressing d/n ATF5. Tumors were created by stereotactic injection of C6 cells into the striatum of adult rats ($1 \times 10^4$ cells in 5 µl). Ten days later, retroviruses encoding eGFP or eGFP-NTAzip-ATF5 ($1.25 \times 10^4$ CFU in 5 µl) were stereotactically introduced into the tumors. Under these conditions, the tumors were large enough to inject, but had not formed large areas of internal necrosis that might interfere with detection of induced cell death. On day 13, the animals were sacrificed and the brains were analyzed by immunohistochemistry for retroviral infection (presence of eGFP) and for cell death (TUNEL staining) in the tumor and surrounding tissue.

For many of the animals, infected cells were detected not only within the tumors, but also in cells clearly outside the tumor margins. Although one cannot rule out with certainty that none of the infected cells outside the tumors were infiltrating tumor cells, it appears more likely that these were mainly generated from reactive astrocytes, or other endogenous proliferating cells that were infected by the viruses. When injected into adult rat brains, C6 cells form a well-circumscribed tumor with little infiltration. Moreover, the few cells in C6 tumors that do infiltrate, do so along blood vessels (Canoll et. al., unpublished data) and we did not observe that infected cells outside the tumors were associated with the vasculature. Rather, the cells mostly distributed throughout corpus callosum and had distribution and morphology most consistent with reactive astrocytes. For these reasons, infected cells that were within and outside of the tumors were separately scored for TUNEL staining.

Figure 14:
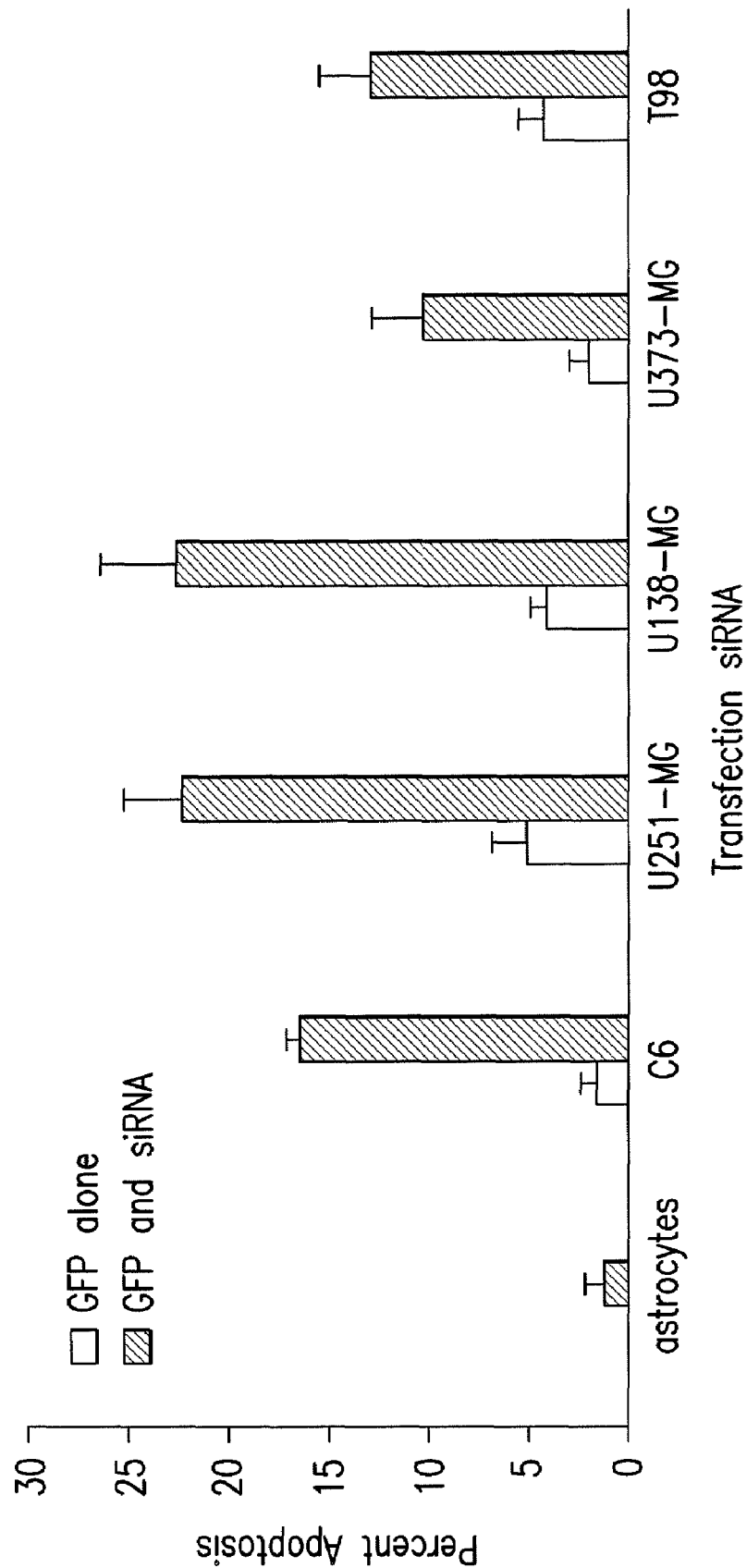
FIG. 14 shows (A) dominant negative ATF5 triggers apoptosis of cultured glioma cells, but not of activated astrocytes. Cultures were transfected with pLeGFP-C1 or pLeGFP-C1-NT-Azip-ATF5 as indicated and transfected cells (GFP+) were scored 5 days later for proportion with condensed apoptotic nuclei. Values represent the mean±SEM (n=3 cultures in which at least 100 transfected cells were evaluated per culture). (B) ATF5 siRNA triggers apoptosis of cultured glioma cells, but not of activated astrocytes. Human cells were co-transfected with pCMS-eGFP and human ATF5 oligo-duplex siRNA or pCMS-eGFP. Cultured rat astrocytes were similarly transfected, but with rat ATF5 oligo-duplex siRNA and pCMS-eGFP or pCMS-eGFP alone. C6 glioma cells were transfected with pQcSIREN-zsGreen small hairpin luciferase siRNA (control), or with pQcSIREN-zsGreen-small hairpin ATF5 siRNA. Five days later, transfected cells (GFP+cell, or zsGreen+) were scored for proportion with condensed apoptotic nuclei. Values represent the mean±SEM (n=3 cultures in which at least 100 transfected cells were evaluated per culture).
Figure 15:
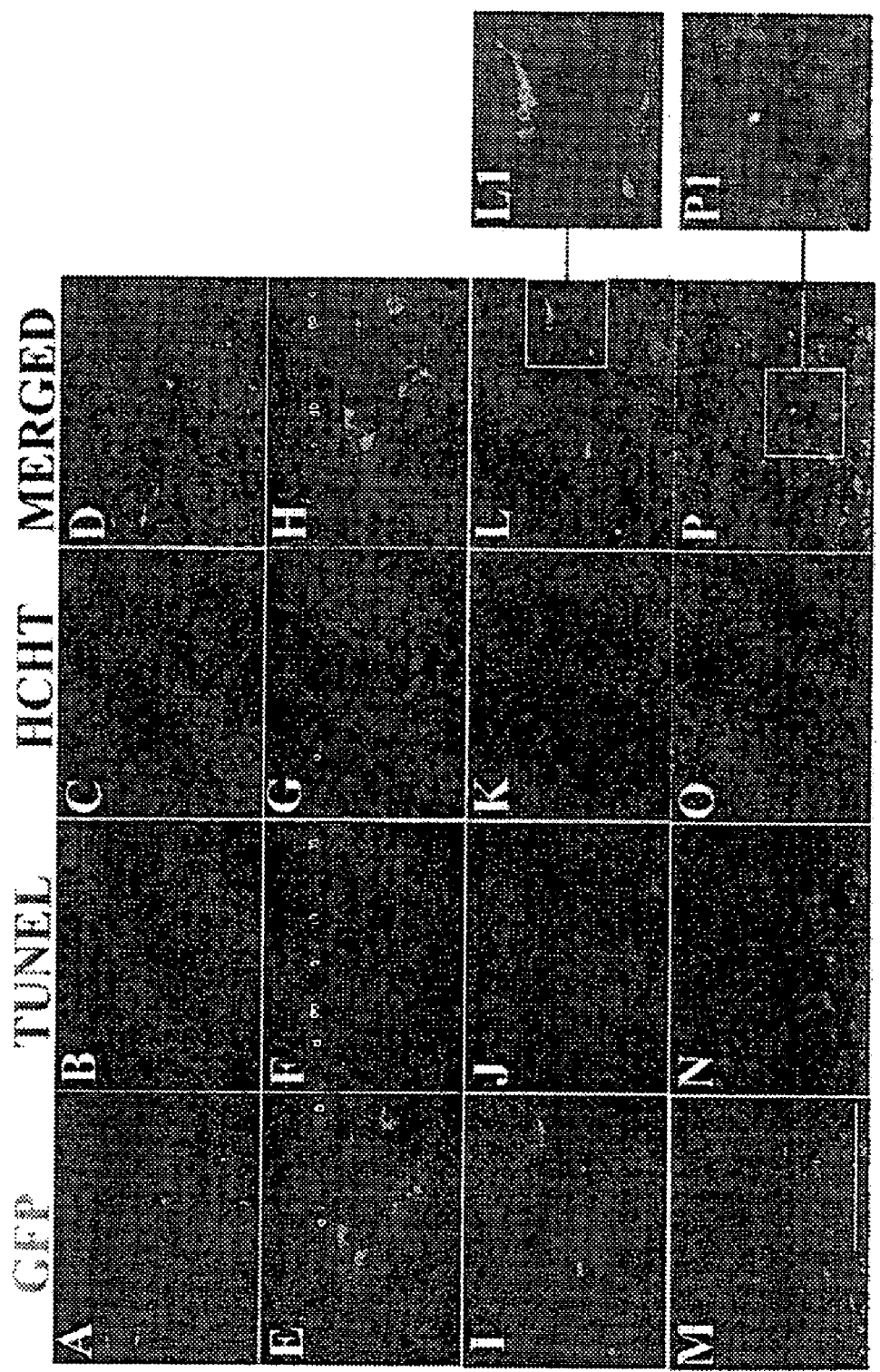
FIG. 15 shows that retroviral delivery of dominant negative NTAzip-ATF5 triggers death of C6 glioma cells in an in vivo tumor model, but spares cells outside the tumor. Tumors were induced in adult rat brains by stereotactic injection of approximately $1 \times 10^4$ C6 glioma cells into the striatum. Ten days later, retroviruses ($1.25 \times 10^4$ in 5 µl) expressing eGFP (control) or eGFP-NTAzip-ATF5 were stereotactically injected into the C6 tumors. Three days after the injection of retrovirus and a total of 13 days after the injection of C6 cells, the brains were removed, fixed, sectioned and stained for TUNEL (B,F,J,N) and then immunostained with rabbit-anti-eGFP antibodies (A,E,I,M) and stained with Hoechst nuclear dye 33258 (C,G,K,O). A-H. Cells in a tumor infected with control virus and found outside (A-D) or within (E-H) the tumor. I-P. Cells in a tumor infected with virus expressing eGFP-NTAzip-ATF5 found outside (I-L) or within (M-P) the tumor. Scale bar is 10 µm. L1 and P1 show enlargements of the areas within the boxes indicated in L and P, respectively. Note the presence of yellow cells (positive for both TUNEL and eGFP) in the merged images only in the case of cells within tumors infected with virus expressing eGFP-NTAzip-ATF5. Scale bar is 10 µm.
Figure 16:
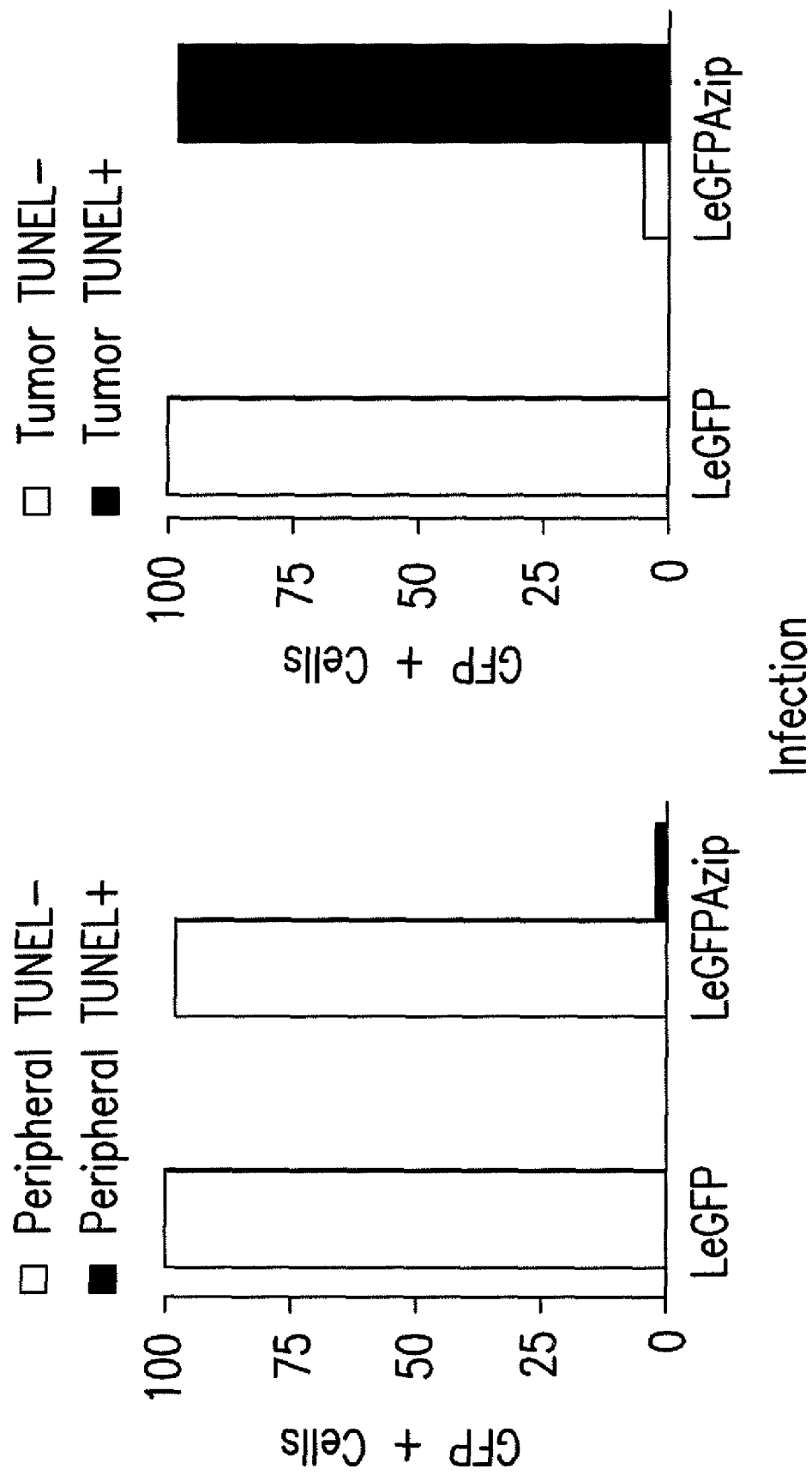
FIG. 16 depicts quantification of the selective death-promoting effects of NTAzip-ATF5 on cells within C6 brain tumors. Generation of C6 glioblastoma tumors and their infection with control eGFP (LeGFP) and NTAzip-ATF5 (LeGFP-Azip) expressing retroviruses were carried out as in FIG. 6. eGFP-positive cells were scored for the presence or absence of TUNEL staining. Four tumors injected with control virus were examined and a total of 252 infected cells were scored within the tumors and 194 outside the tumors. Five tumors injected with NTAzip-ATF5-expressing virus were examined and a total of 225 infected cells were scored within the tumors and 63 outside the tumors. Data represent proportions of total cells scored in each category that were positive or negative for TUNEL staining.

In the case of animals receiving the control virus, less than 1% (2/252) of the infected cells within the tumors were TUNEL+. Likewise, there were no TUNEL+ infected cells outside these tumors (0/194). In contrast, 96% (215/225) of the cells infected with the d/n ATF5-expressing virus and that were within the tumors were TUNEL+ (FIGS. 14 and 15). Inspection of the nuclei of such cells revealed that many were pyknotic or in various states of degeneration. By comparison, only 2% (1/63) of the infected cells outside the tumors were positive for TUNEL staining (FIGS. 14 and 15). Thus, interference with ATF5 function causes death of glioma cells in vivo, but spares cells outside the tumors.

These particular studies revealed that ATF5 was expressed by all 29 human GBMs we surveyed as well as by both rat and human glioma cell lines. Although ATF5 expression thus presently appears to be universal among glioblastomas, not all cells in the tumors were positive for ATF5 staining. This may reflect the findings of prior reports that ATF5 expression is largely limited to the G1 and S-phases of the cell cycle Pati, et al. Human Cdc34 and Rad6B ubiquitin-conjugating enzymes target repressors of cyclic AMP-induced transcription for proteolysis. *Mol. Cell. Biol.*, 19: 5001-5013, 1999; Persengiev, et al. Inhibition of apoptosis by ATFx: a novel role for a member of the ATF/CREB family of mammalian bZIP transcription factors. *Genes Dev.*, 16:1806-1814, 2002).

The expression of ATF5 in glioma cells contrasts with mature neurons, astrocytes and oligodendroglia in brain, which do not express detectable levels of ATF5 (Angelastro, et al. Regulated expression of ATF5 is required for the progression of neural progenitor cells to neurons. *J. Neurosc.*, 23: 4590-4600, 2003). On the other hand, ATF5 is highly expressed by brain neural progenitor/stem cells (Angelastro, et al. Regulated expression of ATF5 is required for the progression of neural progenitor cells to neurons. *J. Neurosc.*, 23: 4590-4600, 2003), as well as by reactive astrocytes. When constitutively expressed in neural progenitor cells, ATF5 blocks their differentiation into neurons and astrocytes and maintains them in a proliferative state, even in the presence of differentiation-promoting growth factors, such as NGF, NT3, and CNTF (Angelastro, et al. Regulated expression of ATF5 is required for the progression of neural progenitor cells to neurons. *J. Neurosci.*, 23: 4590-4600, 2003). This raises the possibility that ATF5 contributes to the relatively undifferentiated state of GBMs and to their capacity for uncontrolled growth. However, ATF5 expression alone does not appear to be sufficient for neoplastic transformation. When ATF5 was constitutively expressed in SVZ progenitors in vivo, these cells formed a non-invasive multi-layered hyperplastic mass by 3½ months post infection that exhibited the morphologic features of neural progenitors, but not of glioblastoma cells (Angelastro et al., unpublished data).

A somewhat unanticipated finding here was that ATF5 loss-of-function induced death of glioma cells both in culture and in vivo. This effect was independent of the delivery method employed in that both transient transfection and retroviral infection using the same d/n ATF5 construct produced similar results. Moreover, death was also induced by an ATF5 siRNA transfected either as an oligoduplex or hair-pin loop. Significantly, these destructive actions appeared to be selective for glioma cells. The d/n ATF5 had no effect on survival of ATF5-expressing astrocytes in culture or of retrovirally-infected and therefore proliferating) cells in brain that were found outside the margins of experimental tumors. There were also no apoptotic effects on cultured CAD neuroblast cells or human embryonic kidney 293 cells, both of which express detectable ATF5. We have also noted that ATF5 loss-of-function does not compromise survival of ATF5 positive PC12 rat pheochromocytoma cells (Angelastro, et al. Regulated expression of ATF5 is required for the progression of neural progenitor cells to neurons. *J. Neurosci.*, 23: 4590-4600, 2003), of brain neural progenitor/stem cells either in culture (Angelastro, et al. Regulated expression of ATF5 is required for the progression of neural progenitor cells to neurons. *J. Neurosci.*, 23: 4590-4600, 2003) or in vivo (Angelastro et. al., unpublished data) or of proliferating O4+ oligodendroglial progenitor cells in vitro or in developing brain (Mason, et. al., unpublished data).

The mechanisms by which loss of ATF5 function or expression lead to death of glioma cells remain to be fully explored. A p53-dependent mechanism appears to be ruled out in that a number of the susceptible glioma lines we used are deficient in p53 expression or activity and because we were unable to protect one line with normal p53 function from d/n-ATF5-promoted death by co-transfection with d/n p53. Moreover, over 70% of human GBMs are reported to be deficient in p53 expression, either due to direct mutations of this gene or of others that regulate p53 expression (Collins, V. P. Brain tumours: classification and genes. *J. Neurol. Neurosurg. Psychiatry*, 75 Suppl 2: ii2-11, 2004).

Impaired cell cycle control appears to be another major feature of glioblastomas (Collins, V. P. Brain tumours: classification and genes. *J. Neurol. Neurosurg. Psychiatry*, 75 Suppl 2: ii2-11, 2004) and it is in this context that ATF5 and ATF5 loss-of-function may act. As noted, ATF5 appears to play a role in regulating neural progenitor cell proliferation; constitutive expression of ATF5 maintains such cells in the cycle (even in presence of growth factors that would otherwise promote cell cycle exit), while ATF5 loss-of-function causes such cells to leave the cycle (Angelastro, et al. Regulated expression of ATF5 is required for the progression of neural progenitor cells to neurons. *J. Neurosci.*, 23: 4590-4600, 2003). One possibility is that ATF5 facilitates passage through critical check points during the cell cycle. In cells such as neural progenitors, loss of ATF5 expression or function may lead to withdrawal from the cycle, whereas in glioblastomas, with abnormal cell cycle control, even with ATF5 loss-of-function, the cells may attempt to continue cycling and pass through check points. Such inappropriate passage through check points could, in turn, lead to "mitotic catastrophe" and the triggering of cell death pathways (Canman, C. E. Replication checkpoint: preventing mitotic catastrophe. *Curr. Biol.*, 11: R121-124, 2001; Castedo, et al. Cell death by mitotic catastrophe: a molecular definition. *Oncogene*, 23: 2825-2837, 2004). Of potential relevance, inhibition of chk1, a kinase involved in enforcing the G2/M checkpoint, potentiated the capacity of the chemotherapeutic methylating agent temozolomide to promote mitotic catastrophe and death of cultured glioblastoma cell (Sonoda, et al. Formation of intracranial tumors by genetically modified human astrocytes defines four pathways critical in the development of human anaplastic astrocytoma. *Cancer Res.*, 61: 4956-4960, 2001; Hirose, et al. Abrogation of the Chk1-mediated G(2) checkpoint pathway potentiates temozolomide-induced toxicity in a p53-independent manner in human glioblastoma cells. *Cancer Res.*, 61: 5843-5849, 2001).

Yet another potential mechanism to account for our findings is that ATF5 acts as a survival factor and that interference with its function or expression therefore triggers death. Persengiev et al. (Persengiev, et al Inhibition of apoptosis by ATFx: a novel role for a member of the ATF/CREB family of mammalian bZIP transcription factors. *Genes Dev.*, 16:1806-1814, 2002) reported that ATF5 levels fall in several cell lines undergoing death evoked by trophic factor deprivation and that such death was suppressed by constitutive ATF5 expression. These authors also found that a d/n ATF5 lacking a transcriptional regulatory domain promoted death of HeLa and FL5.12 cells in presence of trophic support. It was further observed that constitutive expression of ATF5 does not affect FL5.12 cell proliferation and on this basis it was concluded that the activity of ATF5 is purely anti-apoptotic (Persengiev, et al. Inhibition of apoptosis by ATFx: a novel role for a member of the ATF/CREB family of mammalian bZIP transcription factors. *Genes Dev.*, 16: 1806-1814, 2002). Although our findings indicate that ATF5 can affect cell proliferation and differentiation and that its loss or absence (as in the case of mature neurons and glia) does not necessarily result in cell death, it remains possible that it acts as a survival factor for glioma cells independently from its role in cell growth.

In summary, these findings indicate that ATF5 is universally expressed by glioma cells and that interference with its function or expression leads to their death, both in vitro and in vivo. In contrast, ATF5 is undetectable in mature neurons and glia and abrogation of its expression or function does not cause death of brain cells that express this protein, including developing neural progenitor cells or activated astrocytes. These observations raise ATF5 as a potential therapeutic target for treatment of glioblastomas, either by direct intervention in its expression or activity such as achieved here, or by indirectly manipulating other molecules involved in its regulation or function.

Example 3

ATF5 is Widely Expressed in an Array of Different Tumor Types

The inventors have screened various tumor types for expression of ATF5. The screen was conducted using micro tissue array with anti-ATF5 antiserum, and the resulting data was interpreted by a pathologist. The results demonstrate that ATF5 is widely expressed by various tumor. The following is a list of specific tumor types that tested positive for ATF5 (number positive for ATF5/total number assessed): breast (20/28); ovary (18/26); endometrium (17/25); gastric (20/22); colon (20/24); liver (10/14); pancrease (26/28); kidney (16/22); bladder (24/26); prostate (20/22); testis (6/10); skin (8/10); esophagus (8/14); tongue (16/20); mouth (8/8); parotid (4/6); larynx (9/11); pharynx (2/4); lymph node (4/12); lung (22/24); and brain (8/12).

Example 4

Selective Interference with ATF5 Function in Breast Carcinoma Triggers Cell Death The inventors have provided the first study of ATF5 expression in human breast tissue. ATF5 expression was evaluated using immunohistochemistry, and cell culture experiments were performed to assess the effect of interfering with its function.

ATF5 antiserum was used to immunostain a cancer tissue microarray and additional paraffin-embedded sections of human breast tissue (10 ductal carcinomas, 7 lobular carcinomas, and 5 normal). Staining was quantified by determining the number of ATF5 positive nuclei (per 200 total nuclei in duct epithelium). ATF5 expression and apoptotic cell death were also evaluated in cell lines (5 breast cancer and 3 normal) transfected with a control or ATF5 dominant negative construct.

Immunostaining of all sections showed 93% of invasive breast carcinomas stained strongly for ATF5. The proportion of ATF5-positive nuclei in paraffin-embedded sections was 45±4% (controls), 80±4% (in-situ ductal), 73+7% (in-sutu lobular), 82+2% (invasive ductal), and 83+3% (invasive lobular). The breast stroma was consistently negative. Apoptosis in neoplastic cells transfected with the dominant negative ATF5 was significantly greater than in cells transfected with the control construct. In contrast, cell death in non-neoplastic cells was not significantly altered.

The results indicate that ATF5 is highly expressed in breast carcinoma and, to a lesser extent, in normal breast tissue cells. Interference with ATF5 function triggers increased cell death in neoplastic, but not normal breast cells. The tumor specific effect of interference with ATF5 function likely has important implications for therapeutic approaches to breast carcinoma.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A method for promoting apoptosis in a neoplastic cell, comprising contacting the neoplastic cell with an ATF5 inhibitor.

2. The method of claim 1, wherein the neoplastic cell is selected from the group consisting of: breast, ovary, endometrium, gastric, colon, liver, pancreas, kidney, bladder, prostate, testis, skin, esophagus, tounge, mouth, parotid, larynx, pharynx, lymph node, lung, and brain.

3. The method of claim 1, wherein the neoplastic cell is selected from the group consisting of a glioblastoma, an astrocytoma, a glioma, a medulloblastoma and a neuroblastoma.

4. The method of claim 1, wherein the ATF5 inhibitor is a nucleic acid.

5. The method of claim 1, wherein the ATF5 inhibitor is a dominant negative form of ATF5 which inhibits binding to CRE.

6. The method of claim 5, wherein the dominant negative form is NTAzip-ATF5.

7. The method of claim 1, wherein the ATF5 inhibitor is an ATF5 siRNA.

8. The method of claim 1, wherein the method is performed in vitro.

9. A method for treating or preventing a tumor in a subject, comprising the step of
directly contacting the brain tumor with an amount of ATF5 inhibitor effective to induce apoptosis in the tumor cells, thereby treating the tumor.

10. The method of claim 9, wherein the tumor is selected from the group consisting of: breast, ovary, endometrium, gastric, colon, liver, pancreas, kidney, bladder, prostate, testis, skin, esophagus, tounge, mouth, parotid, larynx, pharynx, lymph node, lung, and brain.

11. The method of claim 9, wherein the tumor is selected from the group consisting of a glioblastoma, an astrocytoma, a glioma, a medulloblastoma and a neuroblastoma.

12. The method of claim 9, wherein the ATF5 inhibitor is a nucleic acid.

13. The method of claim 9, wherein the ATF5 inhibitor is a dominant negative form of ATF5, which inhibits binding to CRE.

14. The method of claim 13, wherein the dominant negative form is NTAzip-ATF5.

15. The method of claim 9, wherein the ATF5 inhibitor is an ATF5 siRNA.

* * * * *

SEQUENCE LISTING

```
<160> NUMBER OF SEQ ID NOS: 19

<210> SEQ ID NO 1
<211> LENGTH: 1034
<212> TYPE: DNA
<213> ORGANISM: Rattus norvegicus

<400> SEQUENCE: 1
gcacctgtgc ctcagccatg tcactcctgg cgaccctggg actggagctg gacagggccc      60
tgctcccagc tagcgggctg ggctggctcg tagactatgg gaaactcccc ctggcccctg     120
cccccctggg cccctatgag gtccttgggg gtgccctgga gggcgggctt ccaggggggg     180
gagagcccct ggcaggtgac ggcttctctg attggatgac cgagcgggtg gacttcacag     240
ccctccttcc tctggaggcc cctctgcccc caggcactct cccccacccc tccctgccc      300
```

```
cccctgacct ggaagccatg gcatccctac tcaagaagga gctagaacag atggaagact    360
tcttccttga tgccccactc cttccaccgc cctcccacc tccacccca cccccagcac      420 cctctctgcc cctgcccta cccttgccca cctttgatct cccgcagcct cctaccctgg     480
ataccctgga cttgctagct gtttactgcc gcagtgaggc tgggccaggg gattcaggct    540
tgacaaccct gcctgtcccc cagcagcctc ctcctctggc ccctctgcct tcacctccc     600 gaccagcccc ctatcctagt cctgccagca cccgagggga ccgcaagcaa agaagagag     660 accagaataa gtcagctgct ctcaggtacc gccagaggaa gcgggcagag ggcgaggccc    720
tggagggcga gtgccaaggg ctagaggcgc ggaatcggga gctgagggag agggcagagt    780
cagtggaacg ggagatccag tatgtgaagg atctgctaat tgaggtgtat aaggcacgaa    840
gccagaggac ccgcagtgcc tagggtacag gaggaggcag ttctggtgta cctgtgcctc    900
cagcttcacc ctgtccctcc atttcacttc cctgtgcatc cgtgtctagg tctcccctct    960
gcctatcccc attatgggtt atttggcata gtcagtttct gtaccccttc agtgcaactg   1020
agaaccaagc tcga                                                     1034
```

<210> SEQ ID NO 2
<211> LENGTH: 281
<212> TYPE: PRT
<213> ORGANISM: Rattus norvegicus

<400> SEQUENCE: 2

```
Met Ser Leu Leu Ala Thr Leu Gly Leu Glu Leu Asp Arg Ala Leu Leu
 1               5                  10                  15

Pro Ala Ser Gly Leu Gly Trp Leu Val Asp Tyr Gly Lys Leu Pro Leu
                20                  25                  30

Ala Pro Ala Pro Leu Gly Pro Tyr Glu Val Leu Gly Ala Leu Glu
            35                  40                  45

Gly Gly Leu Pro Gly Gly Gly Glu Pro Leu Ala Gly Asp Gly Phe Ser
        50                  55                  60

Asp Trp Met Thr Glu Arg Val Asp Phe Thr Ala Leu Leu Pro Leu Glu
65                  70                  75                  80

Ala Pro Leu Pro Pro Gly Thr Leu Pro Pro Ser Pro Ala Pro Pro
                85                  90                  95

Asp Leu Glu Ala Met Ala Ser Leu Leu Lys Lys Glu Leu Glu Gln Met
            100                 105                 110

Glu Asp Phe Phe Leu Asp Ala Pro Leu Leu Pro Pro Ser Pro Pro
        115                 120                 125

Pro Pro Pro Pro Ala Pro Ser Leu Pro Leu Pro Leu Pro Leu Pro
    130                 135                 140

Thr Phe Asp Leu Pro Gln Pro Pro Thr Leu Asp Thr Leu Asp Leu Leu
145                 150                 155                 160

Ala Val Tyr Cys Arg Ser Glu Ala Gly Pro Gly Asp Ser Gly Leu Thr
                165                 170                 175

Thr Leu Pro Val Pro Gln Gln Pro Pro Leu Ala Pro Leu Pro Ser
            180                 185                 190

Pro Ser Arg Pro Ala Pro Tyr Pro Ser Pro Ala Ser Thr Arg Gly Asp
        195                 200                 205

Arg Lys Gln Lys Lys Arg Asp Gln Asn Lys Ser Ala Ala Leu Arg Tyr
    210                 215                 220

Arg Gln Arg Lys Arg Ala Glu Gly Glu Ala Leu Glu Gly Glu Cys Gln
225                 230                 235                 240
```

```
Gly Leu Glu Ala Arg Asn Arg Glu Leu Arg Glu Arg Ala Glu Ser Val
                245                 250                 255

Glu Arg Glu Ile Gln Tyr Val Lys Asp Leu Leu Ile Glu Val Tyr Lys
            260                 265                 270

Ala Arg Ser Gln Arg Thr Arg Ser Ala
        275                 280

<210> SEQ ID NO 3
<211> LENGTH: 15
<212> TYPE: DNA
<213> ORGANISM: Rattus norvegicus

<400> SEQUENCE: 3
catgagaacc tagtc                                                    15

<210> SEQ ID NO 4
<211> LENGTH: 19
<212> TYPE: DNA
<213> ORGANISM: Artificial Sequence
<220> FEATURE:
<223> OTHER INFORMATION: synthetic primer

<400> SEQUENCE: 4
cttggtttct cagttgcac                                                19

<210> SEQ ID NO 5
<211> LENGTH: 23
<212> TYPE: DNA
<213> ORGANISM: Artificial Sequence
<220> FEATURE:
<223> OTHER INFORMATION: synthetic primer

<400> SEQUENCE: 5
tgcacctgtg cctcagccat gtc                                           23

<210> SEQ ID NO 6
<211> LENGTH: 57
<212> TYPE: DNA
<213> ORGANISM: Artificial Sequence
<220> FEATURE:
<223> OTHER INFORMATION: synthetic primer

<400> SEQUENCE: 6
ctcgagaacc atggactaca aggacgatga tgacaaagga tcactcctgg cgaccct      57

<210> SEQ ID NO 7
<211> LENGTH: 57
<212> TYPE: DNA
<213> ORGANISM: Artificial Sequence
<220> FEATURE:
<223> OTHER INFORMATION: synthetic primer

<400> SEQUENCE: 7
ctcgagaagc atggactaca aggacgatga tgacaaagga gcatccctac tcaagaa      57

<210> SEQ ID NO 8
<211> LENGTH: 30
<212> TYPE: DNA
<213> ORGANISM: Artificial Sequence
<220> FEATURE:
<223> OTHER INFORMATION: synthetic primer

<400> SEQUENCE: 8
gaattctcga gcttggtttc tcagttgcac                                    30
```

<210> SEQ ID NO 9
<211> LENGTH: 87
<212> TYPE: DNA
<213> ORGANISM: Artificial Sequence
<220> FEATURE:
<223> OTHER INFORMATION: synthetic primer

<400> SEQUENCE: 9
ttcttctgct tcttttctta gtagttcttc gttttctctt gctagttctt ctgctctttg    60
ttcgagggtg ctggcaggac taggata                                        87

<210> SEQ ID NO 10
<211> LENGTH: 83
<212> TYPE: DNA
<213> ORGANISM: Artificial Sequence
<220> FEATURE:
<223> OTHER INFORMATION: synthetic primer

<400> SEQUENCE: 10
gcaagagaaa acgaagaact actagaaaaa gaagcagaag aactagaaca agaaatgcag    60
agctagaggg cgagtgccaa ggg                                            83

<210> SEQ ID NO 11
<211> LENGTH: 100
<212> TYPE: DNA
<213> ORGANISM: Artificial Sequence
<220> FEATURE:
<223> OTHER INFORMATION: synthetic primer

<400> SEQUENCE: 11
gaattcaacc atggactaca aggacgatga tgacaaaatg gcatctatga ctggaggaca    60
acaaatggga agagacccag acctcgaaca aagagcagaa                         100

<210> SEQ ID NO 12
<211> LENGTH: 99
<212> TYPE: PRT
<213> ORGANISM: Artificial Sequence
<220> FEATURE:
<223> OTHER INFORMATION: synthetic tag

<400> SEQUENCE: 12

Met Asp Tyr Lys Asp Asp Asp Lys Met Ala Ser Met Thr Gly Gly
1               5                   10                  15

Gln Gln Met Gly Arg Asp Pro Asp Leu Glu Gln Arg Ala Glu Glu Leu
            20                  25                  30

Arg Glu Asn Glu Glu Leu Leu Glu Lys Glu Ala Glu Glu Leu Glu Gln
        35                  40                  45

Glu Asn Ala Glu Leu Glu Gly Glu Cys Gln Gly Leu Glu Ala Arg Asn
    50                  55                  60

Arg Glu Leu Arg Glu Arg Ala Glu Ser Val Glu Arg Glu Ile Gln Tyr
65                  70                  75                  80

Val Lys Asp Leu Leu Ile Glu Val Tyr Lys Ala Arg Ser Gln Arg Thr
                85                  90                  95

Arg Ser Ala

<210> SEQ ID NO 13
<211> LENGTH: 92
<212> TYPE: DNA
<213> ORGANISM: Artificial Sequence
<220> FEATURE:
<223> OTHER INFORMATION: synthetic oligonucleotide

```
<400> SEQUENCE: 13
tcgagtcatg gtaaaaatga cgtcatggta attatcatgg taaaaatgac gtcatggtaa    60
ttatcatggt aaaaatgacg tcatggtaat ta                                  92

<210> SEQ ID NO 14
<211> LENGTH: 92
<212> TYPE: DNA
<213> ORGANISM: Artificial Sequence
<220> FEATURE:
<223> OTHER INFORMATION: synthetic oligonucleotide

<400> SEQUENCE: 14
agcttaatta ccatgacgtc attttttacca tgataattac catgacgtca ttttttaccat    60 gataattacc atgacgtcat ttttaccatg ac                                  92

<210> SEQ ID NO 15
<211> LENGTH: 15
<212> TYPE: PRT
<213> ORGANISM: Artificial Sequence
<220> FEATURE:
<223> OTHER INFORMATION: synthetic peptide

<400> SEQUENCE: 15

Cys Thr Arg Gly Asp Arg Lys Gln Lys Lys Arg Asp Gln Asn Lys
  1               5                  10                  15

<210> SEQ ID NO 16
<211> LENGTH: 21
<212> TYPE: RNA
<213> ORGANISM: Artificial Sequence
<220> FEATURE:
<223> OTHER INFORMATION: synthetic siRNA primer

<400> SEQUENCE: 16
aagucagcug cucucaggua c                                              21

<210> SEQ ID NO 17
<211> LENGTH: 65
<212> TYPE: DNA
<213> ORGANISM: Artificial Sequence
<220> FEATURE:
<223> OTHER INFORMATION: synthetic siRNA primer

<400> SEQUENCE: 17
gatccgtcag ctgctctcag gtacttcaag agagtacctg agagcagctg accttttttc    60
tagag                                                                65

<210> SEQ ID NO 18
<211> LENGTH: 21
<212> TYPE: RNA
<213> ORGANISM: Artificial Sequence
<220> FEATURE:
<223> OTHER INFORMATION: synthetic siRNA primer

<400> SEQUENCE: 18
aagucagcug cucucaggua c                                              21

<210> SEQ ID NO 19
<211> LENGTH: 21
<212> TYPE: RNA
```

```
<213> ORGANISM: Artificial Sequence
<220> FEATURE:
<223> OTHER INFORMATION: synthetic siRNA primer

<400> SEQUENCE: 19
aagucggcgg cucugaggua c                                                21
```